(12) United States Patent
Garvey et al.

(10) Patent No.: US 7,244,753 B2
(45) Date of Patent: *Jul. 17, 2007

(54) CYCLOOXYGENASE-2 SELECTIVE INHIBITORS, COMPOSITIONS AND METHODS OF USE

(75) Inventors: David S. Garvey, Dover, MA (US); Subhash P. Khanapure, Clinton, MA (US); Ramani R. Ranatunge, Lexington, MA (US); Stewart K. Richardson, Tolland, CT (US); Joseph D. Schroeder, Minneapolis, MN (US)

(73) Assignee: NitroMed, Inc., Lexington, MA (US)

( * ) Notice: Subject to any disclaimer, the term of this patent is extended or adjusted under 35 U.S.C. 154(b) by 369 days.

This patent is subject to a terminal disclaimer.

(21) Appl. No.: 10/628,375

(22) Filed: Jul. 29, 2003

(65) Prior Publication Data
US 2004/0072883 A1 Apr. 15, 2004

Related U.S. Application Data

(60) Provisional application No. 60/398,829, filed on Jul. 29, 2002.

(51) Int. Cl.
*A61K 31/427* (2006.01)
*A61K 31/422* (2006.01)
*A61K 31/4015* (2006.01)
*C07D 417/02* (2006.01)
*C07D 413/02* (2006.01)

(52) U.S. Cl. ............. 514/365; 514/374; 514/397; 514/424; 514/461; 548/376.1; 548/377.1

(58) Field of Classification Search ........ 514/406; 548/376.1, 377.1
See application file for complete search history.

(56) References Cited

U.S. PATENT DOCUMENTS

| | | |
|---|---|---|
| 5,360,925 A | 11/1994 | Chabrier de Lassauniere et al. |
| 5,607,966 A | 3/1997 | Hellberg et al. |
| 5,621,000 A | 4/1997 | Arena et al. |
| 5,700,947 A | 12/1997 | Del Soldato |
| 5,703,073 A | 12/1997 | Garvey et al. |
| 5,733,909 A | 3/1998 | Black et al. |
| 5,780,495 A | 7/1998 | Del Soldato |
| 5,789,413 A | 8/1998 | Black et al. |
| 5,811,438 A | 9/1998 | Helberg et al. |
| 5,849,943 A | 12/1998 | Atkinson et al. |
| 5,859,053 A | 1/1999 | Lesur et al. |
| 5,861,426 A | 1/1999 | Del Soldato et al. |
| 5,925,631 A | 7/1999 | Black et al. |
| 6,040,341 A | 3/2000 | Del Soldato et al. |
| 6,043,233 A | 3/2000 | Garvey et al. |
| 6,046,191 A | 4/2000 | Hamley et al. |
| 6,048,858 A | 4/2000 | Garvey et al. |
| 6,051,588 A | 4/2000 | Garvey et al. |
| 6,057,347 A | 5/2000 | Garvey et al. |
| 6,083,515 A | 7/2000 | Garvey et al. |
| 6,143,734 A | 11/2000 | Garvey et al. |
| 6,248,745 B1 | 6/2001 | Hamley et al. |
| 6,297,260 B1 | 10/2001 | Bandarage et al. |
| 6,323,234 B1 | 11/2001 | Garvey et al. |
| 6,355,666 B1 | 3/2002 | Lai et al. |
| 6,365,184 B1 | 4/2002 | Depui et al. |
| 6,369,260 B1 | 4/2002 | Sannicolo' et al. |
| 6,429,223 B1 | 8/2002 | Lai et al. |
| 6,436,990 B1 | 8/2002 | Ekwuribe et al. |
| 6,482,846 B1 | 11/2002 | Garvey et al. |
| 6,512,137 B1 | 1/2003 | Del Soldato et al. |
| 6,525,098 B1 | 2/2003 | Ekwuribe et al. |

(Continued)

FOREIGN PATENT DOCUMENTS

EP 0 440 098 8/1991

(Continued)

OTHER PUBLICATIONS

Gu, Qu-Ming, Ching-Shih Chen and C. J. Sih. 1986. "A Facile Enzymatic Resolution Process for the Preparation of (+)-S-2-(6-Methoxy-2-Naphthyl) Propionic Acid (Naproxen)." *Tetrahedron Letters*, vol. 27, No. 16. pp. 1763-1766.

(Continued)

*Primary Examiner*—Kamal A. Saeed
(74) *Attorney, Agent, or Firm*—Wilmer Cutler Pickering Hale and Dorr LLP

(57) ABSTRACT

The invention describes novel cyclooxygenase 2 (COX-2) selective inhibitors and novel compositions comprising at least one cyclooxygenase 2 (COX-2) selective inhibitor, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one therapeutic agent. The invention also provides novel kits comprising at least one COX-2 selective inhibitor, optionally nitrosated and/or nitrosylated, and, optionally, at least one nitric oxide donor, and/or, optionally, at least one therapeutic agent. The novel cyclooxygenase 2 selective inhibitors of the invention can be optionally nitrosated and/or nitrosylated. The invention also provides methods for treating inflammation, pain and fever; for treating and/or improving the gastrointestinal properties of COX-2 selective inhibitors; for facilitating wound healing; for treating and/or preventing renal and/or respiratory toxicity; for treating and/or preventing other disorders resulting from elevated levels of cyclooxygenase-2; and for improving the cardiovascular profile of COX-2 selective inhibitors.

20 Claims, No Drawings

U.S. PATENT DOCUMENTS

| | | | |
|---|---|---|---|
| 6,552,078 | B2 | 4/2003 | Ekwuribe et al. |
| 6,593,347 | B2 | 7/2003 | Bandarage et al. |
| 2001/0041726 | A1 | 11/2001 | Bandarage et al. |
| 2002/0028845 | A1 | 3/2002 | Ekwuribe et al. |
| 2002/0111370 | A1 | 8/2002 | Bergman et al. |
| 2003/0088111 | A1 | 5/2003 | Lai et al. |

FOREIGN PATENT DOCUMENTS

| | | |
|---|---|---|
| EP | 0 676 204 | 10/1995 |
| EP | 0 656 881 | 10/1998 |
| EP | 0 904 110 | 7/2002 |
| WO | WO 94/03421 | 2/1994 |
| WO | WO 94/04484 | 3/1994 |
| WO | WO 94/12463 | 6/1994 |
| WO | WO 95/09831 | 4/1995 |
| WO | WO 95/30641 | 11/1995 |
| WO | WO 96/13483 | 5/1996 |
| WO | WO 96/32946 | 10/1996 |
| WO | WO 97/16405 | 5/1997 |
| WO | WO 97/28120 | 8/1997 |
| WO | WO 97/28121 | 8/1997 |
| WO | WO 97/31654 | 9/1997 |
| WO | WO 97/36863 | 10/1997 |
| WO | WO 98/09948 | 3/1998 |
| WO | WO 98/25981 | 6/1998 |
| WO | WO 99/44595 | 9/1999 |
| WO | WO 99/45004 | 9/1999 |
| WO | WO 00/00200 | 1/2000 |
| WO | WO 00/06585 | 2/2000 |
| WO | WO 00/25776 | 5/2000 |
| WO | WO 00/44705 | 8/2000 |
| WO | WO 00/51988 | 9/2000 |
| WO | WO 00/61537 | 10/2000 |
| WO | WO 00/61541 | 10/2000 |
| WO | WO 00/61549 | 10/2000 |
| WO | WO 00/61604 | 10/2000 |
| WO | WO 00/72838 | 12/2000 |
| WO | WO 01/00563 | 1/2001 |
| WO | WO 01/04082 | 1/2001 |
| WO | 01/12621 | 2/2001 |
| WO | WO 01/10814 | 2/2001 |
| WO | WO 01/12584 | 2/2001 |
| WO | WO 01/49275 | 7/2001 |
| WO | WO 01/66088 | 9/2001 |
| WO | WO 01/78781 | 10/2001 |
| WO | WO 01/87343 | 11/2001 |
| WO | WO 01/93680 | 12/2001 |
| WO | WO 02/00166 | 1/2002 |
| WO | WO 02/00167 | 1/2002 |
| WO | WO 02/11706 | 2/2002 |
| WO | WO 02/11707 | 2/2002 |
| WO | WO 02/30866 | 4/2002 |
| WO | WO 02/051385 | 7/2002 |
| WO | WO 02/053188 | 7/2002 |
| WO | WO 02/092072 | 11/2002 |
| WO | WO 02/100400 | 12/2002 |
| WO | WO 03/000642 | 1/2003 |
| WO | WO 03/000643 | 1/2003 |
| WO | WO 03/022249 | 3/2003 |

OTHER PUBLICATIONS

Palmer, R. M. J., D. S. Ashton and S. Moncada. Jun. 16, 1988. "Vascular endothelial cells synthesize nitric oxide from L-arginine." *Nature*, vol. 333. pp. 664-666.

MacNaughton, Wallace K., Giuseppe Cirino and John L. Wallace. Sep. 5, 1989. "Endothelium-Derived Relaxing Factor (Nitric Oxide) Has Protective Actions in the Stomach." *Life Sciences*, vol. 45. pp. 1869-1876.

Kitagawa, Hisato, Fumiyo Takeda and Hiroshi Kohei. Mar. 15, 1990. "Effect of Endothelium-Derived Relaxing Factor on The Gastric Lesion Induced by HCI in Rats." *The Journal of Pharmacology and Experimental Therapeutics*, vol. 253, No. 3. pp. 1133-1137.

Boughton-Smith, Nigel K., Iain R. Hutcheson, Angela M. Deakin, Brendan J. R. Whittle and S. Moncada. Oct. 23, 1990. "Protective effect of S-nitroso-N-acetyl-penicillamine in endotoxin-induced acute intestinal damage in the rat." *European Journal of Pharmacology*, vol. 191. pp. 485-488.

Brown, James F., Peter J. Hanson, and Brendan J. R. Whittle. Oct. 13, 1992. "Nitric oxide donors increase mucus gel thickness in rat stomach." *European Journal of Pharmacology*, vol. 223. pp. 103-104.

Conforti, A., M. Donini, G. Brocco, P. Del Soldato, G. Benoni, and L. Cuzzolin. 1993. "Acute anti-inflammatory activity and gastrointestinal tolerability of diclofenac and nitrofenac." *Agents Actions*, vol. 40. pp. 176-180.

Reuter, B. K., G. W. McKnight, G. Cirino and J. L. Wallace. 1993. "Nitric Oxide Releasing Nsaid Derivatives Do Not Cause Intestinal Injury or Exacerbate Pre-Existing Colitis." *Castagliuolo I et al. Gastroenterology*, vol. 104, No. A678.

Konturek, Stanislaw J., Tomasz Brzozowski, Jolanta Majka, Jolanta Pytko-Polonczyk and Jerzy Stachura. Jun. 1, 1993. "Inhibition of nitric oxide synthase delays healing of chronic gastric ulcers." *European Journal of Pharmacology*, vol. 239. pp. 215-217.

Carty, Thomas J.. 1993. "Ampiroxicam, an anti-inflammatory agent which is a prodrug of piroxicam." *Agents Actions*, vol. 39. pp. 158-165.

Cuzzolin, Laura et al.. 1994. "Effects on Intestinal Microflora, Gastrointestinal Tolerability and Antiinflammatory Efficacy of Diclofenac and Nitrofenac in Adjuvant Arthritic Rats." *Pharmacological Research*, vol. 29, No. 1. pp. 89-97.

Rachmilewitz, D. et al. 1994. "Enhanced gastric nitric oxide synthase activity in duodenal ulcer patients." *Gut*, vol. 35. pp. 1394-1397.

Wallace, John L. et al. Mar. 8, 1994. "A diclofenac derivative without ulcerogenic properties." *European Journal of Pharmacology*, vol. 257. pp. 249-255.

Reuter, Brian K., Giuseppe Cirino and John L. Wallace. Apr. 18, 1994. "Markedly Reduced Intestinal Toxicity of a Diclofenac Derivative." *Life Sciences*, vol. 55, No. 1. pp. PL-1-PL-8.

Wallace, John L. and Giuseppe Cirino. 1994. "The development of gastrointestinal-sparing nonsteroidal anti-inflammatory drugs." *TiPS*, vol. 15. pp. 405-406.

Wallace, J. L., B. K. Reuter and G. Cirino. Jun. 8, 1994. "Nitric oxide-releasing non-steroidal anti-inflammatory drugs: A novel approach for reducing gastrointestinal toxicity." *Journal of Gastroenterology and Hepatology*, vol. 9. pp. S40-S44.

Wallace, John L. et al. 1994. "Novel Nonsteroidal Anti-inflammatory Drug Derivatives With Markedly Reduced Ulcerogenic Properties in the Rat." *Gastroenterology*, vol. 107. pp. 173-179.

Wallace, John L., Quentin J. Pittman and Giuseppe Cirino. 1995. "Nitric Oxide-Releasing NSAIDs" A Novel Class of GI-Sparing Anti-Inflammatory Drugs. *Novel Molecular Approaches to Anti-Inflammatory Theory*. pp. 121-129.

Wallace, John L., G. Cirino, G. Webb McKnight and Susan N. Elliott. Mar. 21, 1995. "Reduction of gastrointestinal injury in acute endotoxic shock by flurbiprofen nitroxybutylester." *European Journal of Pharmacology*, vol. 280. pp. 63-68.

Wallace, John L., Piero Del Soldato and Giuseppe Cirino. 1995. "Pulmonary-Allergy, Dermatological, Gastrointestinal & Arthritis." *Exp. Opin. Invest. Drugs*, vol. 4, No. 7. pp. 613-619.

Barrachina, M. Dolores et al. Jun. 30, 1995. "Transdermal nitroglycerin prevents nonsteroidal anti-inflammatory drug gastropathy." *European Journal of Pharmacology*, vol. 281. pp. R3-R4.

Elliott, Susan N., Webb McKnight, Giuseppe Cirino and John L. Wallace. 1995. "A Nitric Oxide-Releasing Nonsteroidal Anti-Inflammatory Drug Accelerates Gastric Ulcer Healing in Rats." *Gastroenterology*, vol. 109. pp. 524-530.

Wallace, John L., Webb McKnight, Piero Del Soldato, Anwar R. Baydoun and Giuseppe Cirino. Dec. 1995. "Anti-Thrombotic Effects of a Nitric Oxide-releasing, Gastric-sparing Aspirin Derivative." *J. Clin. Invest.*, vol. 96. pp. 2711-2718.

Cuzzolin, L. et al. 1995. "Anti-Inflammatory Potency and Gastrointestinal Toxicity of a New Compound, Nitronaproxen." *Pharmacological Research*, vol. 31, No. 1. pp. 61-65.

Langford, E. J., R. J. Wainwright and J. F. Martin. 1996. "Platelet Activation in Acute Myocardial Infarction and Unstable Angina Is Inhibited by Nitric Oxide Donors." *Arteriosclerosis, Thrombosis, and Vascular Biology*, vol. 16, No. 1. pp. 51-55.

Del Soldato, P. et al. 1996. "Nitric Oxide-Releasing NSAIDs, A Novel Class of Safe and Effective Anti-Inflammatory Agents." *Inflammopharmacology*, vol. 4. pp. 181-188.

Davies, N. M. et al. 1997. "NO-naproxen vs. naproxen: ulcerogenic, analgesic and anti-inflammatory effects." *Aliment Pharmacol. Ther.*, vol. 11. pp. 69-79.

Rautio, Jarkko et al. Dec. 1998. "In Vitro Evaluation of Acyloxyalkyl Esters as Dermal Prodrugs of Ketoprofen and Naproxen." *Journal of Pharmaceutical Sciences*, vol. 87, No. 12. pp. 1622-1628.

Endres, Stefan, Andreas Hacker, Eike Noack, Georg Kojda and Jochen Lehmann. 1999. "NO-Donors, part 3: nitrooxyacylated thiosalicylates and salicylates—synthesis and biological activities." *Eur. J. Med. Chem.*, vol. 34. pp. 895-901.

Rautio, Jarkko et al. 1999. "Synthesis and In Vitro Evaluation of Aminoacyloxyalkyl Esters of 2-(6-methoxy-2-naphthyl) propionic Acid as Novel Naproxen Prodrugs for Dermal Drug Delivery." *Pharmaceutical Research*, vol. 16, No. 8. pp. 1172-1178.

Muscará, Marcelo N., Webb McKnight, Samuel Asfaha & John L. Wallace. 2000. "Wound collagen deposition in rats: effects of an NO-NSAID and a selective COX-2 inhibitor." *British Journal of Pharmacology*, vol. 129. pp. 681-686.

Bing, Richard J., Tadahiko Yamamoto, Hyunjin Kim and Robert H. Grubbs. 2000. The Pharmacology of a New Nitric Oxide Donor: B-NOD. *Biochemical and Biophysical Research Communications*, vol. 275. pp. 350-353.

Al-Swayeh, O. A., R. H. Clifford, P. del Soldato and P. K. Moore. 2000. "A comparison of anti-inflammatory and anti-nociceptive activity of nitroaspirin and aspirin." *British Journal of Pharmacology*, vol. 129. pp. 343-350.

Johal, Kamaljit and Peter J. Hoffman. 2000. "Opposite effect of flurbiprofen and the nitroxybutyl ester of flurbiprofen on apoptosis in cultured guinea-pig gastric mucous cells." *British Journal of Pharmacology*, vol. 130. pp. 811-818.

Yamamoto, Tadahiko, N. Rani Kakar, Ernest R. Vina, Paul E. Johnson and Richard J. Bing. 2000. "The effect of aspirin and two nitric oxide donors on the infracted heart in situ." *Life Sciences*, vol. 67. pp. 839-846.

Abadi, Ashraf H., Stefan Laufer and Jochen Lehmann. 2001. "Synthesis and Cyclooxygenase Inhibitory Properties of Novel (+) 2-(6-Methoxy-2-naphthyl) propanoic Acid (Naproxene) Derivatives." *Arch. Pharm. Pharm. Med. Chem.*, vol. 334. pp. 104-106.

Gilmer, John F., Louise M. Moriarty, Dermot F. McCafferty and John M. Clancy. 2001. "Synthesis, hydrolysis kinetics and anti-platelet effects of isosorbide mononitrate derivatives of aspirin." *European Journal of Pharmaceutical Sciences*, vol. 14. pp. 221-227.

Kartasasmita, Rahmana E., Stefan Laufer and Jochen Lehmann. 2002. "NO-Donors (VII [1]): Synthesis and Cyclooxygenase Inhibitory Properties of N- and S-Nitrooxypivaloyl-cysteine Derivatives of Naproxen—A Novel Type of NO-NSAID." *Arch. Pharm. Pharm. Med. Chem.*, vol. 8. pp. 363-366.

Cena, Clara et al. 2003. "Antiinflammatory, Gastrosparing, and Antiplatlet Properties of New NO-Donor Esters of Aspirin." *J. Med. Chem.*, vol. 46. pp. 747-754.

Wallace, J. L. et al. "Nitric Oxide Releasing NSAID Derivatives: Anti-Inflammatory Without Gastropathy." *Gastroenterology*, vol. 106, No. 4., Part 2.

US 7,244,753 B2

CYCLOOXYGENASE-2 SELECTIVE INHIBITORS, COMPOSITIONS AND METHODS OF USE

RELATED APPLICATIONS

This application claims priority under 35 USC § 119(e) to U.S. Application Ser. No. 60/398,829 filed Jul. 29, 2002.

FIELD OF THE INVENTION

The invention describes novel nitrosated and/or nitrosylated cyclooxygenase 2(COX-2) selective inhibitors and novel compositions comprising at least one nitrosated and/or nitrosylated cyclooxygenase 2(COX-2) selective inhibitor, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one therapeutic agent. The invention also provides novel compositions comprising at least one COX-2 selective inhibitor, that is optionally nitrosated and/or nitrosylated, and at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The invention also provides novel kits comprising at least one COX-2 selective inhibitor, that is optionally nitrosated and/ or nitrosylated, and, optionally, at least one nitric oxide donor and/or at least one therapeutic agent. The invention also provides methods for treating inflammation, pain and fever; for treating gastrointestinal disorders and/or improving the gastrointestinal properties of COX-2 selective inhibitors; for facilitating wound healing; for treating and/or preventing renal and/or respiratory toxicities; for treating and/or preventing other disorders resulting from elevated levels of cyclooxygenase-2; and for improving the cardiovascular profile of COX-2 selective inhibitors.

BACKGROUND OF THE INVENTION

Nonsteroidal anti-inflammatory compounds (NSAIDs) are widely used for the treatment of pain, inflammation, and acute and chronic inflammatory disorders such as osteoarthritis and rheumatoid arthritis. These compounds inhibit the activity of the enzyme cyclooxygenase (COX), also known as prostaglandin G/H synthase, which is the enzyme that converts arachidonic acid into prostanoids. The NSAIDs also inhibit the production of other prostaglandins, especially prostaglandin $G_2$, prostaglandin $H_2$ and prostaglandin $E_2$, thereby reducing the prostaglandin-induced pain and swelling associated with the inflammation process. The chronic use of NSAIDs has been associated with adverse effects, such as gastrointestinal ulceration and renal toxicity. The undesirable side effects are also due to the inhibition of prostaglandin in the affected organ.

Recently two isoforms of cyclooxygenase, encoded by two distinct genes (Kujubu et al, *J. Biol. Chem.*, 266, 12866-12872 (1991)), have been identified—a constitutive form, cyclooxygenase-1(COX-1), and an inductive form, cyclooxygenase-2(COX-2). It is thought that the antiinflammatory effects of NSAIDs are mediated by the inhibition of COX-2, whereas the side effects seem to be caused by the inhibition of COX-1. The NSAIDs currently on the market either inhibit both isoforms of COX with little selectivity for either isoform or are COX-1 selective. Recently compounds that are COX-2 selective inhibitors have been developed and marketed. These COX-2 selective inhibitors have the desired therapeutic profile of an antiinflammatory drug without the adverse effects commonly associated with the inhibition of COX-1. However, these compounds can result in dyspepsia and can cause gastropathy (Mohammed et al, *N. Engl. J. Med.*, 340(25) 2005 (1999)). Additionally the COX-2 selective inhibitors can increase the risk of cardiovascular events in a patient (Mukherjee et al., *JAMA* 286(8) 954-959 (2001)); Hennan et al., *Circulation*, 104:820-825 (2001)).

There is still a need in the art for novel COX-2 selective inhibitor compounds that have gastroprotective properties, facilitate wound healing, decreased renal toxicity and dyspepsia, improved cardiovascular profile and that can be used at low dosages. The invention is directed to these, as well as other, important ends.

SUMMARY OF THE INVENTION

The invention provides novel COX-2 selective inhibitors, or a pharmaceutically acceptable salt thereof. These compounds are potent analgesics, have antiinflammatory properties and have an unexpected potential for facilitating wound healing. The novel compounds also have unexpected properties in the treatment and/or prevention of renal and/or respiratory toxicity and for improving the cardiovascular profile of COX-2 selective inhibitors. The COX-2 selective inhibitor, or a pharmaceutically acceptable salt thereof, can be nitrosated and/or nitrosylated through one or more sites, such as oxygen (hydroxyl condensation), sulfur (sulfhydryl condensation) and/or nitrogen. The invention also provides compositions comprising the novel compounds described herein in a pharmaceutically acceptable carrier.

The invention is also based on the discovery that administering at least one COX-2 selective inhibitor and at least one nitric oxide donor or administering at least one nitrosated and/or nitrosylated COX-2 selective inhibitor, and, optionally, at least one nitric oxide donor reduces the gastrointestinal toxicity induced by COX-2 selective inhibitors. Nitric oxide donors include, for example, S-nitrosothiols, nitrites, nitrates, N-oxo-N-nitrosamines, SPM 3672, SPM 5185, SPM 5186 and analogues thereof, and substrates of the various isozymes of nitric oxide synthase. Thus, another aspect of the invention provides compositions comprising at least one COX-2 selective inhibitor, that is optionally substituted with at least one NO and/or $NO_2$ group (i.e., nitrosylated and/or nitrosated), and at least one compound that donates, transfers or releases nitric oxide as a charged species, i.e., nitrosonium ($NO^+$) or nitroxyl (NO−), or as the neutral species, nitric oxide (NO.), and/or stimulates endogenous production of nitric oxide or EDRF in vivo and/or is a substrate for nitric oxide synthase. The invention also provides for such compositions in a pharmaceutically acceptable carrier.

Yet another aspect of the invention provides compositions comprising at least one COX-2 selective inhibitor, that is optionally substituted with at least one $NO_2$ group and/or at least one NO group (i.e., nitrosated and/or nitrosylated respectively), and, optionally, at least one compound that donates, transfers or releases nitric oxide as a charged species, i.e., nitrosonium ($NO^+$) or nitroxyl (NO−), or as the neutral species, nitric oxide (NO.), and/or stimulates endogenous production of nitric oxide or EDRF in vivo and/or is a substrate for nitric oxide synthase, and/or, optionally, at least one therapeutic agent, including but not limited to, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like. The invention also provides for such compositions in a pharmaceutically acceptable carrier.

Yet another aspect of the present invention provides methods for treating and/or preventing inflammation, pain and fever; for treating gastrointestinal disorders and/or improving gastrointestinal properties of COX-2 inhibitors; for facilitating wound healing; for treating and/or preventing renal and/or respiratory toxicity; and for treating and/or preventing COX-2 mediated disorders (i.e., disorders resulting from elevated levels of COX-2) in a patient in need thereof which comprises administering to the patient a therapeutically effective amount of at least one COX-2 selective inhibitor, that is optionally substituted with at least one $NO_2$ group and/or at least one NO group (i.e., nitrosated and/or nitrosylated respectively), and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase (i.e., NO donors). The methods can optionally further comprise the administration of at least one therapeutic agent, such as, for example, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures of two or more thereof. In this aspect of the invention, the methods can involve administering the COX-2 selective inhibitors, that are optionally nitrosated and/or nitrosylated, administering the COX-2 selective inhibitors, that are optionally nitrosated and/or nitrosylated and NO donors, administering the COX-2 selective inhibitors, that are optionally nitrosated and/or nitrosylated, and therapeutic agents, or administering the COX-2 selective inhibitors, that are optionally nitrosated and/or nitrosylated, NO donors and therapeutic agents. The selective COX-2 inhibitors, nitric oxide donors, and/or therapeutic agents can be administered separately or as components of the same composition in one or more pharmaceutically acceptable carriers.

Yet another aspect of the invention provides methods for improving the cardiovascular profile of COX-2 selective inhibitors in a patient in need thereof which comprises administering to the patient a therapeutically effective amount of at least one COX-2 selective inhibitor, optionally substituted with at least one $NO_2$ and/or NO group (i.e. nitrosated and/or nitrosylated), and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase (i.e. NO donor). The methods can optionally further comprise the administration of at least one of 3-hydroxy-3-methylglutaryl coenzyme A (HMG-CoA) inhibitors, antiplatelet agents, thrombin inhibitors, thromboxane inhibitors, and mixtures of two or more thereof. In this aspect of the invention, the methods can involve administering the nitrosated and/or nitrosylated COX-2 selective inhibitors, administering the COX-2 selective inhibitors, that are optionally nitrosated and/or nitrosylated, and NO donors, administering the COX-2 selective inhibitors, that are optionally nitrosated and/or nitrosylated, and at least one of 3-hydroxy-3-methylglutaryl coenzyme A (HMG-CoA) inhibitors, antiplatelet agents, thrombin inhibitors or thromboxane inhibitors, or administering the COX-2 selective inhibitors, that are optionally nitrosated and/or nitrosylated, NO donors, and at least one of 3-hydroxy-3-methylglutaryl coenzyme A (HMG-CoA) inhibitors, antiplatelet agents, thrombin inhibitors or thromboxane inhibitors. The COX-2 inhibitors, nitric oxide donors, and/or 3-hydroxy-3-methylglutaryl coenzyme A (HMG-CoA) inhibitors, antiplatelet agents, thrombin inhibitors or thromboxane inhibitors can be administered separately or as components of the same composition in one or more pharmaceutically acceptable carriers.

In yet another aspect the invention provides kits comprising at least one COX-2 selective inhibitor, that is optionally substituted with at least one $NO_2$ group and/or at least one NO group (i.e., nitrosated and/or nitrosylated respectively), and, optionally, at least one compound that donates, transfers or releases nitric oxide as a charged species, i.e., nitrosonium ($NO^+$) or nitroxyl ($NO-$), or as the neutral species, nitric oxide (NO.), and/or stimulates endogenous production of nitric oxide or EDRF in vivo and/or is a substrate for nitric oxide synthase. The kit can further comprise at least one therapeutic agent, such as, for example, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures of two or more thereof. The COX-2 selective inhibitor, the nitric oxide donor and/or therapeutic agent, can be separate components in the kit or can be in the form of a composition in the kit in one or more pharmaceutically acceptable carriers.

DETAILED DESCRIPTION OF THE INVENTION

As used throughout the disclosure, the following terms, unless otherwise indicated, shall be understood to have the following meanings.

"NSAID" refers to a nonsteroidal anti-inflammatory compound or a nonsteroidal antiinflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 $IC_{50}$ of less than about 2 μM and a cyclooxygenase-1 $IC_{50}$ of greater than about 5 µM, in the human whole blood COX-2 assay (as described in Brideau et al., *Inflamm Res.*, 45: 68-74 (1996)) and also has a selectivity ratio of cyclooxygenase-2 inhibition over cyclooxygenase-1 inhibition of at least 10, and preferably of at least 40. In another embodiment, the compound has a cyclooxygenase-1 $IC_{50}$ of greater than about 1 µM, and preferably of greater than 20 µM. The compound can also inhibit the enzyme, lipoxygenase. Such selectivity may indicate an ability to reduce the incidence of common NSAID-induced side effects.

"Parent COX-2 inhibitor" refers to a non-nitrosated and/or non-nitrosylated COX-2 inhibitor, or pharmaceutically acceptable salts thereof or pharmaceutically acceptable esters thereof. "Parent COX-2 inhibitor" includes the compounds of Formulas (I), (II) and (III) before they are nitrosated and/or nitrosylated by the methods described herein.

"Therapeutic agent" includes any therapeutic agent that can be used to treat or prevent the diseases described herein. "Therapeutic agents" include, for example, steroids, nonsteroidal antiinflammatory compounds, 5-lipoxygenase inhibitors, leukotriene $B_4$ receptor antagonists, leukotriene $A_4$ hydrolase inhibitors, 3-hydroxy-3-methylglutaryl coenzyme A inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like. Therapeutic agent includes the pro-drugs and pharmaceutical derivatives thereof including but not limited to the corresponding nitrosated and/or nitrosylated derivatives. Although nitric oxide donors have therapeutic activity, the term "therapeutic agent" does not include the nitric oxide donors described herein, since nitric oxide donors are separately defined.

"Cardiovascular disease or disorder" refers to any cardiovascular disease or disorder known in the art, including, but not limited to, restenosis, atherosclerosis, atherogenesis, angina, (particularly chronic, stable angina pectoris), ischemic disease, congestive heart failure or pulmonary edema associated with acute myocardial infarction, thrombosis, controlling blood pressure in hypertension (especially hypertension associated with cardiovascular surgical procedures), thromboembolic events, platelet aggregation, platelet adhesion, smooth muscle cell proliferation, vascular complications associated with the use of medical devices, wounds associated with the use of medical devices, cerebrovascular ischemic events, and the like. Complications associated with the use of medical devices may occur as a result of increased platelet deposition, activation, thrombus formation or consumption of platelets and coagulation proteins. Such complications, which are within the definition of "cardiovascular disease or disorder," include, for example, myocardial infarction, ischemic stroke, transient ischemic stroke, thromboembolic events, pulmonary thromboembolism, cerebral thromboembolism, thrombophlebitis, thrombocytopenia, bleeding disorders and/or any other complications which occur either directly or indirectly as a result of the foregoing disorders.

"Restenosis" is a cardiovascular disease or disorder that refers to the closure of a peripheral or coronary artery following trauma to the artery caused by an injury such as, for example, angioplasty, balloon dilation, atherectomy, laser ablation treatment or stent insertion. Restenosis can also occur following a number of invasive surgical techniques, such as, for example, transplant surgery, vein grafting, coronary artery bypass surgery, endarterectomy, heart transplantation, balloon angioplasty, atherectomy, laser ablation, endovascular stenting, and the like.

"Atheroslcerosis" is form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative, secreting substances such as growth factors, tissue-degradation enzymes and other proteins, which enable them to invade and spread into the inner vessel lining, blocking blood flow and making that vessel abnormally susceptible to being completely blocked by local blood clotting, resulting in the death of the tissue served by that artery. Atherosclerotic cardiovascular disease, coronary heart disease (also known as coronary artery disease or ischemic heart disease), cerebrovascular disease and peripheral vessel disease are all common manifestations of atherosclerosis and are therefore encompassed by the terms "atherosclerosis" and "atherosclerotic disease".

"Improving the cardiovascular profile" refers to and includes reducing the risk of thromboembolic events, reducing the risk of developing atherosclerosis and atherosclerotic diseases, and inhibiting platelet aggregation of the parent COX-2 inhibitor.

"Thromboembolic events" includes, but is not limited to, ischemic stroke, transient ischemic stroke, myocardial infarction, angina pectoris, thrombosis, thromboembolism, thrombotic occlusion and reocclusion, acute vascular events, restenosis, transient ischemic attacks, and first and subsequent thrombotic stroke. Patients who are at risk of developing thromboembolic events, may include those with a familial history of, or genetically predisposed to, thromboembolic disorders, who have had ischemic stroke, transient ischemic stroke, myocardial infarction, and those with unstable angina pectoris or chronic stable angina pectoris and patients with altered prostacyclin/thromboxane $A_2$ homeostasis or higher than normal thromboxane $A_2$ levels leading to increase risk for thromboembolism, including patients with diabetes and rheumatoid arthritis.

"Thromboxane inhibitor" refers to any compound that reversibly or irreversibly inhibits thromboxane synthesis, and includes compounds which are the so-called thromboxane $A_2$ receptor antagonists, thromboxane $A_2$ antagonists, thromboxane $A_2$/prostaglandin endoperoxide antagonists, thromboxane receptor (TP) antagonists, thromboxane antagonists, thromboxane synthase inhibitors, and dual acting thromboxane synthase inhibitors and thromboxane receptor antagonists. The characteristics of the preferred thromboxane inhibitor should include the suppression of thromboxane $A_2$ formation (thromboxane synthase inhibitors) and/or blockade of thromboxane $A_2$ and prostaglandin $H_2$ platelet and vessel wall (thromboxane receptor antagonists). The effects should block platelet activation and therefore platelet function.

"Thromboxane $A_2$ receptor antagonist" refers to any compound that reversibly or irreversibly blocks the activation of any thromboxane $A_2$ receptor.

"Thromboxane synthase inhibitor" refers to any compound that reversibly or irreversibly inhibits the enzyme thromboxane synthesis thereby reducing the formation of thromboxane $A_2$. Thromboxane synthase inhibitors may also increase the synthesis of antiaggregatory prostaglandins including prostacyclin and prostaglandin $D_2$. Thromboxane $A_2$ receptor antagonists and thromboxane synthase inhibitors and can be identified using the assays described in Tai, Methods of Enzymology, Vol. 86, 110-113 (1982); Hall, *Medicinal Research Reviews,* 11:503-579 (1991) and Coleman et al., *Pharmacol Rev.*, 46: 205-229 (1994) and references therein, the disclosures of which are incorporated herein by reference in its entirety.

"Dual acting thromboxane receptor antagonist and thromboxane synthase inhibitor" refers to any compound that simultaneously acts as a thromboxane A$_2$ receptor antagonist and a thromboxane synthase inhibitor.

"Thrombin inhibitors" refers to and includes compounds that inhibit hydrolytic activity of thrombin, including the catalytic conversion of fibrinogen to fibrin, activation of Factor V to Va, Factor VIII to VIIIa, Factor XIII to XIIIa and platelet activation. Thrombin inhibitors may be identified using assays described in Lewis et at., Thrombosis Research. 70: 173-190 (1993).

"Platelet aggregation" refers to the binding of one or more platelets to each other. Platelet aggregation is commonly referred to in the context of generalized atherosclerosis, not with respect to platelet adhesion on vasculature damaged as a result of physical injury during a medical procedure. Platelet aggregation requires platelet activation which depends on the interaction between the ligand and its specific platelet surface receptor.

"Platelet activation" refers either to the change in conformation (shape) of a cell, expression of cell surface proteins (e.g., the IIb/IIIa receptor complex, loss of GPIb surface protein), and secretion of platelet derived factors (e.g., serotonin, growth factors).

"Patient" refers to animals, preferably mammals, most preferably humans, and includes males and females, and children and adults.

"Therapeutically effective amount" refers to the amount of the compound and/or composition that is effective to achieve its intended purpose.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide (NO$^+$, NO$^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide (NO$^+$, NO$^-$, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, a hydroxyalkyl group, an alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more R$^{100}$ groups, wherein each R$^{100}$ is independently a hydroxy, an oxo, a carboxyl, a carboxamido, a halo, a cyano or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain C$_2$-C$_{10}$ hydrocarbon (preferably a C$_2$-C$_8$ hydrocarbon, more preferably a C$_2$-C$_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain C$_2$-C$_4$ hydrocarbon that can comprise one or two carbon-carbon double bonds.

"Substituted alkenyl" refers to a branched or straight chain C$_2$-C$_{10}$ hydrocarbon (preferably a C$_2$-C$_8$ hydrocarbon, more preferably a C$_2$-C$_6$ hydrocarbon) which can comprise one or more carbon-carbon double bonds, wherein one or more of the hydrogen atoms have been replaced with one or more R$^{100}$ groups, wherein each R$^{100}$ is independently a hydroxy, an oxo, a carboxyl, a carboxamido, a halo, a cyano or an amino group, as defined herein.

"Alkynyl" refers to an unsaturated acyclic C$_2$-C$_{10}$ hydrocarbon (preferably a C$_2$-C$_8$ hydrocarbon, more preferably a C$_2$-C$_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabycyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamido and nitro. Exemplary heterocyclic groups include pyrrolyl, furyl, thienyl, 3-pyrrolinyl, 4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$-$C_{10}$ hydrocarbon (preferably a $C_2$-$C_8$ hydrocarbon, more preferably a $C_2$-$C_6$ hydrocarbon) which can comprise one or more carbon-carbon triple bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetrahydroquinoline, and the like.

"Alkylheterocyclic ring" refers to a heterocyclic ring radical, as defined herein, attached to an alkyl radical, as defined herein. Exemplary alkylheterocyclic rings include 2-pyridylmethyl, 1-methylpiperidin-2-one-3-methyl, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O$—, wherein $R_{55}$ is an aryl group, as defined herein. Exemplary arylkoxy groups include napthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutuoxy, and the like.

"Hydroxy" refers to —OH.

"Oxo" refers to =O.

"Oxy" refers to —O⁻$R_{77}^+$ wherein $R_{77}$ is an organic or inorganic cation.

"Oxime" refers to =N—$OR_{81}$ wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone refers to =N—N($R_{81}$)($R'_{81}$) wherein $R'_{81}$ is independently selected from $R_{81}$, and $R_{81}$ is as defined herein.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Nitrate" refers to —O—$NO_2$.

"Nitrite" refers to —O—NO.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Amino" refers to —$NH_2$, an alkylamino group, a dialkylamino group, an arylamino group, a diarylamino group, an alkylarylamino group or a heterocyclic ring, as defined herein.

"Alkylamino" refers to $R_{50}$NH—, wherein $R_{50}$ is an alkyl group, as defined herein. Exemplary alkylamino groups include methylamino, ethylamino, butylamino, cyclohexylamino, and the like.

"Arylamino" refers to $R_{55}$NH—, wherein $R_{55}$ is an aryl group, as defined herein.

"Dialkylamino" refers to $R_{52}R_{53}$N—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}$N—, wherein $R_{55}$ and $R_{60}$ are each independently an aryl group, as defined herein.

"Alkylarylamino or arylalkylamino" refers to $R_{52}R_{55}$N—, wherein $R_{52}$ is an alkyl group, as defined herein, and $R_{55}$ is an aryl group, as defined herein.

"Alkylarylalkylamino" refers to $R_{52}R_{79}$N—, wherein $R_{52}$ is an alkyl group, as defined herein, and $R_{79}$ is an arylalkyl group, as defined herein.

"Alkylcycloalkylamino" refers to $R_{52}R_{80}$N—, wherein $R_{52}$ is an alkyl group, as defined herein, and $R_{80}$ is an cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, a arylamino group or an arylalkylamino group. Exemplary aminoaryl groups include anilino, N-methylanilino, N-benzylanilino, and the like.

"Thio" refers to —S—.

"Sulfinyl" refers to —S(O)—.

"Methanthial" refers to —C(S)—.

"Thial" refers to =S.

"Sulfonyl" refers to —S(O)$_2^-$.

"Sulfonic acid" refers to —S(O)$_2$O$R_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein "Sulfonic ester" refers to —S(O)$_2$O$R_{58}$, wherein $R_{58}$ is an alkyl group, an aryl group, or an aryl heterocyclic ring, as defined herein.

"Sulfonamido" refers to —S(O)$_2$—N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}$S—, wherein $R_{50}$ is an alkyl group, as defined herein (preferably a lower alkyl group, as defined herein).

"Arylthio" refers to $R_{55}$S—, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}$—S(O)—, wherein $R_{50}$ is an alkyl group, as defined herein.

"Alkylsulfonyl" refers to $R_{50}$—S(O)$_2$—, wherein $R_{50}$ is an alkyl group, as defined herein.

"Alkylsulfonyloxy" refers to $R_{50}$—S(O)$_2$—O—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—S(O)$_2$—, wherein $R_{55}$ is an aryl group, as defined herein.

"Arylsulfonyloxy" refers to $R_{55}$—S(O)$_2$—O—, wherein $R_{55}$ is an aryl group, as defined herein.

"Amidyl" refers to $R_{51}$C(O)N($R_{57}$)— wherein $R_{51}$ and $R_{57}$ are each independently a hydrogen atom, an alkyl group, an aryl group or an arylheterocyclic ring, as defined herein.

"Ester" refers to $R_{51}$C(O)O— wherein $R_{51}$ is a hydrogen atom, an alkyl group, an aryl group or an arylheterocyclic ring, as defined herein.

"Carbamoyl" refers to —O—C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)O$R_{76}$, wherein $R_{76}$ is a hydrogen, an organic cation or an inorganic cation, as defined herein.

Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$—$R_{52}$—C(O)—, wherein $R_{55}$ is an aryl group, as defined herein, and $R_{52}$ is an alkyl group, as defined herein.

"Alkylarylcarbonyl" refers to $R_{52}$—$R_{55}$—C(O)—, wherein $R_{55}$ is an aryl group, as defined herein, and $R_{52}$ is an alkyl group, as defined herein.

"Heterocyclicalkylcarbonyl" refer to $R_{78}$C(O)— wherein $R_{78}$ is a heterocyclicalkyl group, as defined herein.

"Carboxylic ester" refers to —C(O)$OR_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P($R_{70}$)($R_{71}$)($R_{72}$), wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

"Silyl" refers to —Si($R_{73}$)($R_{74}$)($R_{75}$), wherein $R_{73}$, $R_{74}$ and $R_{75}$ are each independently a covalent bond, a lower alkyl, an alkoxy, an aryl or an arylalkoxy, as defined herein.

Compounds that donate, transfer or release nitric oxide species in vivo have been recognized as having a wide spectrum of advantages and applications. The invention is based on the unexpected discovery of the effects of such compounds alone and together with one or more COX-2 inhibitors. Treatment or prevention of inflammation, pain and fever; treatment of gastrointestinal disorders and/or improvement of the gastrointestinal properties of COX-2 inhibitors; facilitation of wound healing; and treatment and/or prevention of renal and/or respiratory toxicity and cyclooxygenase-2 mediated disorders can be obtained by the use of COX-2 inhibitors of the invention; or by the use of COX-2 inhibitors in conjunction with one or more compounds that donate, release or transfer nitric oxide and/or stimulate endogenous production of NO and/or EDRF in vivo and/or is a substrate for nitric oxide synthase, and, optionally, with one or more therapeutic agents.

The COX-2 selective inhibitors, that are optionally nitrosated and/or nitrosylated, can be used alone or in conjunction with one or more compounds that donate, release or transfer nitric oxide and/or stimulate endogenous production of NO and/or EDRF in vivo and/or is a substrate for nitric oxide synthase, and/or with one or more therapeutic agents, such as for example, steroids, nonsterodal antiinflammatory compounds (NSAID), 5-lipoxygenase (5-LO) inhibitors, leukotriene $B_4$ (LTB$_4$) receptor antagonists, leukotriene $A_4$ (LTA$_4$) hydrolase inhibitors, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, analgesics, *Helicobacter pylori* inhibitors, proton pump inhibitors, isoprostane inhibitors, and mixtures of two or more thereof. These novel compounds and novel compositions of the present invention are described in more detail herein.

In one embodiment, the invention describes COX-2 inhibitors of Formula (I), and pharmaceutically acceptable salts thereof:

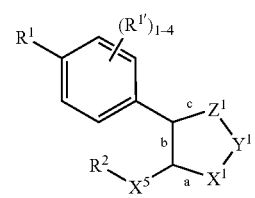

I wherein:
when side b is a double bond, and sides a and c are single bonds, —$X^1$—$Y^1$-$Z^1$- is:
(a) —$CR^4(R^5)$—$CR^5(R^{5'})$—$CR^4(R^5)$—;
(b) —C(O)—$CR^4(R^{4'})$—$CR^5(R^{5'})$—;
(c) —$CR^4(R^{4'})$—$CR^5(R^{5'})$—C(O)—;
(d) —$(CR^5(R^{5'}))_k$—O—C(O)—;
(e) —C(O)—O—$(CR^5(R^{5'}))_k$—;
(f) —$CR^4(R^{4'})$—$NR^3$—$CR^5(R^{5'})$—;
(g) —$CR^5(R^{5'})$—$NR^3$—C(O)—;
(h) —$CR^4$=$CR^{4'}$—S—;
(i) —S—$CR^4$=$CR^{4'}$—;
(j) —S—N=$CR^4$—;
(k) —$CR^4$=N—S—;
(l) —N=$CR^4$—O—;
(m) —O—$CR^4$=N—;
(n) —$NR^3$—$CR^4$=N—;
(o) —N=$CR^4$—S—;
(p) —S—$CR^4$=N—;
(q) —C(O)—$NR^3$—$CR^{5'}(R^{5'})$—;
(r) —$R^3N$—$CR^5$=C $R^{5'}$—;
(s) —$CR^4$=$CR^5$—$NR^3$—;
(t) —O—N=$CR^4$—;
(u) —$CR^4$=N—O—;
(v) —N=N—S—;
(w) —S—N=N—;
(x) —N=$CR^4$—$NR^3$—;
(y) —$R^3N$—N=N—;
(z) —N=N—$NR^3$—;
(aa) —$CR^4(R^{4'})$—O—$CR^5(R^{5'})$—;
(bb) —$CR^4(R^{4'})$—S—$CR^5(R^{5'})$—;
(cc) —$CR^4(R^{4'})$—C(O)—$CR^5(R^{5'})$—;
(dd) —$CR^4(R^{4'})$—$CR^5(R^{5'})$—C(S)—;
(ee) —$(CR^5(R^{5'}))_k$—O—C(S)—;
(ff) —C(S)—O—$(CR^5(R^{5'}))_k$—;

(gg) —(CR$^5$(R$^{5'}$))$_k$—NR$^3$—C(S)—;
(hh) —C(S)—NR$^3$—(CR$^5$(R$^{5'}$))$_k$—;
(ii) —(CR$^5$(R$^{5'}$))$_k$—S—C(O)—;
(jj) —C(O)—S—(CR$^5$(R$^{5'}$))$_k$—;
(kk) —O—CR$^4$=CR$^5$—;
(ll) —CR$^4$=CR$^5$—O—;
(mm) —C(O)—NR$^3$—S—;
(nn) —S—NR$^3$—C(O)—;
(oo) —C(O)—NR$^3$—O—;
(pp) —O—NR$^3$—C(O)—;
(qq) —NR$^3$—CR$^4$=CR$^5$—;
(rr) —CR$^4$=N—NR$^3$—;
(ss) —NR$^3$—N=CR$^4$—;
(tt) —C(O)—NR$^3$—NR$^3$—;
(uu) —NR$^3$—NR$^3$—C(O)—;
(vv) —C(O)—O—NR$^3$—;
(ww) —NR$^3$—O—C(O)—;
(xx) —O—CR$^4$R$^{4'}$—C(S)—;
(zz) —O—CR$^4$R$^{4'}$—C(O)—;
(aaa) —C(S)—CR$^4$R$^{4'}$—O—; or
(yy) —C(O)—CR$^4$R$^{4'}$—O—;
when sides a and c are double bonds and side b is a single bond, —X$^1$—Y$^1$-Z$^1$- is:
(a) =CR$^4$—O—CR$^5$=;
(b) =CR$^4$—NR$^3$—CR$^5$=;
(c) =N—S—CR$^4$=;
(d) =CR$^4$—S—N=;
(e) =N—O—CR$^4$=;
(f) =CR$^4$—O—N=;
(g) =N—S—N=;
(h) =N—O—N=;
(i) =N—NR$^3$—CR$^4$=;
(j) =CR$^4$—NR$^3$—N=;
(k) =N—NR$^3$—N=;
(l) =CR$^4$—S—CR$^5$=; or
(m) =CR$^4$—CR$^4$(R$^{4'}$)—CR$^5$=;
R$^1$ is:
(a) —S(O)$_2$—CH$_3$;
(b) —S(O)$_2$—NR$^8$(D$^1$);
(c) —S(O)$_2$—N(D$^1$)—C(O)—CF$_3$;
(d) —S(O)—(NH)—NH(D$^1$);
(e) —S(O)—(NH)—N(D$^1$)-C(O)—CF$_3$;
(f) —P(O)(CH$_3$)NH(D$^1$);
(g) —P(O)(CH$_3$)$_2$;
(h) —C(S)—NH(D$^1$);
(i) —S(O)(NH)CH$_3$;
(j) —P(O)(CH$_3$)OD$^1$; or
(k) —P(O)(CH$_3$)NH(D$^1$);
R$^{1'}$ at each occurrence is independently:
(a) hydrogen;
(b) halogen;
(c) methyl; or
(d) CH$_2$OH;
R$^2$ is:
(a) lower alkyl;
(b) cycloalkyl;
(c) mono-, di- or tri-substituted phenyl or naphthyl, wherein the substituents are each independently:
(1) hydrogen;
(2) halo;
(3) alkoxy;
(4) alkylthio;
(5) CN;
(6) haloalkyl, preferably CF$_3$;
(7) lower alkyl;
(8) N$_3$;
(9) —CO$_2$D$^1$;
(10) —CO$_2$-lower alkyl;
(11) —(C(R$^5$)(R$^6$))$_z$—OD$^1$;
(12) —(C(R$^5$)(R$^6$))$_z$—O-lower alkyl;
(13) lower alkyl-CO$_2$—R$^5$;
(14) —OD$^1$;
(15) haloalkoxy;
(16) amino;
(17) nitro;
(18) alkylsulfinyl; or
(19) heteroaryl;
(d) mono-, di- or tri-substituted heteroaryl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; wherein the substituents are each independently:
(1) hydrogen;
(2) halo;
(3) lower alkyl;
(4) alkoxy;
(5) alkylthio;
(6) CN;
(7) haloalkyl, preferably CF$_3$;
(8) N$_3$;
(9) —C(R$^5$)(R$^6$)—OD$^1$;
(10) —C(R$^5$)(R$^6$)—O-lower alkyl; or
(11) alkylsulfinyl;
(e) benzoheteroaryl which includes the benzo fused analogs of (d);
(f) —NR$^{10}$R$^{11}$;
(g) —SR$^{11}$;
(h) —OR$^{11}$;
(i) —R$^{11}$;
(j) alkenyl;
(k) alkynyl;
(l) unsubstituted, mono-, di-, tri- or tetra-substituted cycloalkenyl, wherein the substituents are each independently:
(1) halo;
(2) alkoxy;
(3) alkylthio;
(4) CN;
(5) haloalkyl, preferably CF$_3$;
(6) lower alkyl;
(7) N$_3$;
(8) —CO$_2$D$^1$;
(9) —CO$_2$-lower alkyl;
(10) —C(R$^{12}$)(R$^{13}$)—OD$^1$;
(11) —C(R$^{12}$)(R$^{13}$)—O-lower alkyl;
(12) lower alkyl-CO$_2$—R$^{12}$;
(13) benzyloxy;
(14) —O-(lower alkyl)-CO$_2$R$^{12}$;
(15) —O-(lower alkyl)-NR$^{12}$R$^{13}$; or
(16) alkylsulfinyl;
(m) mono-, di-, tri- or tetra-substituted heterocycloalkyl group of 5, 6 or 7 members, or a benzoheterocycle, wherein said heterocycloalkyl or benzoheterocycle contains 1 or 2 heteroatoms selected from O, S, or N and, optionally, contains a carbonyl group or a sulfonyl group, and wherein said substituents are each independently:
(1) halo;
(2) lower alkyl;
(3) alkoxy;
(4) alkylthio;

(5) CN;
(6) haloalkyl, preferably $CF_3$;
(7) $N_3$;
(8) —$C(R^{12})(R^{13})$—$OD^1$;
(9) —$C(R^{12})(R^{13})$—O-lower alkyl; or
(10) alkylsulfinyl;
(n) styryl, mono or di-substituted styryl, wherein the substituent are each independently:
  (1) halo;
  (2) alkoxy;
  (3) alkylthio;
  (4) CN;
  (5) haloalkyl, preferably $CF_3$;
  (6) lower alkyl;
  (7) $N_3$;
  (8) —$CO_2D^1$;
  (9) —$CO_2$-lower alkyl;
  (10) —$C(R^{12})(R^{13})$—$OD^1$;
  (11) —$C(R^{12})(R^{13})$—O-lower alkyl;
  (12) lower alkyl-$CO_2$—$R^{12}$;
  (13) benzyloxy;
  (14) —O-(lower alkyl)-$CO_2R^{12}$; or
  (15) —O-(lower alkyl)-$NR^{12}R^{13}$;
(o) phenylacetylene, mono- or di-substituted phenylacetylene, wherein the substituents are each independently:
  (1) halo;
  (2) alkoxy;
  (3) alkylthio;
  (4) CN;
  (5) haloalkyl, preferably $CF_3$;
  (6) lower alkyl;
  (7) $N_3$;
  (8) —$CO_2D^1$;
  (9) —$CO_2$-lower alkyl;
  (10) —$C(R^{12})(R^{13})$—$OD^1$;
  (11) —$C(R^{12})(R^{13})$—O-lower alkyl;
  (12) lower alkyl-$CO_2$—$R^{12}$;
  (13) benzyloxy;
  (14) —O-(lower alkyl)-$CO_2R^{12}$; or
  (15) —O-(lower alkyl)-$NR^{12}R^{13}$;
(p) fluoroalkenyl;
(q) mono- or di-substituted bicyclic heteroaryl of 8, 9 or 10 members, containing 2, 3, 4 or 5 heteroatoms, wherein at least one heteroatom resides on each ring of said bicyclic heteroaryl, said heteroatoms are each independently O, S and N and said substituents are each independently:
  (1) hydrogen;
  (2) halo;
  (3) lower alkyl;
  (4) alkoxy;
  (5) alkylthio;
  (6) CN;
  (7) haloalkyl, preferably $CF_3$;
  (8) $N_3$;
  (9) —$C(R^5)(R^6)$—$OD^1$; or
  (10) —$C(R^5)(R^6)$—O-lower alkyl;
(r) K;
(s) aryl;
(t) arylalkyl;
(u) cycloalkylalkyl;
(v) —$C(O)R^{11}$;
(u) hydrogen;
(v) arylalkenyl;
(w) arylalkoxy;
(x) alkoxy;
(y) aryloxy;
(z) cycloalkoxy;
(aa) arylthio;
(bb) alkylthio;
(cc) arylalkylthio; or
(dd) cycloalkylthio;
$R^3$ is:
(a) hydrogen;
(b) haloalkyl, preferably $CF_3$;
(c) CN;
(d) lower alkyl;
(e) —$(C(R_e)(R_f))_p$—U—V;
(f) K;
(g) unsubstituted or substituted:
  (1) lower alkyl-Q;
  (2) lower alkyl-O— lower alkyl-Q;
  (3) lower alkyl-S-lower alkyl-Q;
  (4) lower alkyl-O-Q;
  (5) lower alkyl-S-Q;
  (6) lower alkyl-O—V;
  (7) lower alkyl-S—V;
  (8) lower alkyl-O—K; or
  (9) lower alkyl-S—K;
wherein the substituent(s) reside on the lower alkyl group;
(h) Q;
(i) alkylcarbonyl;
(j) arylcarbonyl;
(k) alkylarylcarbonyl;
(l) arylalkylcarbonyl;
(m) carboxylic ester;
(n) carboxamido;
(o) cycloalkyl;
(p) mono-, di- or tri-substituted phenyl or naphthyl, wherein the substituents are each independently:
  (1) hydrogen;
  (2) halo;
  (3) alkoxy;
  (4) alkylthio;
  (5) CN;
  (6) haloalkyl, preferably $CF_3$;
  (7) lower alkyl;
  (8) $N_3$;
  (9) —$CO_2D^1$;
  (10) —$CO_2$-lower alkyl;
  (11) —$(C(R^5)(R^6))_z$—$OD^1$;
  (12) —$(C(R^5)(R^6))_z$—O-lower alkyl;
  (13) lower alkyl-$CO_2$—$R^5$;
  (14) —$OD^1$;
  (15) haloalkoxy;
  (16) amino;
  (17) nitro; or
  (18) alkylsulfinyl;
(q) alkenyl;
(r) alkynyl;
(s) arylalkyl;
(t) lower alkyl-$OD^1$;
(u) alkoxyalkyl;
(v) aminoalkyl;
(w) lower alkyl-$CO_2R^{10}$;
(x) lower alkyl-$C(O)NR^{10}(R^{10'})$;
(y) heterocyclicalkyl; or
(z) heterocyclic ring-C(O)—;
$R^4$, $R^{4'}$, $R^5$ and $R^{5'}$ are each independently:
(a) hydrogen;
(b) amino;
(c) CN;
(d) lower alkyl;

(e) haloalkyl;
(f) alkoxy;
(g) alkylthio;
(h) Q;
(i) —O-Q;
(j) —S-Q;
(k) K;
(l) cycloalkoxy;
(m) cycloalkylthio;
(n) unsubstituted, mono-, or di-substituted phenyl or unsubstituted, mono-, or disubstituted benzyl, wherein the substituents are each independently:
  (1) halo;
  (2) lower alkyl;
  (3) alkoxy;
  (4) alkylthio;
  (5) CN;
  (6) haloalkyl, preferably $CF_3$;
  (7) $N_3$;
  (8) Q;
  (9) nitro; or
  (10) amino;
(o) unsubstituted, mono-, or di-substituted heteroaryl or unsubstituted, mono-, or di-substituted heteroarylmethyl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; said substituents are each independently:
  (1) halo;
  (2) lower alkyl;
  (3) alkoxy;
  (4) alkylthio;
  (5) CN;
  (6) haloalkyl, preferably $CF_3$;
  (7) $N_3$;
  (8) —$C(R^6)(R^7)$—$OD^1$;
  (9) —$C(R^6)(R^7)$—O-lower alkyl; or
  (10) alkylsulfinyl
(p) —$CON(R^8)(R^8)$;
(q) —$CH_2OR^8$;
(r) —$CH_2OCN$;
(s) unsubstituted or substituted:
  (1) lower alkyl-Q;
  (2) —O-lower alkyl-Q;
  (3) —S-lower alkyl-Q;
  (4) lower alkyl-O-lower alkyl-Q;
  (5) lower alkyl-S-lower alkyl-Q;
  (6) lower alkyl-O-Q;
  (7) lower alkyl-S-Q;
  (8) lower alkyl-O—K;
  (9) lower alkyl-S—K;
  (10) lower alkyl-O—V; or
  (11) lower alkyl-S—V;
wherein the substituent(s) resides on the lower alkyl;
(t) cycloalkyl;
(u) aryl;
(v) arylalkyl;
(w) cycloalkylalkyl;
(x) aryloxy;
(y) arylalkoxy;
(z) arylalkylthio;
(aa) cycloalkylalkoxy;
(bb) heterocycloalkyl;
(cc) alkylsulfonyloxy;
(dd) alkylsulfonyl;
(ee) arylsulfonyl;
(ff) arylsulfonyloxy;
(gg) —$C(O)R^{10}$;
(hh) nitro;
(ii) amino;
(jj) aminoalkyl;
(kk) —C(O)-alkyl-heterocyclic ring;
(ll) halo;
(mm) heterocyclic ring;
(nn) —$CO_2D^1$;
(oo) carboxyl;
(pp) amidyl; or
(qq) alkoxyalkyl;
alternatively, $R^4$ and $R^5$ together with the carbons to which they are attached are:
  (a) cycloalkyl;
  (b) aryl; or
  (c) heterocyclic ring;
alternatively, $R^4$ and $R^{4'}$ or $R^5$ and $R^{5'}$ taken together with the carbon to which they are attached are:
  (a) cycloalkyl; or
  (b) heterocyclic ring;
alternatively, $R^4$ and $R^5$, $R^{4'}$ and $R^{5'}$, $R^4$ and $R^{5'}$, or $R^{4'}$ and $R^5$ when substituents on adjacent carbon atoms taken together with the carbons to which they are attached are:
  (a) cycloalkyl;
  (b) heterocyclic ring; or
  (c) aryl;
$R^6$ and $R^7$ are each independently:
  (a) hydrogen;
  (b) unsubstituted, mono- or di-substituted phenyl; unsubstituted, mono- or di-substituted benzyl; unsubstituted, mono- or di-substituted heteroaryl; mono- or di-substituted heteroarylmethyl, wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —$C(R^{14})(R^{15})$—$OD^1$; or
    (9) —$C(R^{14})(R^{15'})$—O-lower alkyl;
  (c) lower alkyl;
  (d) —$CH_2OR^8$;
  (e) CN;
  (f) —$CH_2CN$;
  (g) haloalkyl, preferably fluoroalkyl;
  (h) —$CON(R^8)(R^8)$;
  (i) halo; or
  (j) —$OR^8$;
$R^8$ is:
  (a) hydrogen;
  (b) K; or
  (c) $R^9$;
alternatively, $R^5$ and $R^{5'}$, $R^6$ and $R^7$ or $R^7$ and $R^8$ together with the carbon to which they are attached form a saturated monocyclic ring of 3, 4, 5, 6 or 7 atoms; optionally containing up to two heteroatoms selected from oxygen, $S(O)_o$ or $NR_i$;
$R^9$ is:
  (a) lower alkyl;
  (b) lower alkyl-$CO_2D^1$;
  (c) lower alkyl-$NHD^1$;

(d) phenyl or mono-, di- or tri-substituted phenyl, wherein the substituents are each independently:
  (1) halo;
  (2) lower alkyl;
  (3) alkoxy;
  (4) alkylthio;
  (5) lower alkyl-$CO_2D^1$;
  (6) lower alkyl-$NHD^1$;
  (7) CN;
  (8) $CO_2D^1$; or
  (9) haloalkyl, preferably fluoroalkyl;
(e) benzyl, mono-, di- or tri-substituted benzyl, wherein the substituents are each independently:
  (1) halo;
  (2) lower alkyl;
  (3) alkoxy;
  (4) alkylthio;
  (5) lower alkyl-$CO_2D^1$;
  (6) lower alkyl-$NHD^1$;
  (7) CN;
  (8) —$CO_2D^1$; or
  (9) haloalkyl, preferably $CF_3$;
(f) cycloalkyl;
(g) K; or
(h) benzoyl, mono-, di-, or trisubstituted benzoyl, wherein the substituents are each independently:
  (1) halo;
  (2) lower alkyl;
  (3) alkoxy;
  (4) alkylthio;
  (5) lower alkyl-$CO_2D^1$;
  (6) lower alkyl-$NHD^1$;
  (7) CN;
  (8) —$CO_2D^1$; or
  (9) haloalkyl, preferably $CF_3$;

$R^{10}$ and $R^{10\prime}$ are each independently:
  (a) hydrogen; or
  (b) $R^{11}$;

$R^{11}$ is:
  (a) lower alkyl;
  (b) cycloalkyl;
  (c) unsubstituted, mono-, di- or tri-substituted phenyl or naphthyl, wherein the substituents are each independently:
    (1) halo;
    (2) alkoxy;
    (3) alkylthio;
    (4) CN;
    (5) haloalkyl, preferably $CF_3$;
    (6) lower alkyl;
    (7) $N_3$;
    (8) —$CO_2D^1$;
    (9) —$CO_2$-lower alkyl;
    (10) —$C(R^{12})(R^{13})$—$OD^1$;
    (11) —$C(R^{12})(R^{13})$—O-lower alkyl;
    (12) lower alkyl-$CO_2D^1$;
    (13) lower alkyl-$CO_2R^{12}$;
    (14) benzyloxy;
    (15) —O-(lower alkyl)-$CO_2D^1$;
    (16) —O-(lower alkyl)-$CO_2R^{12}$; or
    (17) —O-(lower alkyl)-$NR^{12}R^{13}$;
  (d) unsubstituted, mono-, di- or tri-substituted heteroaryl, wherein the heteroaryl is a monocyclic aromatic ring of 5 atoms, said ring having one heteroatom which is S, O, or N, and, optionally, 1, 2, or 3 additional N atoms; or said heteroaryl is a monocyclic ring of 6 atoms, said ring having one heteroatom which is N, and, optionally 1, 2, or 3 additional N atoms, and wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —$C(R^{12})(R^{13})$—$OD^1$; or
    (9) —$C(R^{12})(R^{13})$—O-lower alkyl;
  (e) unsubstituted, mono- or di-substituted benzoheterocycle, wherein the benzoheterocycle is a 5, 6, or 7-membered ring which contains 1 or 2 heteroatoms independently selected from O, S, or N, and, optionally, a carbonyl group or a sulfonyl group, wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —$C(R^{12})(R^{13})$—$OD^1$; or
    (9) —$C(R^{12})(R^{13})$—O-lower alkyl;
  (f) unsubstituted, mono- or di-substituted benzocarbocycle, wherein the carbocycle is a 5, 6, or 7-membered ring which optionally contains a carbonyl group, wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —$C(R^{12})(R^{13})$—$OD^1$; or
    (9) —$C(R^{12})(R^{13})$—O-lower alkyl;
  (g) hydrogen; or
  (h) K $R^{12}$ and $R^{13}$ are each independently:
  (a) hydrogen;
  (b) lower alkyl; or
  (c) aryl; or
$R^{12}$ and $R^{13}$ together with the atom to which they are attached form a saturated monocyclic ring of 3, 4, 5, 6 or 7 atoms;

$R^{14}$ and $R^{15}$ are each independently:
  (a) hydrogen; or
  (b) lower alkyl; or
$R^{14}$ and $R^{15}$ together with the atom to which they are attached form a carbonyl, a thial, or a saturated monocyclic ring of 3, 4, 5, 6 or 7 atoms;

Q is:
  (a) —C(O)—U-$D^1$;
  (b) —$CO_2$-lower alkyl;
  (c) tetrazolyl-5-yl;
  (d) —$C(R^7)(R^8)$(S-$D^1$);
  (e) —$C(R^7)(R^8)$(O-$D^1$); or
  (f) —$C(R^7)(R^8)$(O-lower alkyl);

$X^5$ is:
  (a) —$(CR^{31}R^{32})_a$—;
  (b) —$(CR^{31}R^{32})_{bb}$-$A^1$;
  (c) -$A^1$-$(CR^{31}R^{32})_{bb}$—;

(d) —CR³¹R³²-A¹-CR³¹R³²—;
(e) —CR³¹═; or
(f) -A¹;
A¹ is:
(a) oxygen;
(b) thio;
(c) sulfinyl;
(d) sulfonyl; or
(e) —N(R³³)—;
R³¹ and R³² are each independently:
(a) hydrogen;
(b) lower alkyl;
(c) substituted lower alkyl;
(d) lower alkoxy;
(e) lower haloalkyl; or
(f) halo; or
R³¹ and R³² taken together are;
(a) oxo;
(b) thial;
(c) oxime; or
(d) hydrazone;
R³³ is:
(a) lower alkyl;
(b) hydrogen; or
(c) —C(O)H;
a is an integer equal to 1 or 3;
bb is an integer equal to 2 or 3;
D¹ is:
(a) hydrogen or
(b) D;
D is:
(a) V; or
(b) K;
U is:
(a) oxygen;
(b) sulfur; or
(c) —N($R_a$)($R_i$)—;
V is:
(a) —NO;
(b) —NO₂; or
(c) hydrogen
K is —$W_{aa}$-$E_b$-(C($R_e$)($R_f$))$_p$-$E_c$-(C($R_e$)($R_f$))$_x$-$W_d$-(C($R_e$)($R_f$))$_z$-U—V;

wherein aa, b, c, d, g, i and j are each independently an integer from 0 to 3;
p, x, y and z are each independently an integer from 0 to 10;
W at each occurrence is independently:
(a) —C(O)—;
(b) —C(S)—;
(c) -T-;
(d) —(C($R_e$)($R_f$))$_h$—;
(e) alkyl;
(f) aryl;
(g) heterocyclic ring;
(h) arylheterocyclic ring, or
(i) —(CH₂CH₂O)$_q$—;
E at each occurrence is independently a -T-group, an alkyl group, an aryl group, a heterocyclic ring, —(C($R_e$)($R_f$))$_h$—, an arylheterocyclic ring or —(CH₂CH₂O)$_q$—;
h is an integer form 1 to 10;
q is an integer from 1 to 5;
$R_e$ and $R_f$ are each independently a hydrogen, an alkyl, a cycloalkoxy, a halogen, a hydroxy, an hydroxyalkyl, an alkoxyalkyl, an arylheterocyclic ring. a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, -T-Q'-, or —(C($R_g$)($R_h$))$_k$-T-Q' or $R_e$ and $R_f$ taken together are an oxo, a thial, a heterocyclic ring, a cycloalkyl group, an oxime, a hydrazone or a bridged cycloalkyl group;
Q' is —NO or —NO₂;
k is an integer from 1 to 3;
T is independently a covalent bond, a carbonyl, an oxygen, —S(O)$_o$— or —N($R_a$)$R_i$—,
o is an integer from 0 to 2,
$R_a$ is a lone pair of electrons, a hydrogen or an alkyl group;
$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —OR'$_i$, —CH₂—C(T-Q')($R_g$)($R_h$), a bond to an adjacent atom creating a double bond to that atom or —(N₂O₂—)⁻.M⁺, wherein M⁺ is an organic or inorganic cation; with the proviso that when $R_i$ is —CH₂—C(T-Q')($R_g$)($R_h$) or —(N₂O₂—).M⁺; then "-T-Q'" can be a hydrogen, an alkyl group, an alkoxyalkyl group, an aminoalkyl group, a hydroxy group or an aryl group;
$R_g$ and $R_h$ at each occurrence are independently $R_e$;
R'$_i$ is independently selected from $R_i$.

In cases where $R_e$ and $R_f$ are a heterocyclic ring or $R_e$ and $R_f$ taken together with the carbon atom to which they are attached are a heterocyclic ring, then $R_i$ can be a substituent on any disubstituted nitrogen contained within the radical where $R_i$ is as defined herein.

In cases where multiple designations of variables that reside in sequence are chosen as a "covalent bond" or the integer chosen is 0, the intent is to denote a single covalent bond connecting one radical to another. For example, E₀ would denote a covalent bond, while E₂ denotes (E-E) and (C($R_e$)($R_f$))₂ denotes —C($R_e$)($R_f$)—C($R_e$)($R_f$)—.

Another embodiment of the invention describes compounds of Formula (II) and pharmaceutically acceptable salts thereof:

II

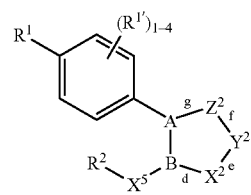

wherein:
A-B is:
  (a) N—C;
  (b) C—N; or
  (c) N—N;
when A-B is N—C, sides d and f are double bonds, and sides e and g are single bonds, —$X^2$—$Y^2$-$Z^2$- is:
  (a) =$CR^4$—$CR^{4'}$=$CR^5$—;
  (b) =N—$CR^4$=$CR^{4'}$;
  (c) =N—$CR^4$=N—;
  (d) =$CR^4$—N=$CR^{4'}$—;
  (e) =$CR^4$—N=N—;
  (f) =N—N=$CR^4$—;
  (g) =N—N=N—; or
  (h) =$CR^4$—$CR^5$=N—;
when A-B is C—N, sides e and g are double bonds, and sides d and f are single bonds, —$X^2$—$Y^2$-$Z^2$- is:
  (a) —$CR^4$=N—N=;
  (b) —N=N—$CR^4$=;
  (c) —$CR^4$=N—$CR^{4'}$=;
  (d) —N=$CR^4$—N=;
  (e) —$CR^4$=$CR^{4'}$—N=;
  (f) —N=$CR^4$—$CR^5$=;
  (g) —$CR^4$=$CR^5$—$CR^{5'}$=; or
  (h) —N=N—N=;
when A-B is C—N, side g is a double bond, and sides d, e and f are single bonds, —$X^2$—$Y^2$-$Z^2$- is:
  (a) —C(O)—O—$CR^4$=;
  (b) —C(O)—$NR^3$—$CR^4$=;
  (c) —C(O)—S—$CR^4$=; or
  (d) —C(H)$R^4$—C(OH)$R^5$—N=;
when A-B is N—C, sides d is a double bond, and sides e, f and g are single bonds, —$X^2$—$Y^2$-$Z^2$- is:
  (a) =$CR^4$—O—C(O)—;
  (b) =$CR^4$—$NR^3$—C(O)—;
  (c) =$CR^4$—S—C(O)—; or
  (d) =N—C(OH)$R^4$—C(H)$R^5$—;
when sides f is a double bond, and sides d, e and g are single bonds, —$X^2$—$Y^2$-$Z^2$- is:
  (a) —CH($R^4$)—$CR^5$=N—; or
  (b) —C(O)—$CR^4$=$CR^5$—;
when sides e is a double bond, and sides d, f and g are single bonds, —$X^2$—$Y^2$-$Z^2$- is:
  (a) —N=$CR^4$—CH($R^5$)—; or
  (b) —$CR^4$=$CR^5$—C(O)—;
when sides d, e, f and g are single bonds, —$X^2$—$Y^2$-$Z^2$- is:
  (a) —C(O)—$CR^4$($R^{4'}$)—C(O)—; and
with the proviso that when A-B is C—N, then $X^5$ must be —$(CR^{31}R^{32})_a$— or —$(CR^{31}R^{32})_{bb}$-$A^1$; and
wherein $R^1$, $R^{1'}$, $R^2$, $R^3$, $R^4$, $R^{4'}$, $R^5$, $R^{5'}$, $X^5$ $A^1$, $R^{31}$, $R^{32}$, a and bb are as defined herein Another embodiment of the invention describes compounds of Formula (III) and pharmaceutically acceptable salts thereof:

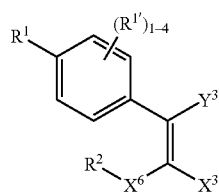

III wherein:
$X^3$ is:
  (a) —C(O)—U—$D^1$;
  (b) —$CH_2$—U—$D^1$;
  (c) —$CH_2$—C(O)—$CH_3$;
  (d) —$CH_2$—$CH_2$—C(O)—U—$D^1$;
  (e) —$CH_2$—O—$D^1$;
  (f) —C(O)H or
  (g) —C(O)—U—$R^{12}$;
$Y^3$ is:
  (a) —$(CR^5(R^{5'}))_k$—U—$D^1$;
  (b) —$CH_3$;
  (c) —$CH_2OC(O)R^6$; or
  (d) —C(O)H;
$R^{82}$, $R^{82'}$, $R^{83}$ and $R^{83'}$ are each independently:
  (a) hydrogen;
  (b) hydroxy;
  (c) alkyl;
  (d) alkoxy;
  (e) lower alkyl-$OD^1$;
  (f) alkylthio;
  (g) CN;
  (h) —C(O)$R^{84}$; or
  (i) —OC(O)$R^{85}$;
$R^{84}$ is:
  (a) hydrogen;
  (b) lower alkyl; or
  (c) alkoxy;
$R^{85}$ is:
  (a) lower alkyl;
  (b) alkoxy
  (c) unsubstituted, mono-, di- or tri-substituted phenyl or pyridyl, wherein the substituents are each independently:
    (1) halo;
    (2) alkoxy;
    (3) haloalkyl;
    (4) CN;
    (5) —C(O)$R^{84}$;
    (6) lower alkyl;
    (7) —S(O)$_o$-lower alkyl; or
    (8) —$OD^1$;
alternatively, $R^{82}$ and $R^{83}$ or $R^{82'}$ and $R^{83'}$ taken together are:
  (a) oxo;
  (b) thial;
  (c) =$CR^{86}R^{87}$; or
  (d) =$NR^{88}$;
$R^{86}$ and $R^{87}$ are each independently:
  (a) hydrogen;
  (b) lower alkyl;
  (c) lower alkyl-$OD^1$;
  (d) CN; or
  (e) —C(O)$R^{84}$;
$R^{88}$ is:
  (a) $OD^1$;
  (b) alkoxy;
  (c) lower alkyl; or
  (d) unsubstituted, mono-, di- or tri-substituted phenyl or pyridyl, wherein the substituents are each independently:
    (1) halo;
    (2) alkoxy;
    (3) haloalkyl;
    (4) CN;
    (5) —C(O)$R^{84}$;
    (6) lower alkyl;

(7) —S(O)$_o$-lower alkyl; or
(8) —OD$^1$;

X$^6$ is:
(a) —(CR$^{31}$R$^{32}$)$_a$—;
(b) —(CR$^{31}$R$^{32}$)$_{bb}$-A$^1$-; or
(e) —CR$^{31}$=; and wherein R$^1$, R$^{1'}$, R$^2$, R$^5$, R$^{5'}$, R$^6$, R$^{12}$, R31, R$^{32}$, A$^1$, U, D$^1$, a, bb, o and k are as defined herein.

Another embodiment of the invention describes compounds of Formula (IV) and pharmaceutically acceptable salts thereof:

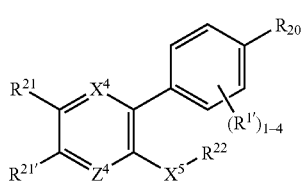

IV wherein:
X$^4$ and Z$^4$ are each independently:
(a) N; or
(b) CR$^{21}$;

R$^{20}$ is:
(a) —S(O)$_2$—CH$_3$;
(b) —S(O)$_2$—NR$^8$(D$^1$); or
(c) —S(O)$_2$—N(D$^1$)-C(O)—CF$_3$;

R$^{21}$ and R$^{21'}$ are each independently:
(a) hydrogen;
(b) lower alkyl;
(c) alkoxy;
(d) alkylthio;
(e) haloalkyl, preferably fluoroalkyl;
(f) haloalkoxy, preferably fluoroalkoxy;
(g) CN;
(h) —CO$_2$D$^1$;
(i) —CO$_2$R$^{14}$;
(j) lower alkyl-O-D$^1$;
(k) lower alkyl-CO$_2$D$^1$;
(l) lower alkyl-CO$_2$R$^{14}$;
(m) halo;
(n) —O-D$^1$;
(o) —N$_3$;
(p) —NO$_2$;
(q) —NR$^{14}$D$^1$;
(r) —N(D$^1$)C(O)R$^{14}$;
(s) —NHK;
(t) aryl;
(u) arylalkylthio;
(v) arylalkoxy;
(w) alkylamino;
(x) aryloxy;
(y) alkylarylalkylamino;
(z) cycloalkylalkylamino; or
(aa) cycloalkylalkoxy;

R$^{22}$ is:
(a) mono-, di- or tri-substituted phenyl or pyridinyl (or the N-oxide thereof), wherein the substituent are each independently:
(1) hydrogen;
(2) halo;
(3) alkoxy;
(4) alkylthio;
(5) CN;
(6) lower alkyl;
(7) haloalkyl, preferably fluoroalkyl;
(8) N$_3$;
(9) —CO$_2$D$^1$;
(10) —CO$_2$-lower alkyl;
(11) —C(R$^{14}$)(R$^{15}$)—OD$^1$;
(12) —OD$^1$;
(13) lower alkyl-CO$_2$—R$^{14}$; or
(14) lower alkyl-CO$_2$-D$^1$;
(b) -T-C(R$^{23}$)(R$^{24}$)—(C(R$^{25}$)(R$^{26}$))$_o$—C(R$^{27}$)(R$^{28}$)—U-D$^1$;

(c)

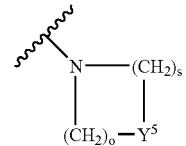

(d) arylalkyl; or
(e) cycloalkylalkyl;

wherein:
R$^{14}$ and R$^{15}$ are each independently:
(a) hydrogen; or
(b) lower alkyl;

R$^{23}$, R$^{24}$, R$^{25}$, R$^{26}$, R$^{27}$, R$^{28}$ are each independently:
(a) hydrogen; or
(b) lower alkyl; or
R$^{23}$ and R$^{27}$, or R$^{27}$ and R$^{28}$ together with the atoms to which they are attached form a carbocyclic ring of 3, 4, 5, 6 or 7 atoms, or R$^{23}$ and R$^{25}$ are joined to form a covalent bond;

Y$^5$ is:
(a) CR$^{29}$R$^{30}$;
(b) oxygen; or
(c) sulfur;

R$^{29}$ and R$^{30}$ are each independently:
(a) hydrogen;
(b) lower alkyl;
(c) (CH$_2$)$_o$—OD$^1$;
(d) halo; or
R$^{29}$ and R$^{30}$ taken together are an oxo group;
s is an integer from 2 to 4; and wherein R$^{1'}$, R$^8$, X$^5$, D$^1$, T, U, K and o are as defined herein.

Another embodiment of the invention describes compounds of Formula (V) and pharmaceutically acceptable salts thereof:

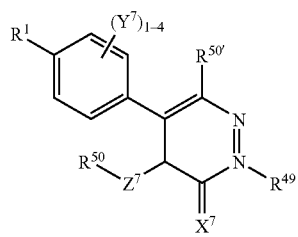

V wherein:
X$^7$ is:
(a) oxygen;
(b) sulfur;
(c) —NR$^{51}$;
(d) —N—O—R$^{52}$; or
(e) —N—NR$^{52}$R$^{52}$;
Y$^7$ at each occurrence is independently:
(a) hydrogen;
(b) halo;
(c) lower alkyl;
(d) alkenyl; or
(e) alkynyl;
Z$^7$ is:
(a) —(CR$^{31}$R$^{32}$)$_a$—;
R$^{49}$ is:
(a) R$^3$; or
(b) R$^4$;
R$^{50}$ and R$^{50'}$ are each independently:
(a) hydrogen;
(b) halo;
(c) lower alkyl;
(d) aryl;
(e) arylalkyl;
(f) cycloalkyl;
(g) cycloalkylalkyl;
(h) —OD$^1$;
(i) lower alkyl-OD$^1$;
(j) carboxamido;
(k) amidyl; or
(l) K;
R$^{51}$ is:
(a) lower alkyl;
(b) alkenyl;
(c) cycloalkyl;
(d) cycloalkylalkyl;
(e) aryl;
(f) arylalkyl;
(g) heterocyclic ring; or
(h) lower alkyl-heterocyclic ring;
R$^{52}$ and R$^{53}$ are each independently:
(a) lower alkyl;
(b) cycloalkyl;
(c) cycloalkylalkyl;
(d) aryl;
(e) arylalkyl;
(f) heterocyclic ring; or
(g) heterocyclicalkyl; and
wherein R$^1$, R$^3$, R$^4$, R$^{31}$, R$^{32}$, K, D$^1$ and a are as defined herein.

Another embodiment of the invention describes compounds of the Formula (VI) and pharmaceutically acceptable salts thereof:

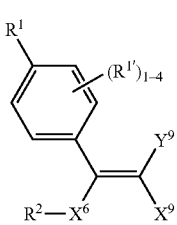

VI wherein:
X$^9$ is —C(O)—U-D$^1$ and Y$^9$ is —CH$_2$—CR$^5$(R$^{5'}$)—U-D$^1$; or
X$^9$ is —CH$_2$—CR$^5$(R$^{5'}$)—U-D$^1$ and Y$^9$ is —C(O)—U-D$^1$; or
X$^9$ and Y$^9$ taken together are:
(a) —C(O)—O—CR$^4$(R$^{4'}$)—CR$^5$(R$^{5'}$)—;
(b) —(CR$^4$(R$^{4'}$))$_k$—CR$^5$(R$^{5'}$)—CR$^5$(R$^{5'}$)—;
(c) —C(O)—(CR$^4$(R$^{4'}$))$_k$—CR$^5$(R$^{5'}$)—;
(d) —(CR$^4$(R$^{4'}$))$_k$—CR$^5$(R$^{5'}$)—C(O)—; or
(e) —C(O)—CR$^4$(R$^{4'}$)—CR$^5$(R$^{5'}$)—;

wherein X$^9$ is the first carbon atom of a, b, c, d and e; and wherein R$^1$, R$^{1'}$, R$^2$, R$^4$, R$^{4'}$, R$^5$, R$^{5'}$, X$^6$, U, D$^1$ and k are as defined herein.

Another embodiment of the invention describes compounds of the Formula (VII) and pharmaceutically acceptable salts thereof:

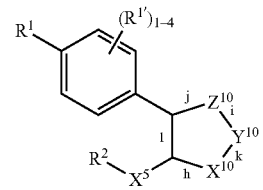

VII wherein:
when side h, k, and j are single bonds, and side i and l are a double bond, —X$^{10}$—Y$^{10}$-Z$^{10}$- is:

(a)

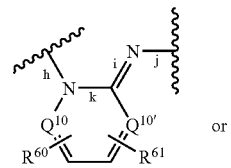

or (b)

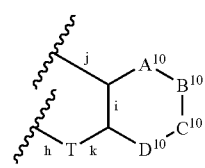

when sides i, k and l are single bonds, and sides h and j are double bonds, —X$^{10}$—Y$^{10}$-Z$^{10}$- is:

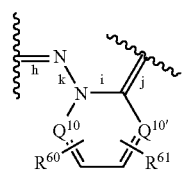

when side h and j are single bonds, l is a double bond, and side k and i is a single or a double bond, —X$^{10}$—Y$^{10}$-Z$^{10}$- is:

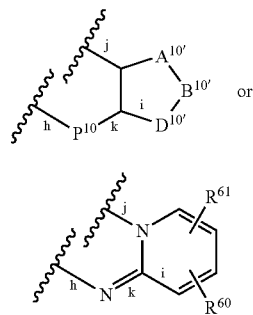

p¹⁰ is:
  (a) —N═;
  (b) —NR³—;
  (c) —O—; or
  (d) —S—;
Q¹⁰ and Q¹⁰' are each independently:
  (a) CR⁶⁰; or
  (b) nitrogen;
A¹⁰-B¹⁰-C¹⁰-D¹⁰- is:
  (a) —CR⁴═CR⁴'—CR⁵═CR⁵'—;
  (b) —CR⁴(R⁴')—CR⁵(R⁵')—CR⁴(R⁴')—C(O)—;
  (c) —CR⁴(R⁴')—CR⁵(R⁵')—C(O)—CR⁴(R⁴')—;
  (d) —CR⁴(R⁴')—C(O)—CR⁴(R⁴')—CR⁵(R⁵')—;
  (e) —C(O)—CR⁴(R⁴')—CR⁵(R⁵')—CR⁴(R⁴')—;
  (f) —CR⁴(R⁴')—CR⁵(R⁵')—C(O)—;
  (g) —CR⁴(R⁴')—C(O)—CR⁵(R⁵')—;
  (h) —C(O)—CR⁴(R⁴')—CR⁵(R⁵')—;
  (i) —CR⁴(R⁴')—CR⁵(R⁵')—O—C(O)—;
  (j) —CR⁴(R⁴')—O—C(O)—CR⁵(R⁵')—;
  (k) —O—C(O)—CR⁴(R⁴')—CR⁵(R⁵')—;
  (l) —CR⁴(R⁴')—CR⁵(R⁵')—C(O)—O—;
  (m) —CR⁴(R⁴')—C(O)—O—CR⁵(R⁵')—;
  (n) —C(O)—O—CR⁴(R⁴')—CR⁵(R⁵')—;
  (o) —CR¹²(R¹³)—O—C(O)—;
  (p) —C(O)—O—CR¹²(R¹³)—;
  (q) —O—C(O)—CR¹²(R¹³)—;
  (r) —CR¹²(R¹³)—C(O)—O—;
  (s) —N═CR⁴—CR⁴'═CR⁵—;
  (t) —CR⁴═N—CR⁴'═CR⁵—;
  (u) —CR⁴═CR⁴'—N═CR⁵—;
  (v) —CR⁴═CR⁵—CR⁵'═N—;
  (w) —N═CR⁴—CR⁴'═N—;
  (x) —N═CR⁴—N═CR⁴'—;
  (y) —CR⁴═N—CR⁴'═N—;
  (z) —S—CR⁴═N—;
  (aa) —S—N═CR⁴—;
  (bb) —N═N—NR³—;
  (cc) —CR⁴═N—S—;
  (dd) —N═CR⁴—S—;
  (ee) —O—CR⁴═N—;
  (ff) —O—N═CR⁴—; or
  (gg) —N═CR⁴—O—;
A¹⁰'-B¹⁰'-D¹⁰'- is:
  (a) —CR⁴═CR⁵—CR⁵'═
  (b) —CR⁴(R⁴')—CR⁵(R⁵')—CR⁴(R⁴')—;
  (c) —C(O)—CR⁴(R⁴')—CR⁵(R⁵')—;
  (d) —CR⁴(R⁴')—CR⁵(R⁵')—C(O)—;
  (e) —N═CR⁴—CR⁵═;
  (g) —N═N—CR⁴═;
  (h) —N═N—NR³—;
  (i) —N═N—N═;
  (j) —N═CR⁴—NR³—;
  (k) —N═CR⁴—N═;
  (l) —CR⁴═N—NR³—;
  (m) —CR⁴═N—N═;
  (n) —CR⁴═N—CR⁵═;
  (o) —CR⁴═CR⁵—NR³—;
  (p) —CR⁴═CR⁵—N═;
  (q) —S—CR⁴═CR⁵—;
  (r) —O—CR⁴═CR⁵;
  (s) —CR⁴═CR⁵—O—;
  (t) —CR⁴═CR⁵—S—;
  (u) —CR⁴═N—S—;
  (v) —CR⁴═N—O—;
  (w) —N═CR⁴—S—;
  (x) —N═CR⁴—O—;
  (y) —S—CR⁴═N—;
  (z) —O—CR⁴═N—;
  (aa) —N═N—S—;
  (bb) —N═N—O—;
  (cc) —S—N═N—;
  (dd) —O—N═N—;
  (ee) —CR⁴═CR⁵—S;
  (ff) —CR⁴(R⁴')—CR⁵(R⁵')—S—;
  (gg) —CR⁴(R⁴')—CR⁵(R⁵')—O—;
  (hh) —S—CR⁴(R⁴')—CR⁵(R⁵')—; or
  (ii) —O—CR⁴(R⁴')—CR⁵(R⁵')—;
R⁶⁰ and R⁶¹ are each independently:
  (a) lower alkyl;
  (b) haloalkyl, preferably fluoroalkyl;
  (c) alkoxy;
  (d) alkylthio;
  (e) lower alkyl-OD¹;
  (f) —C(O)H;
  (h) —(CH₂)_q—CO₂-lower alkyl;
  (i) —(CH₂)_q—CO₂D¹;
  (j) —O—(CH₂)_q—S-lower alkyl;
  (k) —(CH₂)_q—S-lower alkyl;
  (l) —S(O)₂-lower alkyl;
  (m) —(CH₂)_q—NR¹²R¹³; or
  (n) —C(O)N(R⁸)(R⁸); and
wherein R¹, R¹', R², R³, R⁴, R⁴', R⁵, R⁵', R⁸, R¹², R¹³, X⁵, T, D¹ and q are as defined herein.

Another embodiment of the invention describes compounds of the Formula (VIII) and pharmaceutically acceptable salts thereof:

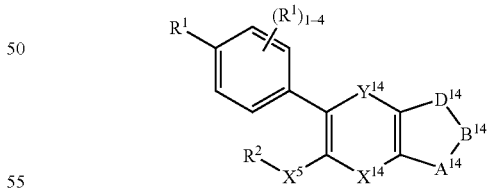

VIII wherein:
X¹⁴ is:
  (a) —C(O)—; or
  (b) —C(S)—;
Y¹⁴ is:
  (a) —O—; or
  (b) —S—;
A¹⁴-B¹⁴-D¹⁴- is:
  (a) —CR⁴═CR⁴'—CR⁵═CR⁵'—;
  (b) —CR⁴(R⁴')—CR⁵(R⁵')—C(O)—;

(c) —CR$^4$(R$^{4'}$)—C(O)—CR$^5$(R$^{5'}$)—;
(d) —C(O)—CR$^4$(R$^{4'}$)—CR$^5$(R$^{5'}$)—;
(e) —CR$^4$(R$^5$)—O—C(O)—;
(f) —C(O)—O—CR$^4$(R$^5$)—;
(g) —O—C(O)—CR$^4$(R$^5$)—;
(h) —S—N=CR$^4$—;
(i) —O—N=CR$^4$—;
(j) —CR$^4$(R$^5$)—NR$^3$—C(O)—;
(k) —C(O)—NR$^3$—CR$^4$(R$^5$)—;
(l) —NR$^3$—C(O)—CR$^4$(R$^5$)—;
(m) —CR$^4$(R$^5$)—S—C(O)—;
(n) —C(O)—S—CR$^4$(R$^5$)—;
(o) —S—C(O)—CR$^4$(R$^5$)—;
(p) —CR$^4$=CR$^{4'}$—C(O)—;
(q) —C(O)—CR$^4$=CR$^{4'}$—;
(r) —O—CR$^4$=CR$^{4'}$—;
(s) —S—CR$^4$=CR$^{4'}$—;
(t) —NR$^3$—CR$^4$=CR$^5$—;
(u) —S—NR$^3$—C(O)—;
(v) —O—NR$^3$—C(O)—; or
(w) —NR$^3$—N=CR$^4$—; and wherein R$^1$, R$^{1'}$, R$^2$, R$^3$, R$^4$, R$^{4'}$, R$^5$, R$^{5'}$ and X$^5$ are as defined herein.

In another embodiment of the invention describes compounds of Formulas (I), (II), (III), (IV), (V), (VI), (VII) and (VIII), and pharmaceutically acceptable salts thereof, that each must contain at least one NO and/or NO$_2$ group (i.e., nitrosylated and/or nitrosated) wherein the one NO and/or NO$_2$ group is linked to the compounds of Formula (I) to (VIII) through one or more sites, such as oxygen (hydroxyl condensation), sulfur (sulfhydryl condensation) and/or nitrogen.

Another embodiment of the invention describes the metabolites of the compounds of Formulas (I), (II), (III), (IV), (V), (VI), (VII) and (VIII), and pharmaceutically acceptable salts thereof. These metabolites, include but are not limited to, the non-nitrosated and/or normitrosylated derivatives, degradation products, hydrolysis products, and the like, of the compounds of Formulas (I), (II), (III), (IV), (V), (VI), (VII), and (VIII), and pharmaceutically acceptable salts thereof.

In other embodiments of the invention, the COX-2 selective inhibitors of Formula II are:

1-(1-(cyclohexylmethyl)-3-(hydroxymethyl)pyrazol-5-yl)-4-(methylsulfonyl)benzene;
4-(1-(cyclohexylmethyl)-3-((2-hydroxyethoxy)methyl) pyrazol-5-yl)-1-(methylsulfonyl)benzene;
1-(3-(hydroxymethyl)-1-benzylpyrazol-5-yl)-4-(methylsulfonyl)benzene;
1-(3-((1E)-3-Hydroxyprop-1-enyl)-1-(cyclohexylmethyl) pyrazol-5-yl)-4-(methylsulfonyl) benzene;
1-(1-(cyclohexylmethyl)-3-(3-hydroxypropyl)pyrazol-5-yl)-4-(methylsulfonyl)benzene;
1-(1-(cyclohexylmethyl)-3-vinylpyrazol-5-yl)-4-(methylsulfonyl)benzene;
methyl (2E)-3-(1-(cyclohexylmethyl)-5-(4-(methylsulfonyl) phenyl)pyrazol-3-yl) prop-2-enoate;
methyl 5-(4-(methylsulfonyl)phenyl)-1-benzylpyrazole-3-carboxylate; and pharmaceutically acceptable salts thereof.

In other embodiments of the invention, the nitrosated COX-2 selective inhibitors of Formula II are:

1-(1-(cyclohexylmethyl)-3-((nitrooxy)methyl)pyrazol-5-yl)-4-(methylsulfonyl)benzene;
4-(1-(cyclohexylmethyl)-3-((2-nitrooxy)ethoxy)methyl) pyrazol-5-yl)-1-(methylsulfonyl) benzene;
4-(methylsulfonyl)-1-(3-((nitrooxyl)methyl)-1-benzylpyrazol-5-yl)benzene;
1-(3-((1E)-3-nitrooxyprop-1-enyl)-1-(cyclohexylmethyl) pyrazol-5-yl)-4-(methylsulfonyl) benzene;
1-(1-(cyclohexylmethyl)-3-(3-(nitrooxy)propyl)pyrazol-5-yl)-4-(methylsulfonyl) benzene; and pharmaceutically acceptable salts thereof.

In other embodiments of the invention, the COX-2 selective inhibitors of Formula IV are:

3-(4-(methylsulfonyl)phenyl)-5-(trifluoromethyl)(2-pyridyl) phenyl ketone;
2-(3-(4-(methylsulfonyl)phenyl)-5-(trifluoromethyl)(2-pyridyl))-2-phenylethanenitrile;
3-fluorophenyl 2-(4-methylsulfonylphenyl)(3-pyridyl) ketone;
2-(4-(methylsulfonyl)phenyl)(3-pyridyl) 2-pyridyl ketone;
ethyl 3-((2-(4-(methylsulfonyl)phenyl)-3-pyridyl)carbonyl) benzoate; and pharmaceutically acceptable salts thereof.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. The invention includes within its scope all such isomers and mixtures thereof.

Another embodiment of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The intermediates for the compounds of Formulas (I), (II), (III), (IV), (V), (VI), (VII) and (VIII) can be synthesized by one skilled in the art following the methods and examples described herein. The synthesis of the intermediates for the COX-2 inhibitors (i.e. non-nitrosated and/or non-nitrosylated COX-2 inhibitors) are disclosed in, for example, U.S. Pat. Nos. 5,344,991, 5,393,790, 5,466,823, 5,474,995, 5,486,534, 5,504,215, 5,508,426, 5,510,496, 5,516,907, 5,521,207, 5,536,752, 5,550,142, 5,563,165, 5,616,601, 5,620,999, 5,677,318, 5,668,161, 5,691,374, 5,698,584, 5,710,140, 5,753,688, 5,859,257, 5,908,858, 5,945,539, 5,994,381, 6,080,876, 6,083,969 and 6,071,954 and in WO 91/19708, WO 94/15932, WO 94/26731, WO 94/27980, WO 95/00501, WO 95/11883, WO 95/15315, WO 95/15316, WO 95/15317, WO 95/15318, WO 95/18799, WO 95/21817, WO 95/30652, WO 96/30656, WO 96/03387, WO 96/03392, WO 96/03385, WO 96/03387, WO 96/03388, WO 96/09293, WO 96/09304, WO 96/16934, WO 96/19462, WO 96/19463, WO 96/19469, WO 96/25405, WO 96/36617, WO 96/36623, WO 97/11704, WO 97/13755, WO 97/27181, WO 97/14691, WO 97/16435, WO 97/34882, WO 97/36863, WO 97/40012, WO 97/45420, WO 98/00416, WO 98/11080, WO 98/22422, WO 98/41516, WO 98/46594, WO 98/52937, WO 99/15531, WO 99/23087, WO 99/33796, WO 99/25695, WO 99/61016, WO 99/62884 and WO 99/64415 and in EP 0 745 596 A1, EP0 087 629 B1, EP0 418 845 B1, EP0 554 829 A2, EP0 863 134 A1, EP 1 006 114 A1 for the intermediate of Formulas (I) and (II); and in U.S. Pat. Nos. 5,733,909, 5,789,413 and 5,849,943 and in WO 96/13483, WO 97/28120 and WO 97/28121 for the intermediates of Formula (III); and in U.S. Pat. No. 5,861,419 and 6,001,843 and in WO 96/10012, WO 96/16934, WO 96/24585, WO 98/03484, WO 98/24584, WO 98/47871, WO 99/14194 and WO 99/14195 for the intermediates of Formula (IV); and in WO 98/41511, WO 99/10331, WO 99/10332 and WO 00/24719 for the intermediates of Formula (V); and in U.S. Pat. No. 5,807,873 and WO 98/43966 for the intermediates of Formula (VI); and in U.S. Pat. Nos. 5,521,213 and 5,552,422 and in WO 96/06840, WO 96/21667, WO 96/31509, WO 99/12930, WO 00/08024 and WO 00/26216 for the intermediates of Formula (VII); and in WO 00/10993 for the intermediates of Formula (XIV); and in WO 98/32732 for the intermediates of Formula (VII); the disclosures of each of which are incorporated by reference herein in their entirety. The COX-2 inhibitor compounds can then be nitrosated and/or nitrosylated through one or more sites such as oxygen, sulfur and/or nitrogen using the methods described in the examples herein and using conventional methods known to one skilled in the art. For example, known methods for nitrosating and/or nitrosylating compounds are described in U.S. Pat. Nos. 5,380,758 and 5,703,073; WO 94/03421, WO 94/04484, WO 94/12463, WO 95/09831, WO 95/30641, WO 97/27749, WO 98/19672, WO 00/25776, WO 01/00563 and WO 01/04082, WO 01/10814, WO 01/45703 and Oae et al, *Org. Prep. Proc. Int.,* 15(3):165-198 (1983), the disclosures of each of which are incorporated by reference herein in their entirety. The methods of nitrosating and/or nitrosylating the compounds described in the examples herein and in these references can be applied by one skilled in the art to produce any of the nitrosated and/or nitrosylated COX-2 inhibitors described herein.

The compounds of the invention include the COX-2 inhibitors, which have been nitrosated and/or nitrosylated through one or more sites such as oxygen (hydroxyl condensation), sulfur (sulfhydryl condensation) and/or nitrogen. The nitrosated and/or nitrosylated COX-2 inhibitors of the invention donate, transfer or release a biologically active form of nitrogen monoxide (i.e., nitric oxide).

Nitrogen monoxide can exist in three forms: NO– (nitroxyl), NO. (uncharged nitric oxide) and NO$^+$ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium (NO$^+$) does not react with $O_2$ or $O_2^-$ species, and functionalities capable of transferring and/or releasing NO$^+$ and NO– are also resistant to decomposition in the presence of many redox metals. Consequently, administration of charged NO equivalents (positive and/or negative) is a more effective means of delivering a biologically active NO to the desired site of action.

Compounds contemplated for use in the invention, e.g., COX-2 selective inhibitor, that can be optionally nitrosated and/or nitrosylated, through one or more sites such as oxygen (hydroxyl condensation), sulfur (sulfhydryl condensation) and/or nitrogen, are, optionally, used in combination with nitric oxide and compounds that release nitric oxide or otherwise directly or indirectly deliver or transfer a biologically active form of nitrogen monoxide to a site of its intended activity, such as on a cell membrane in vivo.

The term "nitric oxide" encompasses uncharged nitric oxide (NO.) and charged nitrogen monoxide species, preferably charged nitrogen monoxide species, such as nitrosonium ion (NO$^+$) and nitroxyl ion (NO–). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z, 3E)-4-ethyl-2-(hydroxyimino)-6-methyl-5-nitro-3-heptenyl)-3-pyridinecarboxamide (FR 146801), nitrosoamines, furoxans as well as substrates for the endogenous enzymes which synthesize nitric oxide. NONOates include, but are not limited to, (Z)-1-(N-methyl-N-(6-(N-methyl-ammonio-hexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino) diazen-1-ium-1,2-diolate (spermine NONOate or "SPER/NO") and sodium(Z)-1-(N,N-diethylamino)diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165-198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; or (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring. a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, -T-Q'-, or $-(C(R_g)(R_h))_k$-T-Q' or $R_e$ and $R_f$ taken together are an oxo, a methanthial, a heterocyclic ring, a cycloalkyl group, an oxime, a hydrazone or a bridged cycloalkyl group; Q' is —NO or —$NO_2$; and T is independently a covalent bond, a carbonyl, an oxygen, —$S(O)_o$— or —$N(R_a)R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —$CH_2$—C(T-Q')($R_g$)($R_h$), or —($N_2O_2$—)$^-$.$M^+$, wherein $M^+$ is an organic or inorganic cation; with the proviso that when $R_i$ is —$CH_2$—C(T-Q')($R_g$)($R_h$) or —($N_2O_2$—).$M^+$; then "-T-Q'" can be a hydrogen, an alkyl group, an alkoxyalkyl group, an aminoalkyl group, a hydroxy group or an aryl group; and $R_g$ and $R_h$ at each occurrence are independently $R_e$.

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—O— or ON—N— group. The compounds that include at least one ON—O— or ON—N— group are preferably ON—O— or ON—N-polypeptides (the term "polypeptide" includes proteins and polyamino acids that do not possess an ascertained biological function, and derivatives thereof); ON—O— or ON—N-amino acids (including natural and synthetic amino acids and their stereoisomers and racemic mixtures); ON—O— or ON—N-sugars; ON—O— or —ON—N— modified or unmodified oligonucleotides (comprising at least 5 nucleotides, preferably 5-200 nucleotides); ON—O— or ON—N— straight or branched, saturated or unsaturated, aliphatic or aromatic, substituted or unsubstituted hydrocarbons; and ON—O—, ON—N— or ON—C-heterocyclic compounds.

Another group of NO adducts for use in the invention include nitrates that donate, transfer or release nitric oxide, such as compounds comprising at least one $O_2N$—O—, $O_2N$—N— or $O_2N$—S— group. Preferred among these compounds are $O_2N$—O—, $O_2N$—N— or $O_2N$—S— polypeptides (the term "polypeptide" includes proteins and also polyamino acids that do not possess an ascertained biological function, and derivatives thereof); $O_2N$—O—, $O_2N$—N— or $O_2N$—S—amino acids (including natural and synthetic amino acids and their stereoisomers and racemic mixtures); $O_2N$—O—, $O_2N$—N— or $O_2N$—S— sugars; $O_2N$—O—, $O_2N$—N— or $O_2N$—S— modified and unmodified oligonucleotides (comprising at least 5 nucleotides, preferably 5-200 nucleotides); $O_2N$—O—, $O_2N$—N— or $O_2N$—S— straight or branched, saturated or unsaturated, aliphatic or aromatic, substituted or unsubstituted hydrocarbons; and $O_2N$—O—, $O_2N$—N— or $O_2N$—S— heterocyclic compounds. Preferred examples of compounds comprising at least one $O_2N$—O—, $O_2N$—N— or $O_2N$—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284,872, 5,428,061, 5,661,129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: $R^{1''}R^{2''}N$—$N(O-M^+)$-NO, where $R^{1''}$ and R$^{2''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where M$^+$ is an organic or inorganic cation, such as, for example, an alkyl substituted ammonium cation or a Group I metal cation.

The invention is also directed to compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, omithine, glutamine, lysine, polypeptides comprising at least one of these amino acids, inhibitors of the enzyme arginase (e.g., N-hydroxy-L-arginine and 2(S)-amino-6-boronohexanoic acid), nitric oxide mediators and/or physiologically acceptable salts thereof, including, for example, pyruvate, pyruvate precursors, α-keto acids having four or more carbon atoms, precursors of α-keto acids having four or more carbon atoms (as disclosed in WO 03/017996, the disclosure of which is incorporated herein in its entirety), and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524-526 (1987); Ignarro et al, *Proc. Natl. Acad. Sci. USA*, 84:9265-9269 (1987)).

The invention is also based on the discovery that compounds and compositions of the invention may be used in conjunction with other therapeutic agents for co-therapies, partially or completely, in place of other conventional anti-inflammatory compounds, such as, for example, together with steroids, NSA/Ds, 5-lipoxygenase (5-LO) inhibitors, leukotriene B$_4$ (LTB$_4$) receptor antagonists, leukotriene A$_4$ (LTA$_4$) hydrolase inhibitors, 5-HT agonists, HMG-CoA inhibitors, H$_2$ receptor antagonists, antineoplastic agents, antiplatelet agents, thrombin inhibitors, thromboxane inhibitors, decongestants, diuretics, sedating or non-sedating antihistamines, inducible nitric oxide synthase inhibitors, opiods, analgesics, *Helicobacter pylori* inhibitors, proton pump inhibitors, isoprostane inhibitors, and mixtures of two or more thereof.

Leukotriene A$_4$ (LTA$_4$) hydrolase inhibitors refer to compounds that selectively inhibit leukotriene A$_4$ hydrolase with an IC$_{50}$ of less than about 10 μM, and preferably with an IC$_{50}$ of less than about 1 μM. Suitable LTA$_4$ hydrolase inhibitors include, but are not limited to, RP-64966, (S,S)-3-amino-4-(4-benzyloxyphenyl)-2-hydroxybutyric acid benzyl ester, N-(2(R)-(cyclohexylmethyl)-3-(hydroxycarbamoyl)propionyl)-L-alanine, 7-(4-(4-ureidobenzyl)phenyl) heptanoic acid and 3 (3-(1E,3E-tetradecadienyl)-2-oxiranyl) benzoic acid lithium salt, and mixtures of two or more thereof.

Suitable LTB$_4$ receptor antagonists include, but are not limited to, ebselen, linazolast, ontazolast; WAY 121006; Bay-x-1005; BI-RM-270; CGS-25019C; ETH-615; MAFP; TMK-688; T-0757; LY 213024, LY 210073, LY 223982, LY 233469, LY 255283, LY 264086, LY 292728 and LY 293111; ONO-LB457, ONO-4057, and ONO-LB-448, S-2474, calcitrol; PF 10042; Pfizer 105696; RP 66153; SC-53228, SC-41930, SC-50605, SC-51146 and SC-53228; SB-201146 and SB-209247; SKF-104493; SM 15178; TMK-688; BPC 15, and mixtures of two or more thereof. The preferred LTB$_4$ receptor antagonists are calcitrol, ebselen, Bay-x-1005, CGS-25019C, ETH-615, LY-293111, ONO-4057 and TMK-688, and mixtures of two or more thereof.

Suitable 5-LO inhibitors include, but are not limited to, A-76745, 78773 and ABT761; Bay-x-1005; CMI-392; E-3040; EF-40; F-1322; ML-3000; PF-5901; R-840; rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast, and mixtures of two or more thereof. Suitable 5-LO inhibitors are also described more fully in WO 97/29776, the disclosure of which is incorporated herein by reference in its entirety.

Suitable 5-HT agonists, include, but are not limited to, rizatriptan, sumatriptan, naratriptan, zoimitroptan, eieptriptan, aimotriptan, ergot alkaloids. ALX 1323, Merck L 741604 SB 220453 and LAS 31416. Suitable 5-HT agonists are described more fully in WO 0025779, and in WO 00/48583. 5-HT agonists refers to a compound that is an agonist to any 5-HT receptor, including but not limited to, 5-HT$_1$ agonists, 5-HT$_{1B}$ agonists and 5-HT$_{1D}$ agonists, and the like.

Suitable steroids, include, but are not limited to, budesonide, dexamethasone, corticosterone, prednisolone, and the like. Suitable steroids are described more fully in the literature, such as in the Merck Index on CD-ROM, 13$^{th}$ Edition.

Suitable HMG CoA inhibitors, include, but are not limited to, reductase and synthase inhibitors, such as, for example, squalene synthetase inhibitors, benzodiazepine squalene synthase inhibitors, squalene epoxidase inhibitors, acyl-coenzyme A, bile acid sequestrants, cholesterol absorption inhibitors, and the like. Suitable HMG CoA inhibitors include simvastatin, pravastatin, lovastatin, mevastatin, fluvastatin, atorvastatin, cerivastatin, and the like, and are described more fully in U.S. Pat. No. 6,245,797 and WO 99/20110, the disclosures of which are incorporated herein by reference in their entirety.

Suitable NSAIDs, include, but are not limited to, acetaminophen, aspirin, diclofenac, ibuprofen, ketoprofen, naproxen, indomethacin, including but not limited to prodrugs thereof, and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, 13$^{th}$ Edition; and in U.S. Pat. Nos. 6,057,347 and 6,297,260 assigned to NitroMed Inc., the disclosures of which are incorporated herein by reference in their entirety.

Suitable H$_2$ receptor antagonists, include, but are not limited to, cimetidine, roxatidine, rantidine and the like. Suitable H$_2$ receptor antagonists are described more fully in the literature, such as in Goodman and Gilman, The Pharmacological Basis of Therapeutics (9th Edition), McGraw-Hill, 1995, Pgs. 901-915; the Merck Index on CD-ROM, 13$^{th}$ Edition; and in WO 00/28988 assigned to NitroMed Inc., the disclosures of which are incorporated herein by reference in their entirety.

Suitable antineoplastic agents, include but are not limited to, 5-FU-fibrinogen, acanthifolic acid, aminothiadiazole, altretamine, anaxirone, aclarubicin and the like. Suitable antineoplastic agents are also described in U.S. Pat. No. 6,025,353 and WO 00/38730, the 25 disclosures of which are incorporated herein by reference in their entirety.

Suitable antiplatelet agents, include but are not limited to, aspirin, ticlopidine, dipyridamole, clopidogrel, glycoprotein IIb/IIIa receptor antagonists, and the like. Suitable antineoplastic agents are also described in WO 99/45913, the disclosure of which is incorporated herein by reference in its entirety. In a preferred embodiment of the invention, the antiplatelet agent is aspirin, more preferably, low-dose aspirin (i.e. 75 mg-100 mg/day).

Suitable thrombin inhibitors, include but are not limited to, N'-((1-(aminoiminomethyl)-4-piperidinyl)methyl)-N-(3, 3-diphenylpropinyl)-L-proline amide), 3-(2-phenylethylamino)-6-methyl-1-(2-amino-6-methyl-5-methylene-carboxamidomethylpyridinyl)-2-pyrazinone, 3-(2-phenethylamino)-6-methyl-1-(2-amino-6-methyl-5-methylenecarboxamidomethylpyridinyl)-2-pyridinone, and the like. Suitable thrombin inhibitors are also described in WO 00/18352, the disclosure of which is incorporated herein by reference in its entirety.

Suitable thromboxane inhibitors, include but are not limited to thromboxane synthase inhibitors, thromboxane receptor antagonists, and the like. Suitable thromboxane inhibitors, are also described in WO 01/87343, the disclosure of which is incorporated herein by reference in its entirety.

Suitable decongestants include, but are not limited to, phenylephrine, phenylpropanolamine, pseudophedrine, oxymetazoline, ephinephrine, naphazoline, xylometazoline, propylhexedrine, levo-desoxyephedrine, and the like.

Suitable antitussives include, but are not limited to, codeine, hydrocodone, caramiphen, carbetapentane, dextramethorphan, and the like.

Suitable proton pump inhibitors, include, but are not limited to, omeprazole, esomeprazole, lansoprazole, rabeprazole, pantoprazole, and the like. Suitable proton pump inhibitors are described more fully in the literature, such as in Goodman and Gilman, The Pharmacological Basis of Therapeutics (9th Edition), McGraw-Hill, 1995, Pgs. 901-915; the Merck Index on CD-ROM, $13^{th}$ Edition; and in WO 00/50037 assigned to NitroMed Inc., the disclosures of which are incorporated herein by reference in their entirety.

The compounds and compositions of the invention, may also be used in combination therapies with opioids and other analgesics, including, but not limited to, narcotic analgesics, Mu receptor antagonists, Kappa receptor antagonists, nonnarcotic (i.e. non-addictive) analgesics, monoamine uptake inhibitors, adenosine regulating agents, cannabinoid derivatives, neurokinin 1 receptor antagonists, Substance P antagonists, neurokinin-1 receptor antagonists, sodium channel blockers, N-methyl-D-aspartate receptor antagonists, and mixtures of two or more thereof. Preferred combination therapies would be with morphine, meperidine, codeine, pentazocine, buprenorphine, butorphanol, dezocine, meptazinol, hydrocodone, oxycodone, methadone, Tramadol ((+) enantiomer), DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol ((−) enantiomer), GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, CP-99,994, and mixtures of two or more thereof.

The compounds and compositions of the invention can also be used in combination with inducible nitric oxide synthase (iNOS) inhibitors. Suitable iNOS inhibitors are disclosed in U.S. Pat. Nos. 5,132,453 and 5,273,875, and in WO 97/38977 and WO 99/18960, the disclosures of each of which are incorporated by reference herein in their entirety.

The invention is also based on the discovery that the administration of a therapeutically effective amount of the compounds and compositions described herein is effective for treating inflammation, pain (both chronic and acute), and fever, such as, for example, analgesic in the treatment of pain, including, but not limited to headaches, migraines, postoperative pain, dental pain, muscular pain, and pain resulting from cancer; as an antipyretic for the treatment of fever, including but not limited to, rheumatic fever, symptoms associated with influenza or other viral infections, common cold, low back and neck pain, dysmenorrhea, headache, toothache, sprains, strains, myositis, neuralgia, synovitis; arthritis, including but not limited to rheumatoid arthritis, degenerative joint disease (osteoarthritis), spondyloarthropathies, gouty arthritis, systemic lupus erythematosus and juvenile arthritis. For example, the patient can be administered a therapeutically effective amount of at least one COX-2 selective inhibitor, that is optionally nitrosated and/or nitrosylated. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and, at least one therapeutic agent, including but not limited to, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Another embodiment of the invention provides methods for treating gastrointestinal disorders and/or improving the gastrointestinal properties of the COX-2 selective inhibitor by administering to the patient in need thereof a therapeutically effective amount of the compounds and/or compositions described herein. Such gastrointestinal disorders refer to any disease or disorder of the upper gastrointestinal tract (e.g., esophagus, the stomach, the duodenum, jejunum) including, for example, inflammatory bowel disease, Crohn's disease, gastritis, irritable bowel syndrome, ulcerative colitis, peptic ulcers, stress ulcers, gastric hyperacidity, dyspepsia, gastroparesis, Zollinger-Ellison syndrome, gastroesophageal reflux disease, bacterial infections (including, for example, a *Helicobacter Pylori* associated disease), short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns. For example, the patient can be administered a therapeutically effective amount of at least one COX-2 selective inhibitor, that is optionally nitrosated and/or nitrosylated In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and, at least one therapeutic agent, including but not limited to, including but not limited to, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Yet another embodiment of the invention provides methods for facilitating wound healing (such as, for example, ulcer healing, bone healing including osteoporosis) by administering to the patient in need thereof a therapeutically effective amount of the compounds and/or compositions described herein. Wound refers to, and includes, any lesion that is characterized by loss of tissue, and, includes, but is not limited to, ulcers, cuts, burns, bone fractures, orthopedic procedure, wound infliction, and the like. Ulcers refers to lesions of the upper gastrointestinal tract lining that are characterized by loss of tissue, and, include, but are not limited to, gastric ulcers, duodenal ulcers, gastritis, and the like. For example, the patient can be administered a therapeutically effective amount of at least one COX-2 selective inhibitor, that is optionally nitrosated and/or nitrosylated In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and, at least one therapeutic agent, and, optionally, at least one nitric oxide donor. The compounds can be administered separately or in the form of a composition.

Another embodiment of the invention provides methods to decrease or reverse renal and/or other toxicities (such as, for example, kidney toxicity, respiratory toxicity) by administering to a patient in need thereof a therapeutically effective amount of the compounds and/or compositions described herein. For example, the patient can be administered a therapeutically effective amount of at least one COX-2 selective inhibitor, that is optionally nitrosated and/or nitrosylated In another embodiment, the patient can be administered a therapeutically effective amount of at least one COX-2 selective inhibitor, that is optionally nitrosated and/or nitrosylated, and at least one nitric oxide donor. In yet another embodiment, the patient can be administered a therapeutically effective amount of at least one COX-2 selective inhibitor, that is optionally nitrosated and/or nitrosylated, and at least one therapeutic agent, and, optionally, at least one nitric oxide donor. The compounds can be administered separately or in the form of a composition.

Another embodiment of the invention provides methods to treat or prevent disorders resulting from elevated levels of COX-2 by administering to a patient in need thereof a therapeutically effective amount of the compounds and/or compositions described herein. For example, the patient can be administered a therapeutically effective amount of at least one COX-2 selective inhibitor, that is optionally nitrosated and/or nitrosylated. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and at least one therapeutic agent, including but not limited to, steroids, a nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Disorders resulting from elevated levels of COX-2 (e.g., COX-2 mediated disorders) include, but are not limited to, for example, angiogenisis, arthritis, asthma, bronchitis, menstrual cramps, premature labor, tendinitis, bursitis; skin-related conditions, such as, for example, psoriasis, eczema, surface wounds, burns and dermatitis; post-operative inflammation including from ophthalmic surgery, such as, for example, cataract surgery and refractive surgery, and the like; treatment of neoplasia, such as, for example, brain cancer, bone cancer, epithelial cell-derived neoplasia (epithelial carcinoma), such as, for example, basal cell carcinoma, adenocarcinoma, gastrointestinal cancer, such as, for example, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body, benign and cancerous tumors, growths, polyps, adenomatous polyps, including, but not limited to, familial adenomatous polyposis, fibrosis resulting from radiation therapy, and the like; treatment of inflammatory processes in diseases, such as, for example, vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like; treatment of ophthalmic diseases and disorders, such as, for example, retinitis, retinopathies, uveitis, ocular photophobia, acute injury to the eye tissue, glaucoma, inflammation of the eye and elevation of intraocular pressure and the like; treatment of pulmonary inflammation, such as, for example, those associated with viral infections and cystic fibrosis, and the like; treatment of central nervous system disorders, such as, for example, cortical dementia including Alzheimer's disease, vascular dementia, multi-infarct dementia, pre-senile dementia, alcoholic dementia, senile dementia, and central nervous system damage resulting from stroke, ischemia and trauma, and the like; treatment of allergic rhinitis, respiratory distress syndrome, endotoxin shock syndrome, atherosclerosis; treatment of inflammations and/or microbial infections including, for example, inflammations and/or infections of the eyes, ears, nose, throat, and/or skin; treatment and/or prevention of cardiovascular disorders, such as, for example, coronary artery disease, aneurysm, arteriosclerosis, atherosclerosis, including, but not limited to, cardiac transplant atherosclerosis, myocardial infarction, hypertension, ischemia, embolism, stroke, thrombosis, venous thrombosis, thromboembolism, thrombotic occlusion and reclusion, restenosis, angina, unstable angina, shock, heart failure, coronary plaque inflammation, bacterial-induced inflammation, such as, for example, *Chlamydia*-induced inflammation, viral induced inflammation, inflammation associated with surgical procedures, such as, for example, vascular grafting, coronary artery bypass surgery, revascularization procedures, such as, for example, angioplasty, stent placement, endarterectomy, vascular procedures involving arteries, veins, capillaries, and the like; treatment and/or prevention of urinary and/or urological disorders, such as, for example, incontinence and the like; treatment and/or prevention of endothelial dysfunctions, such as, for example, diseases accompanying these dysfunctions, endothelial damage from hypercholesterolemia, endothelial damage from hypoxia, endothelial damage from mechanical and chemical noxae, especially during and after drug, and mechanical reopening of stenosed vessels, for example, following percutaneous transluminal angiography (PTA) and percuntaneous transluminal coronary angiography (PTCA), endothelial damage in postinfarction phase, endothelium-mediated reocculusion following bypass surgery, blood supply disturbances in peripheral arteries, as well as, cardiovascular diseases, and the like; methods for treating and/or preventing tissue deterioration, such as, for example, for organ transplants, and the like; disorders treated by the inhibition and/or prevention of activation, adhesion and infiltration of neutrophils at the site of inflammation; and disorders treated by the inhibition and/or prevention of platelet aggregation. The compounds and compositions of the invention can also be used as a pre-anesthetic medication in emergency operations to reduce the danger of aspiration of acidic gastric contents.

Another embodiment of the invention provides methods for improving the cardiovascular profile of COX-2 selective inhibitors by administering to a patient in need thereof a therapeutically effective amount of the compounds and/or compositions described herein. For example, the patient can be administered a therapeutically effective amount of at least one nitrosated and/or nitrosylated COX-2 selective inhibitor of the invention. In another embodiment, the patient can be administered a therapeutically effective amount of at least one COX-2 selective inhibitor, that is optionally nitrosated and/or nitrosylated, and at least one nitric oxide donor. In yet another embodiment, the patient can be administered a therapeutically effective amount of at least one COX-2 selective inhibitor, that is optionally nitrosated and/or nitrosylated, at least one of 3-hydroxy-3-methylglutaryl coenzyme A (HMG-CoA) inhibitors, antiplatelet agents, thrombin inhibitors, thromboxane inhibitors, and, optionally, at least one nitric oxide donor. The compounds can be administered separately or in the form of a composition.

When administered separately, the COX-2 selective inhibitor, that is optionally nitrosated and/or nitrosylated, can be administered about the same time as part of the overall treatment regimen, i.e., as a combination therapy. "About the same time" includes administering the COX-2 selective inhibitor, that is optionally nitrosated and/or nitrosylated, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one COX-2 selective inhibitor and/or at least one nitrosated and/or nitrosylated COX-2 selective inhibitor and/or at least one nitric oxide donor and/or therapeutic agent, they can also be used in combination with one or more additional compounds which are known to be effective against the specific disease state targeted for treatment. The nitric oxide donors, therapeutic agents and/or other additional compounds can be administered simultaneously with, subsequently to, or prior to administration of the COX-2 selective inhibitor and/or nitrosated and/or nitrosylated COX-2 selective inhibitor.

The compounds and compositions of the invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailability of the compositions can be enhanced by micronization of the formulations using conventional techniques such as grinding, milling, spray drying and the like in the presence of suitable excipients or agents such as phospholipids or surfactants.

The preferred methods of administration of the COX-2 selective inhibitors and compositions for the treatment of gastrointestinal disorders are orally, bucally or by inhalation. The preferred methods of administration for the treatment of inflammation and microbial infections are orally, bucally, topically, transdermally or by inhalation.

The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesuifonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chlorprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given COX-2 selective inhibitor of the invention that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The amount of nitric oxide donor in a pharmaceutical composition can be in amounts of about 0.1 to about 10 times the molar equivalent of the COX-2 selective inhibitor. The usual daily doses of the COX-2 selective inhibitors are about 0.001 mg to about 140 mg/kg of body weight per day, preferably 0.005 mg to 30 mg/kg per day, or alternatively about 0.5 mg to about 7 g per patient per day. For example, inflammations may be effectively treated by the administration of from about 0.01 mg to 50 mg of the compound per kilogram of body weight per day, or alternatively about 0.5 mg to about 3.5 g per patient per day. The compounds may be administered on a regimen of up to 6 times per day, preferably 1 to 4 times per day, and most preferably once per day. Effective doses may be extrapolated from dose-response curves derived from in vitro or animal model test systems and are in the same ranges or less than as described for the commercially available compounds in the Physician's Desk Reference, supra.

The invention also provides pharmaceutical kits comprising one or more containers filled with one or more of the ingredients of the pharmaceutical compounds and/or compositions of the invention, including, at least, one or more of the novel COX-2 selective inhibitors, that is optionally nitrosated and/or nitrosylated, and one or more of the NO donors described herein. Associated with such kits can be additional therapeutic agents or compositions (e.g., steroids, NSAIDs, 5-lipoxygenase (5-LO) inhibitors, leukotriene $B_4$ (LTB$_4$) receptor antagonists and leukotriene $A_4$ (LTA$_4$) hydrolase inhibitors, 5-HT agonists, HMG-CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like), devices for administering the compositions, and notices in the form prescribed by a governmental agency regulating the manufacture, use or sale of pharmaceuticals or biological products which reflects approval by the agency of manufacture, use or sale for humans.

EXAMPLES

The following non-limiting examples further describe and enable one of ordinary skill in the art to make and use the invention. In each of the examples, flash chromatography was performed on 40 micron silica gel (Baker).

Example 1

1-(1-Cyclohexylmethyl-3-((nitrooxy)methyl)pyrazol-5-yl)-4-(methylsulfonyl) benzene 1a. N-((1Z)-1-Aza-2-cyclohexylvinyl)(tert-butoxy)carboxamide Cyclohexane carboxaldehyde (5.0 g, 44.5 mmol) and t-butyl carbazate (5.89 g, 44.5 mmol) in methanol (140 mL) was stirred at room temperature for 1 hour. The solvent was evaporated and the resulting solid dried under vacuo to give a white solid in quantitative yield; mp 123-125° C. $^1$H NMR (300 MHz, CDCl$_3$) δ 7.61 (bs, 1H), 7.02 (d, J=5.9 Hz, 1H), 2.22-2.39 (m, 1H), 1.60-1.89 (m, 5H), 1.49 (s, 9H), 1.19-1.47 (m, 5H); $^{13}$CNMR (75 MHz, CDCl$_3$) δ 152.5, 151.5, 81.0, 40.7, 30.4, 28.5, 26.0, 25.6; mass spectrum (API-TIS) m/z 227 (MH$^+$), 249 (MNa$^+$). Anal. calcd for $C_{12}H_{22}N_2O_2$: C, 63.69; H, 9.80; N, 12.38. Found: C, 63.97; H, 9.76; N, 12.26.

1b. (tert-Butoxy)-N-((cyclohexylmethyl)amino)carboxamide

Sodium cyanoborohydride (2.8 g, 44.6 mmol) was added portionwise to a suspension of the product of Example 1a (10.1 g, 44.6 mmol) in 50% acetic acid (125 mL) at room temperature. The resultant clear solution was stirred at room temperature for 2 hours. The reaction mixture was neutralized with 1N NaOH, extracted with CH$_2$Cl$_2$, washed with saturated NaHCO$_3$, dried, filtered and evaporated to give the title compound as a colorless oil in quantitative yield. $^1$H NMR (300 MHz, CDCl$_3$) δ 6.90 (bs, 1H), 6.15 (bs, 1H), 2.68 (d, J=6.7 Hz, 2H), 2.25-2.50 (m, 1H), 1.60-1.87 (m, 5H), 1.46 (s, 9H), 1.12-1.33 (m, 3H), 0.80-1.08 (m, 2H); mass spectrum (API-TIS) m/z 129 (MH$^+$).

1c. Cyclohexylmethylhydrazine Trifluoroacetate

Trifluoroacetic acid (20 mL) was added dropwise to a solution of the product of Example 1b (6.4 g, 28.1 mmol) in CH$_2$Cl$_2$ (20 mL). The reaction mixture was stirred at room temperature for 1 hour. The solvent was evaporated to give the trifluoroacetate salt of the title compound as a colorless oil in quantitative yield. $^1$H NMR (300 MHz, CDCl$_3$) δ 8.80 (bs, 5H), 2.98-3.08 (m, 2H), 1.64-1.92 (m, 6H), 1.12-1.47 (m, 3H), 0.90-1.10 (m, 2H); mass spectrum (API-TIS) m/z 129 (MH$^+$).

1d. Methyl (2Z)-2-hydroxy-4-(4-methylthiophenyl)-4-oxobut-2-enoate

Dimethyloxalate (26 g, 180.7 mmol) was added to a stirred suspension of sodium methoxide (9.75 g, 180.7 mmol) in dry toluene (200 mL) at 0° C. The white suspension was stirred for 15 minutes at 0° C. A solution of 4'-(methylthio)acetophenone (15 g, 90.4 mmol) in dry toluene (150 mL) was then added dropwise over 15 minutes giving a yellow suspension which was stirred for 2 hours at room temperature. The thick yellow suspension was transferred to a 2 liter flask and stirred vigorously with 10% HCl (250 mL) and EtOAc (200 mL) to dissolve all the solids present. The organic layer was separated and the aqueous layer was extracted with EtOAc (100 mL). The combined organic extracts were washed with water (250 mL), dried over Na$_2$SO$_4$ and the solvent was evaporated under reduced pressure to give thick brown oil. The brown oil was dissolved in CH$_2$Cl$_2$ (25 mL) and hexane (125 mL) and left in a freezer at −20° C. for 16 hours to give the title compound (18 g, 79%) as orange color solid; mp 81° C. $^1$H NMR (300 MHz, CDCl$_3$) δ 7.83 (d, J=8.6 Hz, 2H), 7.23 (d, J=8.6 Hz, 2H), 6.97 (s, 1H), 3.89 (s, 3H), 2.47 (s, 3H); $^{13}$C NMR (75 MHz, CDCl$_3$); mass spectrum (API-TIS) m/z 253 (MH$^+$). Anal. calcd for C$_{12}$H$_{12}$O$_4$S: C, 57.13; H, 4.79; S, 12.71. Found: C, 56.85; H, 4.76; S, 12.43.

1e. Methyl 1-(cyclohexylmethyl)-5-(4-methylthiophenyl)pyrazole-3-carboxylate

A mixture of the product of Example 1d (2 g, 7.9 mmol) and the product of Example 1c (3.5 g, 10.3 mmol) in methanol (40 mL) was heated at 70° C. for 2 hours and cooled to room temperature. The mixture was made basic with 5% Na$_2$CO$_3$ and extracted with EtOAc which was then washed with saturated NaHCO$_3$ and water. The organic extracts were dried over Na$_2$SO$_4$ and the solvent was evaporated under reduced pressure to give a thick oil, which was purified by chromatography over silica gel eluting with 1:2 EtOAc:Hex to give the title compound as a pale yellow solid (1.55 g, 57%); mp 92° C. $^1$H NMR (300 MHz, CDCl$_3$) δ 7.15-7.30 (m, 4H), 6.76 (s, 1H), 3.99 (d, J=7.4 Hz, 2H), 3.94 (s, 3H), 2.54 (s, 3H), 1.82-2.00 (m, 1H), 1.35-1.63 (m, 5H), 0.97-1.18 (m, 3H), 0.67-0.84 (m, 2H). $^{13}$C NMR (75 MHz, CDCl$_3$) δ 163.1, 145.2, 142.6, 140.2, 129.6, 126.5, 126.3, 108.9, 56.4, 52.1, 38.7, 30.5, 26.3, 25.6, 15.4; mass spectrum (API-TIS) m/z 345 (MH$^+$). Anal. calcd for C$_{19}$H$_{24}$N$_2$O$_2$S: C, 66.25; H, 7.02; N, 8.13. Found: C, 66.31; H, 7.20; N, 8.15.

1f. (1-(Cyclohexylmethyl)-5-(4-methylthiophenyl)pyrazol-3-yl)methan-1-ol

Lithium aluminum hydride (2.0 mL of 1M solution in THF, 79.0 mg, 2.09 mmol) was added dropwise to a solution of the product of Example 1e (0.72 g, 2.09 mmol) in THF (14 mL) at 0° C. The yellow solution was stirred at room temperature for 1 hour. Solid Na$_2$SO$_4$.10H$_2$O was added portionwise to the reaction mixture at 0° C., followed by few drops of water and 0.1 N NaOH. The solid was filtered and washed with EtOAc. The solvent was evaporated to give the title compound (0.5 g, 76%) as a white foam. $^1$H NMR (300 MHz, CDCl$_3$) δ 7.13-7.30 (m, 4H), 6.22 (s, 1H), 4.70 (s, 2H), 3.88 (d, J=7.3 Hz, 2H), 3.65 (bs, 1H), 2.53 (s, 3H), 1.75-1.83 (m, 1H), 1.40-1.68 (m, 5H), 0.92-1.28 (m, 3H), 0.60-0.82 (m, 2H); $^{13}$C NMR (75 MHz, CDCl$_3$) δ 151.5, 144.8, 139.5, 129.3, 127.2, 126.1, 104.6, 58.0, 55.3, 38.7, 30.3, 26.0, 25.5, 15.1; mass spectrum (API-TIS) m/z 317 (MH$^+$), 299 (M−OH).

1g. 1-(1-(Cyclohexylmethyl)-3-(hydroxymethyl)pyrazol-5-yl)-4-(methylsulfonyl)benzene The product of Example 1f (0.5 g, 1.58 mmol) was dissolved in MeOH (32 mL). OXONE® (1.94 g, 3.16 mmol) in water (7 mL) was added at room temperature. The reaction mixture was stirred for 1 hour and the resulting solid was removed by filtration. CH$_2$Cl$_2$ was added to the filtrate, and then the organic layer was washed with saturated NaHCO$_3$, water, dried over Na$_2$SO$_4$, and filtered. The residue after evaporation of the solvent was recrystallized from CH$_2$Cl$_2$/EtOAc/Hexane to give the title compound (0.33 g, 59%) as a white solid; mp 104° C. $^1$H NMR (300 MHz, CDCl$_3$) δ 8.04 (d, J=8.2 Hz, 2H), 7.59 (d, J=8.1 Hz, 2H), 6.32 (s, 1H), 4.74 (d, J=5.8 Hz, 2H), 3.92 (d, J=7.3 Hz, 2H), 3.13 (s, 3H), 1.98 (t, J=5.9 Hz, 1H), 1.80-1.94 (m, 1H), 1.40-1.70 (m, 5H), 0.98-1.25 (m, 3H), 0.65-0.82 (m, 2H); $^{13}$C NMR (75 MHz, CDCl$_3$) δ 151.8, 143.3, 140.6, 136.7, 130.0, 128.0, 105.4, 59.2, 56.0, 44.6, 39.0, 30.7, 26.3, 25.7; mass spectrum (API-TIS) m/z 349 (MH$^+$), 331 (M−OH). Anal. calcd for C$_{18}$H$_{24}$N$_2$O$_3$S: C, 62.04; H, 6.94; N, 8.04; S, 9.20. Found: C, 61.88; H, 6.91; N, 7.84; S, 9.09.

1h. 1-(1-(Cyclohexylmethyl)-3-((nitrooxy)methyl)pyrazol-5-yl)-4-(methylsulfonyl)benzene The product of Example 1g (0.22 g, 0.62 mmol) in CHCl$_3$ (2.6 mL) was added to a mixture of fuming HNO$_3$ (130 μL, 0.19 g, 3.1 mmol) and Ac$_2$O (0.47 mL, 0.5 g, 4.96 mmol) at −10° C. and stirred at −10° C. for 20 minutes. The reaction mixture was quenched with ice-cold water and extracted with CH$_2$Cl$_2$. The extracts were washed with ice-cold saturated NaHCO$_3$, water, dried over Na$_2$SO$_4$, filtered and the solvent evaporated under reduced pressure. The residue obtained was recrystallized from CH$_2$Cl$_2$/EtOAc/Hex to give the title compound as a white solid (0.17 g, 70%); mp 98-99° C. $^1$H NMR (300 MHz, CDCl$_3$) δ 8.05 (d, J=8.3 Hz, 2H), 7.58 (d, J=8.3 Hz, 2H), 6.41 (s, 1H), 5.50 (s, 2H), 3.93 (d, J=7.3 Hz, 2H), 3.13 (s, 3H), 1.80-1.97 (m, 1H), 1.40-1.68 (m, 5H), 1.00-1.28 (m, 3H), 0.67-0.82 (m, 2H); $^{13}$C NMR (75 MHz, CDCl$_3$) δ 138.31, 138.27, 135.6, 130.7, 124.7, 122.7, 102.2, 63.2, 50.9, 39.2, 33.6, 25.3, 20.9, 20.3; mass spectrum (API-TIS) m/z 394 (MH$^+$). Anal. calcd for C$_{18}$H$_{23}$N$_3$O$_5$S: C, 54.95; H, 5.89; N, 10.68; S, 8.15. Found: C, 54.96; H, 5.94; N, 10.49; S, 8.31.

Example 2

1-(1-Cyclohexylmethyl-3-((nitrooxy)methyl)pyrazol-5-yl)-4-(methylsulfonyl) benzene 2a. Methyl (2Z)-2-hydroxy-4-(4-(methylsulfonyl)phenyl)-4-oxobut-2-enoate Sodium methoxide was prepared by dissolving Na (6.9 g, 30 mmol) in MeOH (400 mL). The solution was cooled to 0° C. Dimethyl oxalate (33 g, 280 mmol) was added followed by 1-(4-(methylsulfonyl)phenyl)ethan-1-one (28 g, 140 mmol). The reaction mixture was allowed to warm to room temperature and stirred for 18 hours. The MeOH was evaporated and the residue triturated with 1N HCl (600 mL). The solid was collected on filter paper, washed with H$_2$O (2×250), and dried in vacuo. This gave the title compound (39 g, 100%) as a tan solid. $^1$H-NMR (300 MHz, CDCl$_3$) δ 8.17 (d, J=6.9 Hz, 2H), 8.09 (d, J=6.9 Hz, 2H), 7.10 (s, 1H), 3.97 (s, 3H), 3.10 (s, 3H).

2b. Methyl 1-(cyclohexylmethyl)-5-(4-(methylsulfonyl)phenyl)pyrazole-3-carboxylate The product of Example 1c (8 mL, 23 mmol) and the product of Example 2a (4.5 g, 16 mmol) were added to MeOH and heated at reflux for 3 hours. The reaction mixture was cooled to room temperature and diluted with H$_2$O (150 mL). The aqueous MeOH solution was extracted with CH$_2$Cl$_2$ (3×50). The combined organic extracts were washed with 1N Na$_2$CO$_3$ (2×50) and 1N HCl (1×50), dried over Na$_2$SO$_4$, concentrated. The residue was crystallized from MeOH (15 mL) to give the title compound (3.5 g, 58%) as a white solid. $^1$H-NMR (300 MHz, CDCl$_3$) δ 8.06 (d, J=8.4 Hz, 2H), 7.60 (d, J=8.4 Hz, 2H), 6.87 (s, 1H), 4.02 (d, J=7.5 Hz, 2H), 3.96 (s, 3H), 3.13 (s, 3H), 0.73-1.94 (mult, 11H).

2c. 4-(1-(Cyclohexylmethyl)-3-(hydroxymethyl)pyrazol-5-yl)-1-(methylsulfonyl)benzene A flask was charged with lithium aluminum hydride (125 mg, 3.3 mmol) in THF (5 mL) and cooled to 0° C. The product of Example 2b (750 mg, 2 mmol) in THF (5 mL) was added dropwise. The resulting mixture was stirred at 0°

C. for 15 minutes then warmed to room temperature with stirring for 1.5 hours. The excess lithium aluminum hydride was destroyed by adding sequentially H$_2$O (150 µL), 15% NaOH (150 µL), H$_2$O (450 µL). The precipitate that formed was removed by filtration through Celite, the filter cake was washed with EtOAc (2×10). The combined filtrates were dried over Na$_2$SO$_4$ and concentrated to give the title compound (790 mg, 100%) as a white solid. $^1$H-NMR (300 MHz, CDCl$_3$) δ 8.04 (d, J=8.4 Hz, 2H), 7.58 (d, J=8.4 Hz, 2H), 6.33 (s, 1H), 4.73 (d, J=5.1 Hz, 2H), 3.91 (d, J=7.2 Hz, 2H), 3.13 (s, 3H), 0.73-2.09 (mult, 11H).

2d. 4-(3-(Bromomethyl)-1-(cyclohexylmethyl)pyrazol-5-yl)-1-(methylsulfonyl)benzene The product of Example 2c (790 mg, 2 mmol) was dissolved in CH$_2$Cl$_2$ (5 mL). Phosphorous tribromide (100 µL, 1 mmol) was added and the mixture was stirred at room temperature for 18 hours. The reaction mixture was transferred to a separation funnel with CH$_2$Cl$_2$ (40 mL) and washed with H$_2$O (1×10) and dried over Na$_2$SO$_4$. Evaporation of the solvent gave a residue that was filtered through silica gel eluting with Hex:EtOAc 1:1 to give the title compound (440 mg, 53%) as a white solid, mp 141-143° C. $^1$H-NMR (300 MHz, CDCl$_3$) δ 8.04 (d, J=8.2 Hz, 2H), 7.59 (d, J=8.2 Hz, 2H), 6.39 (s, 1H), 4.53 (s, 2H), 3.91 (d, J=7.3 Hz, 2H), 3.13 (s, 3H), 0.73-1.88 (mult, 11H); mass spectrum (API-TIS) m/z 411 (MH$^+$). Anal calcd for C$_{18}$H$_{23}$BrN$_2$O$_2$S: C, 52.56; H, 5.64; N, 6.81. Found C, 52.47; H, 5.67; N, 6.65.

2e. 4-(1-(Cyclohexylmethyl)-3-((2-hydroxyethoxy)methyl)pyrazol-5-yl)-1 (methylsulfonyl)benzene To a slurry of 95% NaH (75 mg, 3 mmol) in THF (5 mL) was added 2-benzyloxyethanol (275 µL, 2 mmol). The mixture was stirred at room temperature for 15 minutes by which time effervescence had ceased. The product of Example 2d (410 mg, 1 mmol) in THF (2 mL) was added and the reaction mixture was stirred at room temperature for 18 hours. Excess NaH was quenched with saturated NH$_4$Cl (20 mL). The aqueous THF was extracted with EtOAc (3×20). The combined extracts were washed with H$_2$O, brine, dried over Na$_2$SO$_4$, and concentrated. The residue was taken up in EtOAc (30 mL), 10% Pd/C (300 mg) was added and the mixture was shaken under 50 psi of hydrogen for 18 hours. The reaction mixture was filtered through Celite and the filter cake was washed with EtOAc (2×25). The combined filtrate was washed with H$_2$O (2×25) and brine (1×25), dried over Na$_2$SO$_4$, and concentrated. Chromatography of the residue on silica gel eluting with Hex:EtOAc 1:2 gave the title compound (200 mg, 51%) as a white solid, mp 73-75° C. $^1$H-NMR (300 MHz, CDCl$_3$) δ 8.03 (d, J=8.2 Hz, 2H), 7.58 (d, J=8.2 Hz, 2H), 6.33 (s, 1H4.64 (t, J=4.1 Hz, 2H), 4.62 (s, 2H), 3.92 (d, J=7.3 Hz, 2H), 3.77 (br mult, 2H), 3.67-3.69 (Mult 2H), 3.12 (s, 3H), 0.73-1.91 (mult, 10H); mass spectrum (API-TIS) m/z 393 (MH$^+$). Anal calcd for C$_{20}$H$_{28}$N$_2$O$_4$S: C, 61.20; H, 7.19; N, 7.14. Found C, 60.97; H, 6.99; N, 7.02.

2f. 4-(1-(Cyclohexylmethyl)-3-((2-(nitrooxy)ethoxy)methyl)pyrazol-5-yl)-1-(methylsulfonyl)benzene Fuming 90% HNO$_3$ (0.5 mL, 12 mmol) was cooled to 0° C. The product of Example 2e (200 mg, 0.5 mmol) was added and allowed to stir at 0° C. for 45 minutes. The reaction mixture was poured in to 0.5 N Na$_2$CO$_3$ (20 mL). The aqueous mixture was extracted with EtOAc (2×15). The combined extracts were washed with brine, dried over Na$_2$SO$_4$, and concentrated. The residue was triturated with Hex:EtOAc 2:1 (2 ml). The solid was isolated by filtration to give the title compound (100 mg, 50%) as a pale yellow solid. mp 98-100° C. $^1$H-NMR (300 MHz, CDCl$_3$) δ 8.04 (d, J=8.4 Hz, 2H), 7.59 (d, J=8.4 Hz, 2H), 6.36 (s, 1H), 4.64 (t, J=4.1 Hz, 2H), 4.60 (s, 2H), 3.92 (d, J=7.3 Hz, 2H), 3.83 (t, J=4.4 Hz, 2H), 3.13 (s, 3H), 0.70-1.87 (mult, 11H); mass spectrum (API-TIS) m/z 348 (MH$^+$). Anal calcd for C$_{20}$H$_{27}$N$_3$O$_6$S: C, 54.91; H, 6.22; N, 9.60. Found C, 54.17; H, 6.38; N, 9.24.

Example 3

4-(Methylsulfonyl)-1-(3-((nitrooxy)methyl)-1-benzylpyrazol-5-yl)benzene

3a. Methyl 5-(4-(methylthiophenyl)-1-benzylpyrazole-3-carboxylate

A mixture of the product Example 1d (2 g, 7.9 mmol) and benzylhydrazine hydrochloride (1.64 g, 10.3 mmol) in methanol (40 mL) and trifluoroacetic acid (0.5 mL) was heated at 70° C. for 2 hours and cooled to room temperature. The mixture was made basic with 5% Na$_2$CO$_3$ and extracted with EtOAc which was then washed with saturated NaHCO$_3$ and water. The organic extracts were dried over Na$_2$SO$_4$ and the solvent was evaporated. The residue was recrystallized from CH$_2$Cl$_2$/EtOAc/Hex to give the title compound as a white solid (1.88 g, 70%); mp 94-96° C. $^1$H NMR (300 MHz, CDCl$_3$) δ 7.12-7.30 (m, 7H), 7.00-7.08 (m, 2H), 6.87 (s, 1H), 5.41 (s, 2H), 3.95 (s, 3H), 2.50 (s, 3H). $^{13}$C NMR (75 MHz, CDCl$_3$) δ 163.0, 145.2, 143.1, 140.6, 136.7, 129.4, 128.8, 127.9, 126.9, 126.3, 126.0, 109.4, 54.2, 52.2, 15.4; mass spectrum (API-TIS) m/z 339 (MH$^+$), 307 (M–OCH$_3$); Anal. Calcd for C$_{19}$H$_{18}$N$_2$O$_2$S: C, 67.43; H, 5.36; N, 8.28; S, 9.47. Found: C, 67.56; H, 5.39; N, 8.29; S, 9.39.

3b. (5-(4-(Methylthiophenyl)-1-benzylpyrazol-3-yl)methan-1-ol

The title compound was prepared as a white foam in quantitative yield from the product of Example 3a by following the procedure for Example 1f. $^1$H NMR (300 MHz, CDCl$_3$) δ 7.19-7.28 (m, 7H), 7.02-7.04 (m, 2H), 6.32 (s, 1H), 5.28 (s, 2H), 4.70 (s, 2H), 2.49 (s, 3H). $^{13}$C NMR (75 MHz, CDCl$_3$) δ 152.1, 144.9, 139.9, 137.6, 129.3, 128.8, 127.7, 127.1, 126.8, 126.4, 104.9, 59.1, 53.2, 15.5; mass spectrum (API-TIS) m/z 311 (MH$^+$), 293 (M-OH).

3c. 1-(3-(Hydroxymethyl)-1-benzylpyrazol-5-yl)-4-(methylsulfonyl)benzene

The title compound was prepared as a white solid (0.55 g, 66%) from the product of Example 3b by following the procedure for Example 1g; mp 155° C.; $^1$H NMR (300 MHz, CDCl$_3$) δ 7.96 (d, J=8.4 Hz, 2H), 7.51 (dd, J=1.7 and 6.9 Hz, 2H), 7.27-7.30 (m, 3H), 7.02-7.05 (m, 2H), 6.45 (s, 1H), 5.33 (s, 2H), 4.76 (d, J=5.8 Hz, 2H), 3.08 (s, 3H), 2.26 (t, J=5.9 Hz, 1H). $^{13}$C NMR (75 MHz, CDCl$_3$) δ 152.4, 143.2, 140.6, 137.0, 136.0, 129.7, 129.0, 127.9, 126.6, 106.0, 59.0, 53.6, 44.6. Mass spectrum (API-TIS) m/z 343 (MH$^+$). Anal. Calcd for C$_{18}$H$_{18}$N$_2$O$_3$S: C, 63.14; H, 5.30; N, 8.18; S, 9.36. Found: C, 62.97; H, 5.23; N, 8.03; S, 9.16.

3d. 4-(Methylsulfonyl)-1-(3-((nitrooxyl)methyl)-1-benzylpyrazol-5-yl)benzene

The title compound was prepared as a white solid (0.22 g, 57%) from the product of Example 3c by following the procedure for Example 1h; mp 93-94° C.; $^1$H NMR (300 MHz, CDCl$_3$) δ 7.97 (dd, J=1.6 and 6.8 Hz, 2H), 7.49 (dd, J=1.7 and 6.7 Hz, 2H), 7.26-7.33 (m, 3H), 7.01-7.03 (m, 2H), 6.53 (s, 1H), 5.54 (s, 2H), 5.35 (s, 2H), 3.08 (s, 3H). $^{13}$C NMR (75 MHz, CDCl$_3$) δ 144.3, 143.6, 141.1, 136.6, 135.4, 129.8, 129.0, 128.2, 128.0, 126.7, 108.1, 68.4, 53.9, 44.5;

mass spectrum (API-TIS) m/z 388 (MH+). Anal. Calcd for C$_{18}$H$_{17}$N$_3$O$_5$S: C, 55.81; H, 4.42; N, 10.85; S, 8.28. Found: C, 55.57; H, 4.37; N, 10.78; S, 8.50.

Example 4

1-(3-((1E)-3-(nitrooxy)prop-1-enyl)-1-(cyclohexylmethyl)pyrazol-5-yl)-4-(methylsulfonyl)benzene 4a. 1-(Cyclohexylmethyl)-5-(4-methylthiophenyl)pyrazole-3-carbaldehyde To a stirred solution of oxalyl chloride (0.60 mL, 0.87 g, 6.8 mmol) in CH$_2$Cl$_2$ (2.3 mL) at −78° C. under nitrogen was added DMSO (0.97 mL, 1.06 g, 13.7 mmol) in CH$_2$Cl$_2$ (1.8 mL) dropwise over a period of 20 min. To this solution the product of Example 1f (1.73 g, 5.47 mmol) in CH$_2$Cl$_2$ (10 mL) was added dropwise over a period of 40 minutes at −78° C. The mixture was stirred at −78° C. for 1.5 hours. Triethylamine (3.8 mL, 2.77 g, 27.3 mmol) in CH$_2$Cl$_2$ (2.3 mL) was then added dropwise over a period of 45 minutes at −78° C. The resultant mixture was stirred at 0° C. for 20 minutes. To this mixture, water (2 mL) was added dropwise followed by CH$_2$Cl$_2$ (50 mL). The organic layer was separated and the aqueous layer was extracted with CH$_2$Cl$_2$. The combined organic extracts were washed with 5% HCl, dried over Na$_2$SO$_4$ and filtered. The residue after evaporation of the solvent was chromatographed on silica gel eluting with 1:9 EtOAc/Hexane to give the title compound (1.6 g, 93%) as a clear oil. $^1$H NMR (300 MHz, CDCl$_3$) δ 9.99 (s, 1H), 7.22-7.37 (m, 4H), 6.75 (s, 1H), 4.01 (d, J=7.4 Hz, 2H), 2.54 (s, 3H), 1.83-2.00 (m, 1H), 1.42-1.69 (m, 5H), 1.00-1.25 (m, 3H), 0.73-0.89 (m, 2H). $^{13}$C NMR (75 MHz, CDCl$_3$) δ 181.7, 145.3, 145.2, 140.6, 135.2, 124.2, 120.9, 100.4, 51.2, 33.5, 25.2, 20.9, 20.3, 10.1; mass spectrum (API-TIS) m/z 315 (MH+); Anal. Calcd for C$_{18}$H$_{22}$N$_2$OS: C, 68.75; H, 7.05; N, 8.91. Found: C, 68.48; H, 6.82; N, 8.88.

4b. Methyl (2E)-3-(1-(cyclohexylmethyl)-5-(4-methylthiophenyl)pyrazol-3-yl)prop-2-enoate n-Butyl lithium (2.5 M solution in hexane, 1.65 mL, 0.27 g, 4.14 mmol) was added dropwise to a solution of trimethylphosphonoacetate (0.70 g, 3.82 mmol) in THF (7 mL) at −78° C. The resultant solution was stirred at −78° C. for 1 hour. To this solution the product from Example 4a (1.0 g, 3.18 mmol) in THF (7 mL) was added dropwise. The reaction mixture was stirred at −78° C. for 1 hour. The reaction mixture was gradually allowed to warm to room temperature and stirred for 24 hours. Water was added and extracted with EtOAc, which was then washed with water, dried over Na$_2$SO$_4$ and filtered. The residue obtained after evaporation of the solvent was purified by chromatography over silica gel eluting with 1:9 to 2:8 EtOAc:Hexane to give the pure E-isomer (1.04 g, 88%) as a colorless oil. $^1$H NMR (300 MHz, CDCl$_3$) δ 7.69 (d, J=16.0 Hz, 1H), 7.20-7.34 (m, 4H), 6.45 (s, 1H), 6.40 (d, J=16.2 Hz, 1H), 3.92 (d, J=7.3 Hz, 2H), 3.79 (s, 3H), 2.53 (s, 3H), 1.80-1.98 (m, 1H), 1.37-1.70 (m, 5H), 0.92-1.22 (m, 3H), 0.62-0.82 (m, 2H); $^{13}$C NMR (75 MHz, CDCl$_3$) δ 167.6, 147.2, 145.4, 140.0, 137.3, 129.6, 127.0, 126.3, 118.5, 105.1, 56.0, 51.7, 38.9, 30.6, 26.3, 25.7, 15.5; mass spectrum (API-TIS) m/z 371 (MH+); Anal. Calcd for C$_{21}$H$_{26}$N$_2$O$_2$S: C, 68.08; H, 7.07; N, 7.56. Found: C, 67.77; H, 6.76; N, 7.39.

4c. (2E)-3-(1-(Cyclohexylmethyl)-5-(4-methylthiophenyl)pyrazol-3-yl)prop-2-en-1-ol Lithium aluminum hydride (2.0 mL of 1M solution in THF, 75.9 mg, 2.0 mmol) was added dropwise to a solution of the product of Example 4b (0.74 g, 2.0 mmol) in THF (11 mL) at 0° C. The yellow solution was stirred for 30 min at 0° C. and at room temperature for 30 min. Solid Na$_2$SO$_4$.10H$_2$O was added portionwise to the reaction mixture at 0° C., followed by few drops of water and 0.1 N NaOH. The solid was filtered and washed with EtOAc. The solvent was evaporated and the product was purified by column chromatograpy to give the title compound (0.44 g, 64%) as an oil and 3-(1-(cyclohexylmethyl)-5-(4-methylthiophenyl)pyrazol-3-yl) propan-1-ol (0.21 g, 31%) as a minor product. $^1$H NMR (300 MHz, CDCl$_3$) δ 7.24-7.33 (m, 4H), 6.66 (dt, J=1.2 and 16.0 Hz, 1H), 6.32-6.42 (m, 1H), 6.32 (s, 1H), 4.31 (dd, J=1.3 and 5.7 Hz, 2H), 3.88 (d, J=7.4 Hz, 2H), 2.53 (s, 3H), 1.75-1.93 (m, 1H), 1.40-1.84 (m, 5H), 0.98-1.28 (m, 3H), 0.64-0.83 (m, 2H); $^{13}$C NMR (75 MHz, CDCl$_3$) δ 149.1, 144.8, 139.5, 130.2, 129.5, 127.5, 126.3, 123.4, 103.0, 63.5, 55.6, 38.9, 30.6, 26.3, 25.7, 15.5; mass spectrum (API-TIS) m/z 343 (MH+); Anal. Calcd for C$_{20}$H$_{26}$N$_2$OS: C, 70.14; H, 7.65; N, 8.18. Found: C, 70.13; H, 7.72; N, 8.18.

4d. 1-(3-((1E)-3-Hydroxyprop-1-enyl)-1-(cyclohexylmethyl)pyrazol-5-yl)-4-(methylsulfonyl)benzene The product of Example 4c (0.44 g, 1.29 mmol) was dissolved in MeOH (16 mL). OXONE® (1.58 g, 2.57 mmol) in water (3 mL) was added at room temperature. The reaction mixture was stirred for 1 hour and then filtered to remove the solid. CH$_2$Cl$_2$ was added to the filtrate which was washed with saturated NaHCO$_3$, water, dried over Na$_2$SO$_4$ and filtered. The solvent was evaporated to give the product (0.23 g, 48%) as a white foam; mp 49-52° C.; $^1$H NMR (300 MHz, CDCl$_3$) δ 8.03 (d, J=8.1 Hz, 2H), 7.59 (d, J=8.2 Hz, 2H), 6.66 (d, J=16.1 Hz, 1H), 6.41 (s, 1H), 6.32-6.47 (m, 1H), 4.32 (bd, J=5.2 Hz, 2H), 3.91 (d, J=7.3 Hz, 2H), 3.12 (s, 3H), 1.78-1.97 (m, 1H), 1.41-1.69 (m, 5H), 0.98-1.30 (m, 3H), 0.65-0.83 (m, 2H); $^{13}$C NMR (75 MHz, CDCl$_3$) δ149.5, 143.3, 140.5, 136.6, 130.7, 130.0, 127.9, 123.1, 104.0, 63.5, 56.0, 44.6, 39.0, 30.6, 26.3, 25.7; mass spectrum (API-TIS) m/z 375 (MH+); Anal. calcd for C$_{20}$H$_{26}$N$_2$O$_3$S: C, 64.14; H, 7.00; N, 7.48. Found: C, 64.11; H, 6.91; N, 7.40.

4e. 1-(3-((1E)-3-Nitrooxyprop-1-enyl)-1-(cyclohexylmethyl)pyrazol-5-yl)-4-(methylsulfonyl)benzene Fuming HNO$_3$ (0.34 mL, 0.50 g, 8.0 mmol) was added dropwise to a solution of the product from Example 4d (0.1 g, 0.27 mmol) in CHCl$_3$ (4 mL) at −10° C. and then stirred at −10° C. for 1 hour. The solution was diluted with CH$_2$Cl$_2$ and washed with ice cold saturated NaHCO$_3$, water, dried over Na$_2$SO$_4$, and filtered. The residue after evaporation of the solvent purified by chromatography over silica gel eluting with 1:2 EtOAc:Hexane to give the product as a white foam (0.70 mg, 62%); mp 44-47° C.; $^1$H NMR (300 MHz, CDCl$_3$) δ 8.05 (d, J=8.4 Hz, 2H), 7.59 (d, J=8.4 Hz, 2H), 6.82 (d, J=16.0 Hz, 1H), 6.44 (s, 1H), 6.24-6.32 (m, 1H), 5.08 (d, J=6.1 Hz, 2H), 3.92 (d, J=7.3 Hz, 2H), 3.13 (s, 3H), 1.80-1.95 (m, 1H), 1.35-1.95 (m, 5H), 0.95-1.25 (m, 3H), 0.60-0.82 (m, 2H); $^{13}$C NMR (75 MHz, CDCl$_3$) δ 148.2, 143.6, 140.8, 136.4, 130.14, 130.07, 128.1, 120.6, 104.7, 73.6, 58.5, 44.6, 33.5, 27.3, 25.7, 25.2; mass spectrum (API-TIS) m/z 420 (MH+). Anal. calcd for C$_{20}$H$_{25}$N$_3$O$_5$S.¼ mol H$_2$O: C, 56.66; H, 6.06; N, 9.91. Found: C, 56.80; H, 5.99; N, 9.85.

Example 5

3-(1-(Cyclohexylmethyl)-3-(3-(nitrooxy)propyl) pyrazol-5-yl)-4-(methylsulfonyl)benzene 5a. 3-(1-(Cyclohexylmethyl)-5-(4-methylthiophenyl)pyrazol-3-yl)propan-1-ol The title compound was prepared as a colorless oil (0.21 g, 31%) from the product of Example 4b by following the procedure for Example 4c. $^1$H NMR (300 MHz, CDCl$_3$) δ 7.20-7.35 (m, 4H), 6.03 (s, 1H), 3.85 (d, J=7.4 Hz, 2H), 3.74 (t, J=5.9 Hz, 2H), 2.78 (t, J=6.9 Hz, 2H), 2.53 (s, 3H), 1.94 (p, J=6.4 Hz, 2H), 1.78-1.90 (m, 1H), 1.40-1.68 (m, 5H), 0.98-1.25 (m, 3H), 0.63-0.84 (m, 2H); $^{13}$C NMR (75 MHz, CDCl$_3$) δ 151.7, 144.6, 139.2, 129.4, 127.7, 126.2, 104.8, 62.3, 55.3, 38.8, 32.1, 30.5, 26.3, 25.6, 25.2, 15.4; mass spectrum (API-TIS) m/z 345 (MH$^+$); Anal. calcd for C$_{20}$H$_{28}$N$_2$OS: C, 69.73; H, 8.19; N, 8.13. Found: C, 69.33; H, 7.82; 7.74.

5b. 1-(1-(Cyclohexylmethyl)-3-(3-hydroxypropyl)pyrazol-5-yl)-4-(methylsulfonyl)benzene The title compound was prepared as a white solid (0.16 g, 70%) from the product of Example 5a by following the procedure for Example 4d; mp 94-95° C.; $^1$H NMR (300 MHz, CDCl$_3$) δ 8.02 (d, J=8.3 Hz, 2H), 7.58 (d, J=8.3 Hz, 2H), 6.13 (s, 1H), 3.89 (d, J=7.4 Hz, 2H), 3.74 (t, J=6.0 Hz, 2H), 3.12 (s, 3H), 2.80 (t, J=7.1 Hz, 2H), 2.58 (t, J=5.7 Hz, 1H), 1.95 (p, J=6.6 Hz, 2H), 1.74-1.95 (m, 1H), 1.38-1.70 (m, 5H), 0.97-1.24 (m, 3H), 0.64-0.80 (m, 2H); $^{13}$C NMR (75 MHz, CDCl$_3$) δ 152.1, 142.9, 140.2, 136.8, 129.7, 127.8, 105.8, 62.2, 55.6, 44.5, 38.9, 32.1, 30.5, 26.2, 25.5, 25.0. Mass spectrum (API-TIS) m/z 377 (MH$^+$). Anal. calcd for C$_{20}$H$_{28}$N$_2$O$_3$S: C, 63.80; H, 7.50; N, 7.44. Found: C, 63.75; H, 7.35; 7.29.

5c. 1-(1-(Cyclohexylmethyl)-3-(3-(nitrooxy)propyl)pyrazol-5-yl)-4-(methylsulfonyl)benzene The title compound was prepared as a white solid (0.1 g, 62%) from the product of Example 5b by following the procedure for Example 1h; mp 76-77° C.; $^1$H NMR (300 MHz, CDCl$_3$) δ 8.03 (d, J=8.4 Hz, 2H), 7.57 (d, J=8.4 Hz, 2H), 6.13 (s, 1H), 4.54 (d, J=6.6 Hz, 2H), 3.89 (d, J=7.3 Hz, 2H), 3.12 (s, 3H), 2.79 (t, J=7.3 Hz, 2H), 2.13 (p, J=6.9 Hz, 2H), 1.75-1.95 (m, 1H), 1.37-1.68 (m, 5H), 0.97-1.22 (m, 3H), 0.64-0.82 (m, 2H); $^{13}$C NMR (75 MHz, CDCl$_3$) δ 150.6, 143.2, 140.5, 136.9, 129.9, 128.0, 105.8, 72.8, 55.9, 44.7, 39.1, 30.7, 26.8, 26.3, 25.7, 24.5; mass spectrum (API-TIS) m/z 422 (MH$^+$); Anal. calcd for C$_{20}$H$_{27}$N$_3$O$_5$S: C, 56.99; H, 6.46; N, 9.97. Found: C, 56.83; H, 6.48; 9.79.

Example 6

1-(1-(Cyclohexylmethyl)-3-vinylpyrazol-5-yl)-4-(methylsulfonyl)benzene 6a. 1-(1-(Cyclohexylmethyl)-3-vinylpyrazol-5-yl)-4-methylthiobenzene n-Butyl lithium (2.5 M solution in hexane, 0.67 mL, 0.11 g, 1.69 mmol) was added dropwise to a solution of methyltriphenylphosphonium bromide (0.51 g, 1.43 mmol) in THF (4 mL) at –78° C. The resultant solution was stirred at –78° C. for 1 hour. To this solution the product from Example 4a (0.41 g, 1.3 mmol) in THF (4 mL) was added dropwise. The reaction mixture was stirred at –78° C. for 1 hour. The reaction mixture was gradually allowed to warm to room tmeperature and stirred for 24 hours. Water was added and extracted with EtOAc, which was then washed with water, dried over Na$_2$SO$_4$ and filtered. The residue obtained after evaporation of the solvent was purified by chromatography over silica gel eluting with 0.5:10 EtOAc: Hexane to give the title compound (0.1 g, 25%) as a colorless oil. $^1$H NMR (300 MHz, CDCl$_3$) δ 7.26-7.35 (m, 4H), 6.70-6.84 (m, 1H), 6.38 (s, 1H), 5.73 (dd, J=1.3, 18.0 Hz, 1H), 5.30 (dd, J=0.8, 10.8 Hz, 1H), 3.91 (d, J=7.3 Hz, 2H), 2.54 (s, 3H), 1.78-1.97 (m, 1H), 1.38-1.64 (m, 5H), 0.92-1.25 (m, 3H), 0.63-0.84 (m, 2H); $^{13}$C NMR (75 MHz, CDCl$_3$) δ 150.0, 144.7, 139.4, 129.5, 127.6, 126.2, 114.8, 102.5, 55.6, 38.8, 30.6, 26.3, 25.7, 15.5; mass spectrum (API-TIS) m/z 313 (MH$^+$).

6b. 1-(1-(Cyclohexylmethyl)-3-vinylpyrazol-5-yl)-4-(methylsulfonyl)benzene

The title compound was prepared as a white solid (78 mg, 74%) from the product of Example 6a by following the procedure for Example 4d; mp 136-138° C. $^1$H NMR (300 MHz, CDCl$_3$) δ 8.03 (dd, J=1.8 and 6.8 Hz, 2H), 7.59 (dd, J=1.8 and 6.8 Hz, 2H), 6.68-6.78 (m, 1H), 6.45 (s, 1H), 5.74 (dd, J=1.2 and 17.8 Hz, 1H), 5.33 (dd, J=1.2 and 11.0 Hz, 1H), 3.91 (d, J=7.3 Hz, 2H), 3.12 (s, 3H), 1.74-1.98 (m, 1H), 1.40-1.70 (m, 5H), 1.00-1.31 (m, 3H), 0.65-0.90 (m, 2H); $^{13}$C NMR (75 MHz, CDCl$_3$) δ150.4, 143.2, 140.5, 136.6, 129.9, 129.1, 127.9, 115.4, 103.6, 55.9, 44.5, 38.9, 30.5, 26.2, 25.6; mass spectrum (API-TIS) m/z 345 (MH$^+$); Anal. calcd for C$_{19}$H$_{24}$N$_2$O$_2$S.¼ mol H$_2$O: C, 65.39; H, 7.08; N, 8.03. Found: C, 65.43; H, 7.13; N, 7.95.

Example 7

Methyl (2E)-3-(1-(cyclohexylmethyl)-5-(4-(methylsulfonyl)phenyl) pyrazol-3-yl)prop-2-enoate 7a. Methyl (2E)-3-(1-(cyclohexylmethyl)-5-(4-(methylsulfonyl)phenyl)pyrazol-3-yl) prop-2-enoate The title compound was prepared as a white foam (0.24 g, 74%) from the product of Example 4b by following the procedure for Example 4d; mp 48-50° C.; $^1$H NMR (300 MHz, CDCl$_3$) δ 8.06 (d, J=8.3 Hz, 2H), 7.70 (d, J=16.0 Hz, 1H), 7.60 (d, J=8.2 Hz, 2H), 6.54 (s, 1H), 6.44 (d, J=16.0 Hz, 1H), 3.95 (d, J=7.3 Hz, 2H), 3.81 (s, 3H), 3.13 (s, 3H), 1.80-1.95 (m, 1H), 1.38-1.70 (m, 5H), 0.98-1.27 (m, 3H), 0.62-0.87 (m, 2H); $^{13}$C NMR (75 MHz, CDCl$_3$) δ 167.4, 147.5, 143.7, 140.9, 136.7, 136.1, 130.1, 128.1, 119.1, 106.0, 56.3, 51.8, 44.6, 39.0, 30.6, 26.2, 25.7; mass spectrum (API-TIS) m/z 403 (MH$^+$); Anal. calcd for C$_{21}$H$_{26}$N$_2$O$_4$S: C, 62.66; H, 6.51; N, 6.96. Found: C, 62.40; H, 6.49; N, 6.84.

Example 8

Methyl 5-(4-(methylsulfonyl)phenyl)-1-benzylpyrazole-3-carboxylate

8a. Methyl 5-(4-(methylsulfonyl)phenyl)-1-benzylpyrazole-3-carboxylate

The title compound was prepared from the product of Example 3a by following the procedure for Example 4d to give a white solid (0.23 g, 63% yield); mp 142-143° C. $^1$H NMR (300 MHz, CDCl$_3$) δ 7.96 (d, J=8.1 Hz, 2H), 7.48 (d, J=8.1 Hz, 2H), 7.27-7.28 (m, 3H), 6.98-7.02 (m, 2H), 6.98 (s, 1H), 5.45 (s, 2H), 3.98 (s, 3H), 3.08 (s, 3H). $^{13}$C NMR (75 MHz, CDCl$_3$) δ 162.6, 143.5, 143.4, 141.3, 136.1, 135.0, 129.9, 129.0, 128.2, 128.0, 126.8, 110.4, 54.7, 52.4, 44.6;

mass spectrum (API-TIS) m/z 371 (MH+), 387 (MNH4+); Anal. Calcd for $C_{19}H_{18}N_2O_4S$: C, 61.61; H, 4.90; N, 7.56, S, 8.65. Found: C, 61.36; H, 4.85; N, 7.46; S, 8.95.

Example 9

3-(4-(Methylsulfonyl)phenyl)-5-(trifluoromethyl)(2-pyridyl) Phenyl Ketone and 2-(3-(4-(methylsulfonyl)phenyl)-5-(trifluoromethyl)(2-pyridyl))-2-phenylethanenitrile 9a. 3-(4-(Methylsulfonyl)phenyl)-5-(trifluoromethyl)(2-pyridyl) Phenyl Ketone To 2-(3-Chloro-5-(trifluoromethyl)(2-pyridyl))-2-phenylethanenitrile (Ryan Scientific Inc., South Carolina, U.S., 4.8 g, 16.17 mmol) and 4-(methylthio)benzeneboronic acid (4.15 g, 25 mmol) dissolved in anhydrous dioxane (80 mL) were added successively, tris(dibenzylideneacetone)dipalladium (0.58 g, 0.633 mmol), tri-tert-butylphosphine (150 mg, 0.724 mmol) followed by cesium carbonate (6.5 g, 20 mmol). The resulting mixture was heated at reflux overnight under a nitrogen atmosphere. Additional 4-(methylthio)benzeneboronic acid (4.15 g, 25 mmol), tris(dibenzylideneacetone)dipalladium(0) (0.58 g, 0.633 mmol), tri-tert-butylphosphine (150 mg, 0.724 mmol) and cesium carbonate (6.5 g, 20 mmol) were added and the reaction mixture was heated at reflux for another 24 hours, then cooled to room temperature and solvent was evaporated. The residue was treated with water and then extracted with ethyl acetate (1×250 mL). The combined organic extracts were washed with water (4×250 mL), brine (1×250 mL), dried over sodium sulfate, treated with charcoal, filtered and concentrated to give the crude product. Purification by column chromatography over silica gel using 5% ethyl acetate in hexane gave a thick oil (1.3 g) that was a mixture (85:15) of 2-(3-(4-methylthiophenyl)-5-(trifluoromethyl)(2-pyridyl))-2-phenylethanenitrile and 3-(4-methylthiophenyl)-5-(trifluoromethyl)(2-pyridyl) phenyl ketone. This mixture was dissolved in methanol (60 mL) and OXONE® (4.35 g, 7.1 mmol) in water (15 mL) was added, and then stirred at room temperature for 1.5 hours. The resulting mixture was neutralized with ammonium hydroxide, the solvent was evaporated and the residue extracted with ethyl acetate (2×50 mL). The combined organic extracts were washed with water (2×50 mL), brine (1×25 mL), dried over sodium sulfate, filtered and solvent was evaporated to give the crude product. Purification by column chromatography over silica gel using a gradient of 20 to 40% ethyl acetate in hexane gave the less polar compound, 3-(4-(methylsulfonyl)phenyl)-5-(trifluoromethyl)(2-pyridyl) phenyl ketone, as a white crystalline product (85 mg), mp 141-142° C. $^1$H NMR (CDCl$_3$) δ 9.03 (s, 1H), 8.14 (d, J=1.3 Hz, 1H), 7.96 (d, J=8.3 Hz, 2H), 7.85 (dd, J=7.2 and 1.0 Hz, 2H), 7.66 (t, J=7.6 Hz, 1H), 7.58 (d, J=8.3 Hz, 2H), 7.51 (t, J=7.5 Hz, 2H), 3.03 (s, 3H); $^{13}$C NMR (CDCl$_3$) δ 193.1, 158.2, 145.05, 141.5, 140.7, 135.3, 134.3, 130.3 (2C), 129.7 (2C), 128.2 (2C), 127.8, (2C), 127.0 (q, J=33 Hz, CF$_3$), 124.6, 121.0, 44.3; LRMS (APIMS) m/z 406 (M+H)+.

9b. 2-(3-(4-(methylsulfonyl)phenyl)-5-(trifluoromethyl)(2-pyridyl))-2-phenylethanenitrile Purification of the more polar fractions of the product of Example 9a by column chromatography over silica gel using a gradient of 20 to 40% ethyl acetate in hexane gave the title compound, 2-(3-(4-(methylsulfonyl)phenyl)-5-(trifluoromethyl)(2-pyridyl))-2phenylethanenitrile, 490 mg, as a light yellow solid; mp 78° C.; $^1$H NMR (CDCl$_3$) δ 9.05 (s, 1H), 8.10 (d, J=1.6 Hz, 2H), 7.80 (s, 1H), 7.46 (d, J=8.2 Hz, 2H), 7.33 (m, 3H), 7.16 (m, 2H), 5.42 (s, 1H), 3.18 (s, 3H); $^{13}$C NMR (CDCl$_3$) δ 155.0, 146.6, 141.6, 141.4, 135.5, 135.1, 133.6, 130.1 (2C), 129.2 (2C), 128.1, 127.8, (2C), 127.0 (2×C), 126.3 (q, J=33 Hz, CF$_3$), 124.6, 121.0, 118.1, 44.4, 42.3; LRMS (APIMS) m/z 417 (M+H)+.

Example 10

3-Fluorophenyl 2-(4-(methylsulfonyl)phenyl)(3-pyridyl) ketone 10a. 2-Chloro(3-pyridyl) 3-fluorophenyl Ketone The Grignard reagent was prepared by refluxing 1-bromo-3-fluorobenzene (1.75 g, 10 mmol) and magnesium metal (267 mg, 11 mmol) and a few crystals of iodine in anhydrous THF (40 mL) under nitrogen atmosphere until most of the magnesium metal was consumed. The reagent was cooled to room temperature and 2-chloro-3-nicotinoyl chloride (1.76 g, 10 mmol) in anhydrous THF (20 mL) was added and the resulting mixture was stirred at room temperature for 15 minutes and then quenched with saturated aqueous ammonium chloride solution. The organic layer was separated and the aqueous layer was extracted with ethyl acetate (1×50 mL). The combined organic layers were dried over anhydrous sodium sulfate, filtered and the filtrate concentrated to give the crude product. Purification by flash column chromatography using 20% ethyl acetate in hexane gave the title compound (2.35 g) in nearly quantitative yield, as a colorless thick oil. $^1$H NMR (CDCl$_3$) δ 8.54 (dd, J=5.0, 3.0 Hz, 1H), 7.73 (dd, J=7.5, 1.9 Hz, 1H), 7.5-7.2 (m, 5H); $^{13}$C NMR (CDCl$_3$) δ 192.0, 164.4, 161.1, 151.1, 147.6, 139.9, 134.3, 130.4, (d, $J_{C-F}$=7.5 Hz), 125.8, 122.3, 121.2 (d, $J_{C-F}$=22 Hz), 116.2 (d, $J_{C-F}$=22 Hz); LRMS (APIMS) m/z 236 (M+H)+.

10b. 3-Fluorophenyl 2-(4-methylthiophenyl)(3-pyridyl) Ketone

The product of Example 10a (1.41 g, 6 mmol) and 4-(methylthio)benzeneboronic acid (1.66 g, 10 mmol) were dissolved in toluene (125 mL) and 2 M Na$_2$CO$_3$ (6 mL, 12 mmol) was added. To this mixture was added ethanol (10 mL) followed by tetrakis (triphenylphosphine) palladium (450 mg, 0.4 mmol) and the mixture was refluxed overnight under nitrogen atmosphere. The mixture was then cooled to room temperature and diluted with water (25 mL), stirred, and the aqueous layer was separated and extracted with ethyl acetate (1×75 mL). The combined organic layers were washed with water (4×50 mL), brine (1×50 mL), dried over sodium sulfate, filtered and concentrated at reduced pressure to give the crude product. Purification by column chromatography over silica gel using 20% ethyl acetate in hexane gave the title compound (900 mg, 46% yield) as a white solid; mp 91-92° C.; $^1$H NMR (CDCl$_3$) δ 8.88 (dd, J=4.8, 1.7 Hz, 1H), 7.88 (dd, J=7.6, 1.6 Hz, 1H), 7.5-7.35 (m, 5H), 7.3-7.25 (m, 1H), 7.2-7.15 (m, 3H), 2.51 (s, 3H); LRMS (APIMS) m/z 324 (M+H)+.

10c. 3-Fluorophenyl 2-(4-methylsulfonylphenyl)(3-pyridyl) ketone

The product of Example 10b (650 mg, 1.857 mmol) was dissolved in MeOH (40 mL). To this solution, OXONE® (2.848 g, 4.64 mmol) dissolved in H$_2$O (10 mL) was added. The mixture was stirred at room temperature for 1.5 hours, then diluted with water, and ammonium hydroxide added until the solution became basic. The solvent was evaporated and the product was extracted with ethyl acetate (2×75 mL), washed with brine (1×50 mL), dried over anhydrous sodium sulfate, filtered and solvent evaporated at reduced pressure to give an oil which upon trituration with hexane/ethyl acetate gave the title compound (650 mg, 99% yield); mp 157-159° C.; $^1$H NMR (CDCl$_3$) δ 8.92 (d, J=4.7 Hz, 1H), 7.94 (d, J=7.7 Hz, 1H), 7.88 (d, J=7.6 Hz, 2H), 7.74 (d, J=7.8 Hz, 2H), 7.53 (dd, J=7.7, 4.8 Hz, 1H), 7.47-7.3 (m, 3H), 7.2 (m, 1H), 3.18 (s, 3H); $^{13}$C NMR (CDCl$_3$) δ 195.1, 164.1, 160.8, 155.4, 151.3, 144.3, 140.5, 138.3, (d, J=6.4 Hz), 137.1, 134.1, 130.1 (2C), 128.1 (2C), 125.7, (d, J=3 Hz), 122.5, 120.8 (d, J=21.5 Hz), 116.2 (d, J=22 Hz), 44.4; LRMS (APIMS) m/z 356 (M+H)$^+$.

Example 11

2-(4-(Methylsulfonyl)phenyl)(3-pyridyl) 2-pyridyl Ketone 11a. 2-(4-Methylthiophenyl)(3-pyridyl) 2-pyridyl Ketone 2-Chloro(3-pyridyl) 2-pyridyl ketone (Ryan Scientific Inc., South Carolina, U.S.) (810 mg, 3.7 mmol) and 4-(methylthio)benzeneboronic acid (830 mg, 5 mmol) were dissolved in toluene (50 mL) and ethanol (5 mL). To this solution was added 2 M Na$_2$CO$_3$ (6 mL, 12 mmol) followed by tetrakis (triphenylphosphine)palladium (250 mg, 0.2 mmol) and the resulting mixture was refluxed overnight under nitrogen atmosphere. The mixture was then cooled to room temperature and diluted with water (25 mL), stirred and the aqueous layer was separated and extracted with ethyl acetate (1×75 mL). The combined organic layers were washed with water (2×50 mL), brine (1×50 mL), dried over sodium sulfate, filtered and concentrated at reduced pressure to give the crude product. Purification by column chromatography over silica gel using 40% ethyl acetate in hexane gave the title compound (770 mg, 68% yield) as a white solid; mp 122-123° C.; $^1$H NMR (CDCl$_3$) δ 8.87 (dd, J=4.8 and 1.7 Hz, 1H), 8.45 (d, J=4.7 Hz, 1H), 8.0 (dd, J=7.7 and 1.4 Hz, 2H), 7.75 (m, 1H), 7.45-7.3 (m, 4H), 7.12 (d, J=8.4 Hz, 2H), 2.44 (s, 3H); $^{13}$C NMR (CDCl$_3$) δ 196.0, 157.6, 153.5, 150.7, 148.8, 139.3, 137.4, 136.6, 136.5, 133.6, 129.4 (2C), 126.5, 125.7 (2C), 123.5, 121.1, 15.3; LRMS (APIMS) m/z 307 (M+H)$^+$.

11b. 2-(4-(Methylsulfonyl)phenyl)(3-pyridyl) 2-pyridyl Ketone

The product of Example 11a (670 mg, 2.2 mmol) was dissolved in MeOH (50 mL). To this solution, OXONE® (3.07 g, 5 mmol) dissolved in H$_2$O (20 mL) was added. The reaction mixture was stirred at room temperature overnight, it was then diluted with water, ammonium hydroxide added until the solution became basic and the solvent was evaporated. The product was extracted with ethyl acetate (2×75 mL), washed with brine (1×50 mL), dried over anhydrous sodium sulfate, filtered and solvent evaporated at reduced pressure to give an oil which upon trituration with hexane:ethyl acetate (80:20) gave the title compound (670 mg, 99%) as a white solid; mp 143-147° C.; $^1$H NMR (CDCl$_3$) δ 8.90 (dd, J=4.8 and 1.6 Hz, 1H), 8.43 (d, J=4.3 Hz, 1H), 8.06 (d, J=7.7, 2H), 7.80 (m, 3H), 7.71 (d, J=8.4 Hz, 2H), 7.52 (dd, J=7.7 and 4.8 Hz, 1H), 7.3 (m, 1H), 3.0 (s, 3H); $^{13}$C NMR (CDCl$_3$) δ 196.2, 156.4, 153.1, 150.9, 148.9, 145.5, 140.1, 137.7, 136.9, 134.3, 130.1 (2C), 127.1 (2C), 127.0, 123.7, 122.4, 44.4; LRMS (APIMS) m/z 339 (M+H)$^+$.

Example 12

Ethyl 3-((2-(4-(methylsulfonyl)phenyl)-3-pyridyl) carbonyl)benzoate

12a. Ethyl 3-((2-(4-methylthiophenyl)-3-pyridyl)carbonyl) benzoate

To ethyl 3-((2-chloro-3-pyridyl)carbonyl)benzoate (Ryan Scientific Inc., South Carolina, U.S., 950 mg, 3.3 mmol) in ethanol (5 mL) was added 2 M Na$_2$CO$_3$ (3.3 mL, 6.6 mmol) followed by tetrakis (triphenylphosphine)palladium (250 mg, 0.2 mmol) and the resulting mixture was refluxed overnight under nitrogen atmosphere. The mixture was then cooled to room temperature and diluted with water (25 mL), stirred and the aqueous layer was separated and extracted with ethyl acetate (1×75 mL). The combined organic layers were washed with water (2×50 mL), brine (1×50 mL), dried over sodium sulfate, filtered and evaporated to give the crude product. Purification by column chromatography over silica gel using 10% ethyl acetate in hexane gave the title compound (1.24 g) as a thick oil in nearly quantitative yield. $^1$H NMR (CDCl$_3$) δ 8.9 (dd, J=7.8, 1.8 Hz, 1H), 8.31 (s, 1H), 8.16 (dt, J=7.9, 1.4 Hz, 1H), 7.91 (dd, J=7.7, 1.8 Hz, 1H), 7.88 (dt, J=7.9 and 1.4 Hz, 1H), 7.5-7.4 (m, 4H), 7.15 (d, J=7.7 Hz, 2H), 4.40 (q, J=7.1 Hz, 2H), 2.43 (s, 3H), 1.42 (t, J=7.1 Hz, 3H); $^{13}$C NMR (CDCl$_3$) δ 196.4, 165.4, 156.9, 151.1, 140.1, 137.2, 136.7, 135.7, 134.0, 133.6, 130.8, 129.5 (2×C), 128.6, 125.9, (2C), 121.5, 61.3, 15.3 14.2; LRMS (APIMS) m/z 378 (M+H)$^+$.

12b. Ethyl 3-((2-(4-(methylsulfonyl)phenyl)-3-pyridyl)carbonyl)benzoate

To the product of Example 12a (1.3 g, 3.44 mmol) in MeOH (180 mL) was added OXONE® (6.14 g, 10 mmol) dissolved in H$_2$O (50 mL). The resulting mixture was stirred at room temperature for 1 hour, then diluted with water, and ammonium hydroxide was added until the solution became basic and the solvent was evaporated. The product was extracted with ethyl acetate (2×75 mL), washed with brine (1×50 mL), dried over anhydrous sodium sulfate, filtered and solvent evaporated to give an oil which upon trituration with hexane:ethyl acetate (90:10) gave the title compound (1.34 g, 95% yield) as a white solid; mp 125-132° C.; $^1$H NMR (CDCl$_3$) δ 8.92 (dd, J=4.5, 1.1 Hz, 1H), 8.30 (s, 1H), 8.16 (d, J=7.7 Hz, 1H), 7.96 (dd, J=7.7, 1.41 Hz, 1H), 7.90 (d, J=7.9 Hz, 1H), 7.84 (d, J=8.3 Hz, 2H), 7.75 (d, J=8.3 Hz, 2H), 7.54 (dd, J=7.7, 4.9 Hz, 1H), 7.46 (t, J=7.2 Hz, 1H), 4.39 (q, J=7.2 Hz, 2H), 2.97 (s, 3H), 1.41 (t, J=7.2 Hz, 3H); $^{13}$C NMR (CDCl$_3$) δ 195.5, 165.1, 155.5, 151.3, 144.4, 140.4, 137.3, 136.4, 134.3, 134.1, 133.5, 131.0, 130.9, 130.1 (2C), 128.9, 127.3 (2C), 122.7, 61.4, 44.3, 14.2; LRMS (APIMS) m/z 410 (M+H)$^+$.

Example 13

Assay for Human COX-1 and COX-2 Enzyme Activity in Human Whole Blood

The assay for COX-1 and COX-2 enzyme activity, in the human whole blood was performed as described in Brideau et al., *Inflamm Res.*, 45: 68-74 (1996)). Human blood (≈50 mL) from male or female donors who had not received any aspirin or NSAIDs for 14 days was collected at two local area blood donor centers and placed in polypropylene syringes containing sodium heparin (20 units per mL blood, final concentration). The blood was transported to the laboratory on ice packs and used within 1.5 hours of collection.

Upon receipt in the laboratory, the blood was allowed to come to room temperature for 15 minutes prior to distribution in 1 mL aliquots per well of 24 well tissue culture plates. The plates were then placed on a gently rotating platform shaker in a 5% $CO_2$ incubator at 37° C. for 15 minutes. Test compounds were dissolved in DMSO, at 1000 fold the final desired concentration, and further diluted, as indicated, in DMSO. One μL of each dilution of the test compound was added per well, in duplicate wells; wells not receiving test compound (e.g., basal, background or control wells) received 1 μL DMSO.

To induce COX-2, lipopolysaccharide (LPS) from *E. coli* (LPS, serotype 026:B6 or serotype 0127:B8, Sigma Chemical Co., St. Louis, Mo., Catalogue No. L3755 or L3129, respectively) was added at 10 μg/mL (2 μL of 5 mg/mL LPS in DMSO) to appropriate wells 15 minutes after the addition of the test compound. (Basal or background wells not incubated with LPS received 2 μL of DMSO.) For the stimulation of COX-1, the calcium ionophore, A23187 (free acid from Sigma Chemical Co., St. Louis, Mo., Catalogue No. C7522) was added at 25 μM (1 μL of 25 mM stock in DMSO) to separate wells 4.5 hours after the addition of the test compound. (Again, basal, background or control wells not stimulated with A23187 received 1 μL of DMSO.) At 5 hours after the addition of the test compound, all incubations were terminated by placement on ice and the addition of 2 mM EGTA (100 μL of 20 mM EGTA, tetrasodium, in PBS (phosphate buffered saline) without $Ca^{++}$ and $Mg^{++}$, pH 7.2)). The resulting solutions, were transferred by polyethylene transfer pipettes to 15 mL polypropylene centrifuge tubes and centrifuged at 1200 g for 10 minutes at 4° C. One hundred μL of plasma was removed from each blood sample and added to 1 mL of methanol in new 15 mL polypropylene centrifuge tubes, vortexed, and stored overnight at −20° C. The next day, the samples were centrifuged at 2000 g for 10 minutes at 4° C. and the supernatants transferred to glass tubes and evaporated to dryness. The samples were assayed for thromboxane $B_2$ using EIA kits supplied by Cayman Chemical Co. (Ann Arbor, Mich., Catalogue No. 519031) in duplicate wells after reconstitution with EIA Buffer and appropriate dilution (2000 fold for COX-1 and 500 fold for Cox-2 samples).

The % inhibition for COX-1 and COX-2 enzyme activity in human whole blood by the test compounds, at the indicated concentrations, are given in Table 1.

TABLE 1

% INHIBITION OF COX-1 AND COX-2 ENZYME ACTIVITY IN HUMAN WHOLE BLOOD

| Test Compound | COX-1 Inhibition (% at 100 μM) | COX-2 Inhibition (% at 10 μM) | COX-2 Inhibition (% at 1 μM) |
|---|---|---|---|
| Example 1g | 65 | 45 | 0 |
| Example 1h | 25 | 65 | 10 |
| Example 2e | 65 | 65 | 25 |
| Example 2f | 70 | 75 | 20 |
| Example 3c | 25 | 15 | 10 |
| Example 3d | 55 | 40 | 20 |
| Example 4d | 50 | 45 | 25 |
| Example 4e | 40 | 75 | 35 |
| Example 5b | 90 | 90 | 45 |
| Example 5c | 90 | 100 | 75 |
| Example 6b | 30 | 100 | 70 |
| Example 7 | 5 | 30 | 15 |
| Example 8 | 55 | 25 | 15 |
| Example 9a | 90 | 90 | 60 |
| Example 9b | −10 | 55 | 35 |
| Example 10c | 5 | 50 | 55 |

TABLE 1-continued

% INHIBITION OF COX-1 AND COX-2 ENZYME ACTIVITY IN HUMAN WHOLE BLOOD

| Test Compound | COX-1 Inhibition (% at 100 μM) | COX-2 Inhibition (% at 10 μM) | COX-2 Inhibition (% at 1 μM) |
|---|---|---|---|
| Example 11b | 0 | 15 | 0 |
| Example 12b | 25 | 20 | 10 |

The results show that the compounds in Table 1 have COX-2 selectivity.

Example 10

Rat Carrageenan Air-Pouch

The carrageenan air pouch model was performed as described by Sedgwick, A. D., et al., *Agents Actions* 18, 429-438, (1986) and Masferrer et al., *Proc. Natl. Acad. Sci.* 91, 3228-3232 (1994). Air pouches were produced by subcutaneous injection of 20 ml of sterile air on day (−6) into the intrascapular area of the back of the anesthesia rat (male CD, Charles River, 175-200 g). An additional 10 mL of sterile air was injected into the pouch 3 days later to keep the space open and to assist in the development of the interior membrane. Six days after the initial air injection, 1 mL of a 1% solution of carrageenan (Sigma, lambda fraction) dissolved in pyrogen-free saline was injected directly into the pouch to produce an inflammatory response. The test compound in vehicle (3 mL/rat, 0.5% Methocel) was administered by oral intubation 1 hour prior to carrageenan injection into the inflammatory pouch. After 4 hours the exudate was removed by pipette into a calibrated centrifuge tube and the volume measured. The number of leukocytes in the exudate was determined by cell counting with a Beckman Coulter Particle Counter with the lower threshold set to exclude red blood cells. The exudate samples were assayed without further processing for $PGE_2$ (prostaglandin $E_2$) using $PGE_2$ EIA kit-Monoclonal, friom Cayman Chemical Co. (Ann Arbor, Mich., Catalogue No. 514010).

The % inhibition for the cell infiltration and the % inhibition for $PGE_2$ by the test compounds, at the indicated concentrations, are given in Table 2.

TABLE 2

| Test Compound | Cell Infiltration (% inhibition @ 45 μmol/kg) | PGE-2 (% Inhibition at @ 45 μmol/kg) |
|---|---|---|
| Example 2f | 42 | 85 |

The compound in Table 2 inhibited cell infiltration with an accompanying decrease in $PGE_2$ levels.

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the invention.

What is claimed is:

1. A compound of Formula (II), or a pharmaceutically acceptable salt thereof;
wherein the compound of Formula (II) is:

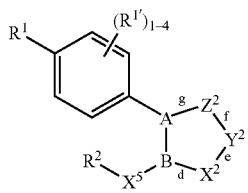

wherein:
A-B is:
C—N;
when A-B is C—N, sides e and g are double bonds, and sides d and f are single bonds, —$X^2$—$Y^2$-$Z^2$ is:
—N=$CR^4$—$CR^5$=;
$R^1$ is:
(a) —$S(O)_2$—$CH_3$;
(b) —$S(O)_2$—$NR^8(D^1)$;
(c) —$S(O)_2$—$N(D^1)$—C(O)—$CF_3$;
(d) —S(O)—(NH)—$NH(D^1)$; or
(e) —S(O)—(NH)—$N(D^1)$—C(O)—$CF_3$;
$R^{1'}$ at each occurrence is independently:
(a) hydrogen;
(b) halogen;
(c) methyl; or
(d) $CH_2OH$;
$R^2$ is:
(a) lower alkyl;
(b) cycloalkyl;
(c) mono-, di- or tri-substituted phenyl or naphthyl, wherein the substituents are each independently:
(1) hydrogen;
(2) halo;
(3) alkoxy;
(4) alkylthio;
(5) CN;
(6) haloalkyl, preferably $CF_3$;
(7) lower alkyl;
(8) $N_3$;
(9) —$CO_2D^1$;
(10) —$CO_2$-lower alkyl;
(11) —$(C(R^5)(R^6))_z$—$OD^1$;
(12) —$(C(R^5)(R^6))_z$—O-lower alkyl;
(13) lower alkyl—$CO_2$—$R^5$;
(14) —$OD^1$;
(15) haloalkoxy;
(16) amino;
(17) nitro;
(18) alkylsulfinyl; or
(19) heteroaryl;
$R^3$ is:
(a) hydrogen;
(b) haloalkyl, preferably $CF_3$;
(c) CN;
(d) lower alkyl;
(e) —$(C(R_e)(R_f))_p$—U—V;
(f) K;
(g) unsubstituted or substituted:
(1) lower alkyl-Q;
(2) lower alkyl-O— lower alkyl-Q;
(3) lower alkyl-S-lower alkyl-Q;
(4) lower alkyl-O-Q;
(5) lower alkyl-S-Q;
(6) lower alkyl-O—V;
(7) lower alkyl-S—V;
(8) lower alkyl-O—K; or
(9) lower alkyl-S—K;
wherein the substituent(s) reside on the lower alkyl group;
(h) Q;
(i) alkylcarbonyl;
(j) arylcarbonyl;
(k) alkylarylcarbonyl;
(l) arylalkylcarbonyl;
(m) carboxylic ester;
(n) carboxamido;
(o) cycloalkyl;
(p) mono-, di- or tri-substituted phenyl or naphthyl, wherein the substituents are each independently:
(1) hydrogen;
(2) halo;
(3) alkoxy;
(4) alkylthio;
(5) CN;
(6) haloalkyl, preferably $CF_3$;
(7) lower alkyl;
(8) $N_3$;
(9) —$CO_2D^1$;
(10) —$C_2$-lower alkyl;
(11) —$(C(R^5)(R^6))_z$—$OD^1$;
(12) —$(C(R^5)(R^6))_z$—O-lower alkyl;
(13) lower alkyl-$CO_2$—$R^5$;
(14) —$OD^1$;
(15) haloalkoxy;
(16) amino;
(17) nitro; or
(18) alkylsulfinyl;
(q) alkenyl;
(r) alkynyl;
(s) arylalkyl;
(t) lower alkyl-$OD^1$;
(u) alkoxyalkyl;
(v) aminoalkyl;
(w) lower alkyl-$CO_2R^{10}$;
(x) lower alkyl-$C(O)NR^{10}(R^{10})$;
(y) heterocyclicalkyl; or
(z) heterocyclic ring-C(O)—;
$R^4$, $R^{4'}$, $R^5$ and $R^{5'}$ are each independently:
(a) hydrogen;
(b) amino;
(c) CN;
(d) lower alkyl;
(e) haloalkyl;
(f) alkoxy;
(g) alkylthio;
(h) Q;
(i) —O-Q;
(j) —S-Q;
(k) K;
(l) cycloalkoxy;
(m) cycloalkylthio;
(n) unsubstituted, mono-, or di-substituted phenyl or unsubstituted, mono-, or di-substituted benzyl, wherein the substituents are each independently:
(1) halo;
(2) lower alkyl;
(3) alkoxy;
(4) alkylthio;

(5) CN;
(6) haloalkyl, preferably $CF_3$;
(7) $N_3$;
(8) Q;
(9) nitro; or
(10) amino;
(o) unsubstituted, mono-, or di-substituted heteroaryl or unsubstituted, mono-, or di-substituted heteroarylmethyl, wherein the heteroaryl is a monocyclic aromatic ring of 5 atoms, said ring having one heteroatom which is S, O, or N, and, optionally, 1, 2, or 3 additional N atoms; or the heteroaryl is a monocyclic ring of 6 atoms, said ring having one heteroatom which is N, and, optionally, 1, 2, 3, or 4 additional N atoms; said substituents are each independently:
(1) halo;
(2) lower alkyl;
(3) alkoxy;
(4) alkylthio;
(5) CN;
(6) haloalkyl, preferably $CF_3$;
(7) $N_3$;
(8) —$C(R^6)(R^7)$—$OD^1$;
(9) —$C(R^6)(R^7)$—O-lower alkyl; or
(10) alkylsulfinyl
(p) —$CON(R^8)(R^8)$;
(q) —$CH_2OR^8$;
(r) —$CH_2OCN$;
(s) unsubstituted or substituted:
(1) lower alkyl-Q;
(2) —O-lower alkyl-Q;
(3) —S-lower alkyl-Q;
(4) lower alkyl-O-lower alkyl-Q;
(5) lower alkyl-S-lower alkyl-Q;
(6) lower alkyl-O-Q;
(7) lower alkyl-S-Q;
(8) lower alkyl-O—K;
(9) lower alkyl-S—K;
(10) lower alkyl-O—V; or
(11) lower alkyl-S—V;
wherein the substituent(s) resides on the lower alkyl;
(t) cycloalkyl;
(u) aryl;
(v) arylalkyl;
(w) cycloalkylalkyl;
(x) aryloxy;
(y) arylalkoxy;
(z) arylalkylthio;
(aa) cycloalkylalkoxy;
(bb) heterocycloalkyl;
(cc) alkylsulfonyloxy;
(dd) alkylsulfonyl;
(ee) arylsulfonyl;
(ff) arylsulfonyloxy;
(gg) —$C(O)R^{10}$;
(hh) nitro;
(ii) amino;
(jj) aminoalkyl;
(kk) —C(O)-alkyl-heterocyclic ring;
(ll) halo;
(mm) heterocyclic ring;
(nn) —$CO_2D^1$;
(oo) carboxyl;
(pp) amidyl; or
(qq) alkoxyalkyl;
alternatively, $R^4$ and $R^5$ together with the carbons to which they are attached are:

(a) cycloalkyl;
(b) aryl; or
(c) heterocyclic ring;
alternatively, $R^4$ and $R^{4'}$ or $R^5$ and $R^{5'}$ taken together with the carbon to which they are attached are:
(a) cycloalkyl; or
(b) heterocyclic ring;
alternatively, $R^4$ and $R^5$, $R^{4'}$ and $R^{5'}$, $R^4$ and $R^{5'}$, or $R^{4'}$ and $R^5$ when substituents on adjacent carbon atoms taken together with the carbons to which they are attached are:
(a) cycloalkyl;
(b) heterocyclic ring; or
(c) aryl;
$R^6$ and $R^7$ are each independently:
(a) hydrogen;
(b) unsubstituted, mono- or di-substituted phenyl; unsubstituted, mono- or di-substituted benzyl; unsubstituted, mono- or di-substituted heteroaryl; mono- or di-substituted heteroarylmethyl, wherein said substituents are each independently:
(1) halo;
(2) lower alkyl;
(3) alkoxy;
(4) alkylthio;
(5) CN;
(6) haloalkyl, preferably $CF_3$;
(7) $N_3$;
(8) —$C(R^{14})(R^{15})$—$OD^1$; or
(9) —$C(R^{14})(R^{15})$—O-lower alkyl;
(c) lower alkyl;
(d) —$CH_2OR^8$;
(e) CN;
(f) —$CH_2CN$;
(g) haloalkyl, preferably fluoroalkyl;
(h) —$CON(R^8)(R^8)$;
(i) halo; or
(j) —$OR^8$;
$R^8$ is:
(a) hydrogen;
(b) K; or
(c) $R^9$;
alternatively, $R^5$ and $R^{5'}$, $R^6$ and $R^7$ or $R^7$ and $R^8$ together with the carbon to which they are attached form a saturated monocyclic ring of 3, 4, 5, 6 or 7 atoms; optionally containing up to two heteroatoms selected from oxygen, $S(O)_o$ or $NR_j$;
$R^9$ is:
(a) lower alkyl;
(b) lower alkyl-$CO_2D^1$;
(c) lower alkyl-$NHD^1$;
(d) phenyl or mono-, di- or tri-substituted phenyl, wherein the substituents are each independently:
(1) halo;
(2) lower alkyl;
(3) alkoxy;
(4) alkylthio;
(5) lower alkyl-$CO_2D^1$;
(6) lower alkyl-$NHD^1$;
(7) CN;
(8) $CO_2D^1$; or
(9) haloalkyl, preferably fluoroalkyl;
(e) benzyl, mono-, di- or tri-substituted benzyl, wherein the substituents are each independently:
(1) halo;
(2) lower alkyl;
(3) alkoxy;

(4) alkylthio;
(5) lower alkyl-$CO_2D^1$;
(6) lower alkyl-$NHD^1$;
(7) CN;
(8) —$CO_2D^1$; or
(9) haloalkyl, preferably $CF_3$;
(f) cycloalkyl;
(g) K; or
(h) benzoyl, mono-, di-, or trisubstituted benzoyl, wherein the substituents are each independently:
  (1) halo;
  (2) lower alkyl;
  (3) alkoxy;
  (4) alkylthio;
  (5) lower alkyl-$CO_2D^1$;
  (6) lower alkyl-$NHD^1$;
  (7) CN;
  (8) —$CO_2D^1$; or
  (9) haloalkyl, preferably $CF_3$;
$R^{10}$ and $R^{10'}$ are each independently:
  (a) hydrogen; or
  (b) $R^{11}$;
$R^{11}$ is:
  (a) lower alkyl;
  (b) cycloalkyl;
  (c) unsubstituted, mono-, di- or tri-substituted phenyl or naphthyl, wherein the substituents are each independently:
    (1) halo;
    (2) alkoxy;
    (3) alkylthio;
    (4) CN;
    (5) haloalkyl, preferably $CF_3$;
    (6) lower alkyl;
    (7) $N_3$;
    (8) —$CO_2D^1$;
    (9) —$CO_2$-lower alkyl;
    (10) —$C(R^{12})(R^{13})$—$OD^1$;
    (11) —$C(R^{12})(R^{13})$—O-lower alkyl;
    (12) lower alkyl—$CO_2D^1$;
    (13) lower alkyl-$CO_2R^{12}$;
    (14) benzyloxy;
    (15) —O-(lower alkyl)-$CO_2D^1$;
    (16) —O-(lower alkyl)—$CO_2R^{12}$; or
    (17) —O-(lower alkyl)-$NR^{12}R^{13}$;
  (d) unsubstituted, mono-, di- or tri-substituted heteroaryl, wherein the heteroaryl is a monocyclic aromatic ring of 5 atoms, said ring having one heteroatom which is S, O, or N, and, optionally, 1, 2, or 3 additional N atoms; or said heteroaryl is a monocyclic ring of 6 atoms, said ring having one heteroatom which is N, and, optionally 1, 2, or 3 additional N atoms, and wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —$C(R^{12})(R^{13})$—$OD^1$; or
    (9) —$C(R^{12})(R^{13})$—O-lower alkyl;
  (e) unsubstituted, mono- or di-substituted benzoheterocycle, wherein the benzoheterocycle is a 5, 6, or 7-membered ring which contains 1 or 2 heteroatoms independently selected from O, S, or N, and, optionally, a carbonyl group or a sulfonyl group, wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —$C(R^{12})(R^{13})$—$OD^1$; or
    (9) —$C(R^{12})(R^{13})$—O-lower alkyl;
  (f) unsubstituted, mono- or di-substituted benzocarbocycle, wherein the carbocycle is a 5, 6, or 7-membered ring which optionally contains a carbonyl group, wherein said substituents are each independently:
    (1) halo;
    (2) lower alkyl;
    (3) alkoxy;
    (4) alkylthio;
    (5) CN;
    (6) haloalkyl, preferably $CF_3$;
    (7) $N_3$;
    (8) —$C(R^{12})(R^{13})$—$OD^1$; or
    (9) —$C(R^{12})(R^{13})$—O-lower alkyl;
  (g) hydrogen; or
  (h) K
$R^{12}$ and $R^{13}$ are each independently:
  (a) hydrogen;
  (b) lower alkyl; or
  (c) aryl; or
$R^{12}$ and $R^{13}$ together with the atom to which they are attached form a saturated monocyclic ring of 3, 4, 5, 6 or 7 atoms;
$R^{14}$ and $R^{15}$ are each independently:
  (a) hydrogen; or
  (b) lower alkyl; or
$R^{14}$ and $R^{15}$ together with the atom to which they are attached form a carbonyl, a thial, or a saturated monocyclic ring of 3, 4, 5, 6 or 7 atoms;
Q is:
  (a) —C(O)—U-$D^1$;
  (b) —$CO_2$-lower alkyl;
  (c) tetrazolyl-5-yl;
  (d) —$C(R^7)(R^8)(S-D^1)$;
  (e) —$C(R^7)(R^8)(O-D^1)$; or
  (f) —$C(R^7)(R^8)$(O-lower alkyl);
$X^5$ is:
  (a) —$(CR^{31}R^{32})_a$—;
  (b) —$(CR^{31}R^{32})_{bb}$-$A^1$-;
  (c) -$A^1$-$(CR^{31}R^{32})_{bb}$—;
  (d) —$CR^{31}R^{32}$-$A^1$-$CR^{31}R^{32}$—;
  (e) —$CR^{31}$=; or
  (f) -$A^1$;
$A^1$ is:
  (a) oxygen;
  (b) thio;
  (c) sulfinyl;
  (d) sulfonyl; or
  (e) —$N(R^{33})$—;
$R^{31}$ and $R^{32}$ are each independently:
  (a) hydrogen;
  (b) lower alkyl;
  (c) substituted lower alkyl;
  (d) lower alkoxy;
  (e) lower haloalkyl; or
  (f) halo; or $R^{31}$ and $R^{32}$ taken together are;
  (a) oxo;
  (b) thial;
  (c) oxime; or
  (d) hydrazone;
$R^{33}$ is:
  (a) lower alkyl;
  (b) hydrogen; or
  (c) —C(O)H;
a is an integer equal to 1 or 3;
bb is an integer equal to 2 or 3;
$D^1$ is:
  (a) hydrogen or
  (b) D;
D is:
  (a) V; or
  (b) K;
U is:
  (a) oxygen;
  (b) sulfur; or
  (c) —N($R_a$)($R_i$)—;
V is:
  (a) —NO;
  (b) —NO$_2$; or
  (c) hydrogen
K is —$W_{aa}$-$E_b$-(C($R_e$)($R_f$))$_p$-$E_c$-(C($R_e$)($R_f$))$_x$—$W_d$—(C($R_e$)($R_f$))$_y$—$W_i$-$E_j$-$W_g$-(C($R_e$)($R_f$))$_z$—U—V;
wherein aa, b, c, d, g, i and j are each independently an integer from 0 to 3;
p, x, y and z are each independently an integer from 0 to 10;
W at each occurrence is independently:
  (a) —C(O)—;
  (b) —C(S)—;
  (c) -T-;
  (e) alkyl;
  (f) aryl;
  (g) heterocyclic ring;
  (h) arylheterocyclic ring, or
  (i) —(CH$_2$CH$_2$O)$_q$—;
E at each occurrence is independently a -T-group, an alkyl group, an aryl group, a heterocyclic ring, —(C($R_e$)($R_f$))$_h$—, an arylheterocyclic ring or —(CH$_2$CH$_2$O)$_q$—;
h is an integer form 1 to 10;
q is an integer from 1 to 5;
$R_e$ and $R_f$ are each independently a hydrogen, an alkyl, a cycloalkoxy, a halogen, a hydroxy, an hydroxyalkyl, an alkoxyalkyl, an arylheterocyclic ring, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, -T-Q'-, or —(C($R_g$)($R_h$))$_k$-T-Q' or $R_e$ and $R_f$ taken together are an oxo, a thial, a heterocyclic ring, a cycloalkyl group, an oxime, a hydrazone or a bridged cycloalkyl group;

Q' is —NO or —NO$_2$;
k is an integer from 1 to 3;
T is independently a covalent bond, a carbonyl, an oxygen, —S(O)$_o$— or —N($R_a$)$R_i$—,
o is an integer from 0 to 2,
$R_a$ is a lone pair of electrons, a hydrogen or an alkyl group;
$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —OR'$_i$, —CH$_2$—C(T-Q')($R_g$)($R_h$), a bond to an adjacent atom creating a double bond to that atom or —(N$_2$O$_2$—)$^-$·M$^+$, wherein M$^+$ is an organic or inorganic cation; with the proviso that when $R_i$ is —CH$_2$—C(T-Q')($R_g$)($R_h$) or —(N$_2$O$_2$—)·M$^+$; then "-T-Q'" can be a hydrogen, an alkyl group, an alkoxyalkyl group, an aminoalkyl group, a hydroxy group or an aryl group;
$R_g$ and $R_h$ at each occurrence are independently $R_e$;
R'$_i$ is independently selected from $R_i$.

2. A composition comprising the compound of claim 1 and a pharmaceutically acceptable carrier.

3. The composition of claim 2, further comprising at least one therapeutic agent.

4. The composition of claim 3, wherein the therapeutic agent is a steroid, a nonsteroidal antiinflammatory compound, a 5-lipoxygenase (5-LO) inhibitor, a leukotriene B$_4$ receptor antagonist, a leukotriene A$_4$ hydrolase inhibitor, a 5-HT agonist, a 3-hydroxy-3-methyiglutaryl coenzyme A inhibitor, a H$_2$ antagonist, an antineoplastic agent, an antiplatelet agent, a thrombin inhibitor, a thromboxane inhibitor, a decongestant, a diuretic, a sedating or non-sedating antihistamine, an inducible nitric oxide synthase inhibitor, an opioid, an analgesic, a *Helicobacter pylori* inhibitor, a proton pump inhibitor, an isoprostane inhibitor, or a mixture of two or more thereof.

5. The composition of claim 4, wherein the nonsteroidal antiinflammatory compound is acetaminophen, aspirin, diclofenac, ibuprofen, ketoprofen, indomethacin or naproxen.

6. A composition comprising at least one compound of claim 1 and at least one compound that donates, transfers or releases nitric oxide, or induces the production of endogenous nitric oxide or endothelium-derived relaxing factor, or is a substrate for nitric oxide synthase.

7. The composition of claim 6, further comprising a pharmaceutically acceptable carner.

8. The composition of claim 6, wherein the compound that donates, transfers, or releases nitric oxide, or induces the production of endogenous nitric oxide or endothelium-derived relaxing factor or is a substrate for nitric oxide synthase is an S-nitrosothiol.

9. The composition of claim 8, wherein the S-nitrosothiol is S-nitroso-N-acetylcysteine, S-nitroso-captopril, S-nitroso-N-acetylpenicillamine, S-nitroso-homocysteine, S-nitroso-cysteine, S-nitroso-glutathione, or S-nitroso-cysteinylglycine.

10. The composition of claim 8, wherein the S-nitrosothiol is:
  (i) HS(C($R_e$)($R_f$))$_m$SNO;
  (ii) ONS(C($R_e$)($R_f$))$_m$$R_e$; or
  (iii) H$_2$N—CH(CO$_2$H)—(CH$_2$)$_m$—C(O)NH—CH(CH$_2$SNO)—C(O)NH—CH$_2$—CO$_2$H;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an aryiheterocyclic ring, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, -T-Q'-, or —(C $(R_g)(R_h))_k$-T-Q' or $R_e$ and $R_f$ taken together are an oxo, a methanthial, a heterocyclic ring, a cycloalkyl group, an oxime, a hydrazone or a bridged cycloalkyl group; Q' is —NO or —NO$_2$; and T is independently a covalent bond, a carbonyl, an oxygen, —S(O)$_o$— or —N($R_a$)$R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —CH$_2$—C (T-Q')($R_g$)($R_h$), or —(N$_2$O$_2$—)$^-$·M$^+$, wherein M$^+$ is an organic or inorganic cation; with the proviso that when $R_i$ is —CH$_2$—C(T-Q') ($R_g$)($R_h$) or —(N$_2$O$_2$—).M$^+$; then "-T-Q'" can be a hydrogen, an alkyl group, an alkoxyalkyl group, an aminoalkyl group, a hydroxy group or an aryl group; and $R_g$ and $R_h$ at each occurrence are independently $R_e$.

11. The composition of claim 6, wherein the compound that donates, transfers, or releases nitric oxide, or induces the production of endogenous nitric oxide or endothelium-derived relaxing factor, or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, nitrosated L-homoarginine, nitrosylated L-homoarginine), citrulline, omithine, glutamine, lysine, an arginase inhibitor or a nitric oxide mediator.

12. The composition of claim 6, wherein the compound that donates, transfers, or releases nitric oxide, or induces the production of endogenous nitric oxide or endothelium-derived relaxing factor, or is a substrate for nitric oxide synthase is:

(i) a compound that comprises at least one ON—O— or ON—N— group;

(ii) a compound that comprises at least one O$_2$N—O—, O$_2$N—N— or O$_2$N—S— or group;

(iii) a N-oxo-N-nitrosoamine having the formula: R$^{1''}$R$^{2''}$N—N(O-M$^+$)-NO, wherein R$^{1''}$ and R$^{2''}$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and M$^+$ is an organic or inorganic cation.

13. The composition of claim 12, wherein the compound comprising at least one ON—O— or ON—N— group is an ON—O-polypeptide, an ON—N-polypeptide, an ON—O-amino acid, an ON—N-amino acid, an ON—O-sugar, an ON—N-sugar, an ON—O-oligonucleotide, an ON—N-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, an ON—O-heterocyclic compound or an ON—N-heterocyclic compound.

14. The composition of claim 12, wherein compound comprising at least one O$_2$N—O—, O$_2$N—N— or O$_2$N—S— group is an O$_2$N—O-polypeptide, an O$_2$N—N-polypeptide, an O$_2$N—S-polypeptide, an O$_2$N—O-amino acid, O$_2$N—N-amino acid, O$_2$N—S-amino acid, an O$_2$N—O-sugar, an O$_2$N—N-sugar, O$_2$N—S-sugar, an O$_2$N—O-oligonucleotide, an O$_2$N—N-oligonucleotide, an O$_2$N—S-oligonucleotide, , a straight or branched, saturated or unsaturated, aliphatic or aromatic, substituted or unsubstituted O$_2$N—O-hydrocarbon, a straight or branched, saturated or unsaturated, aliphatic or aromatic, substituted or unsubstituted O$_2$N—N-hydrocarbon, a straight or branched, saturated or unsaturated, aliphatic or aromatic, substituted or unsubstituted O$_2$N—S-hydrocarbon, an O$_2$N—O-heterocyclic compound, an O$_2$N—N-heterocyclic compound or an O$_2$N—S-heterocyclic compound.

15. The composition of claim 6, further comprising at least one therapeutic agent.

16. The composition of claim 15, wherein the therapeutic agent is a steroid, a nonsteroidal antiinflammatory compound, a 5-lipoxygenase (5-LO) inhibitor, a leukotriene B$_4$ receptor antagonist, a leukotriene A$_4$ hydrolase inhibitor, a 5-HT agonist, a HMG CoA inhibitor, a H$_2$ antagonist, an antineoplastic agent, an antiplatelet agent, a thrombin inhibitor, a thromboxane inhibitor, a decongestant, a diuretic, a sedating or non-sedating anti-histamine, an inducible nitric oxide synthase inhibitor, an opioid, an analgesic, a *Helicobacter pylori inhibitor*, a proton pump inhibitor, an isoprostane inhibitor, or a mixture of two or more thereof.

17. The composition of claim 16, wherein the nonsteroidal antiinflammatory compound is acetaminophen, aspirin, diclofenac, ibuprofen, ketoprofen, indomethacin or naproxen.

18. A compound selected from the group consisting of:
1-(1-(cyclohexylmethyl)-3-(hydroxymethyl)pyrazol-5-yl)-4-(methylsulfonyl)benzene;
4-(1-(cyclohexylmethyl)-3-((2-hydroxyethoxy)methyl) pyrazol-5-yl)-1-(methylsulfonyl)benzene;
1-(3-(hydroxymethyl)-1-benzylpyrazol-5-yl)-4-(methylsulfonyl)benzene;
1-(3-((1E)-3-hydroxyprop-1-enyl)-1-(cyclohexylmethyl) pyrazol-5-yl)-4-(methylsulfonyl)benzene;
1-(1-(cyclohexylmethyl)-3-(3-hydroxypropyl)pyrazol-5-yl)-4-(methylsulfonyl)benzene;
1-(1-(cyclohexylmethyl)-3-vinylpyrazol-5-yl)-4-(methylsulfonyl)benzene;
methyl (2E)-3-(1-(cyclohexylmethyl)-5-(4-(methylsulfonyl)phenyl)pyrazol-3-yl) prop-2-enoate;
methyl 5-(4-(methylsulfonyl)phenyl)-1-benzylpyrazole-3-carboxylate;
1-(1-(cyclohexylmethyl)-3-((nitrooxy)methyl)pyrazol-5-yl)-4-(methylsulfonyl)benzene;
4-(1-(cyclohexylmethyl)-3-((2-(nitrooxy)ethoxy)methyl) pyrazol-5-yl)-1-(methylsulfonyl)benzene;
4-(methylsulfonyl)-1-(3-((nitrooxyl)methyl)-1-benzylpyrazol-5-yl)benzene;
1-(3-((1E)-3-nitrooxyprop-1-enyl)-1-(cyclohexylmethyl) pyrazol-5-yl)-4-(methylsulfonyl)benze;
1-(1-(cyclohexylmethyl)-3-(3-(nitrooxy)propyl)pyrazol-5-yl)-4-(methylsulfonyl) benzene;
or a pharmaceutically acceptable salt thereof.

19. A composition comprising at least one compound of claim 18 and a pharmaceutically acceptable carrier.

20. The composition of claim 19, further comprising (i) at least one compound that donates, transfers or releases nitric oxide, induces the production of endogenous nitric oxide or endothelium-derived relaxing factor, or is a substrate for nitric oxide synthase; (ii) at least one therapeutic agent; or (iii) at least one compound that donates, transfers or releases nitric oxide, induces the production of endogenous nitric oxide or endothelium-derived relaxing factor, or is a substrate for nitric oxide synthase and at least one therapeutic agent.

* * * * *